(12) United States Patent
Naumann et al.

(10) Patent No.: US 10,307,135 B2
(45) Date of Patent: Jun. 4, 2019

(54) INTRAVASCULAR ULTRASOUND NEEDLE GUIDE

(71) Applicant: Advanced Access Solutions, Inc., San Diego, CA (US)

(72) Inventors: Michael T Naumann, San Diego, CA (US); Thomas J Brannigan, San Diego, CA (US)

(73) Assignee: Advanced Access Solutions, Inc., San Diego, CA (US)

( * ) Notice: Subject to any disclaimer, the term of this patent is extended or adjusted under 35 U.S.C. 154(b) by 702 days.

(21) Appl. No.: 14/548,895

(22) Filed: Nov. 20, 2014

(65) Prior Publication Data
US 2015/0141836 A1    May 21, 2015

Related U.S. Application Data

(60) Provisional application No. 61/906,860, filed on Nov. 20, 2013.

(51) Int. Cl.
*A61B 17/34* (2006.01)
*A61B 8/12* (2006.01)
(Continued)

(52) U.S. Cl.
CPC .............. *A61B 8/0841* (2013.01); *A61B 8/00* (2013.01); *A61B 8/085* (2013.01); *A61B 8/0833* (2013.01);
(Continued)

(58) Field of Classification Search
None
See application file for complete search history.

(56) References Cited

U.S. PATENT DOCUMENTS 5,357,978 A * 10/1994 Turk ............... A61M 25/09041
600/585
5,954,670 A * 9/1999 Baker ................ A61B 17/3403
600/567
(Continued)

FOREIGN PATENT DOCUMENTS

EP        2 138 092         12/2009
JP        2002-509768       4/2002
(Continued)

OTHER PUBLICATIONS

International Search Report for International Application No. PCT/US2014/066723 dated May 6, 2015.
(Continued)

*Primary Examiner* — Carolyn A Pehlke
(74) *Attorney, Agent, or Firm* — Knobbe Martens Olson & Bear LLP

(57) ABSTRACT

An intravascular ultrasound "(IVUS)" device having an intrinsic or attachable needle guide is disclosed. In some embodiments, a sheath having a needle guide is used in connection with an IVUS device. The devices may be used in performing minimally invasive image-guided surgical procedures. The devices may be configured to maintain a needle placed through guide in the plane of the IVUS-array to improve visualization of the needle. In some embodiments, the device is used to facilitate the creation of a tract through the liver from the inferior vena cava to the portal vein using IVUS-guidance in a direct intrahepatic portocaval shunt procedure. The devices, systems, and methods can improve patient safety by decreasing the risk of off-target punctures, decrease procedure times, and allow procedures to be performed from a single access site.

3 Claims, 45 Drawing Sheets

(51) Int. Cl.
*A61B 8/08* (2006.01)
*A61B 8/00* (2006.01)
*A61M 25/10* (2013.01)

(52) U.S. Cl.
CPC ............... *A61B 8/12* (2013.01); *A61B 8/445* (2013.01); *A61B 17/3403* (2013.01); *A61M 25/10* (2013.01); *A61B 2017/3413* (2013.01)

(56) References Cited

U.S. PATENT DOCUMENTS

| | | | |
|---|---|---|---|
| 6,306,097 B1 | 10/2001 | Park et al. | |
| 6,368,280 B1* | 4/2002 | Cermak | A61B 8/0833 600/459 |
| 6,461,296 B1* | 10/2002 | Desai | A61B 8/0841 600/210 |
| 6,554,801 B1 | 4/2003 | Steward et al. | |
| 2003/0073908 A1* | 4/2003 | Desai | A61B 8/0841 600/464 |
| 2005/0203413 A1* | 9/2005 | Fichtinger | A61B 8/0833 600/461 |
| 2006/0241368 A1* | 10/2006 | Fichtinger | A61B 5/055 600/407 |
| 2007/0179380 A1 | 8/2007 | Grossman | |
| 2010/0063392 A1 | 3/2010 | Nishina et al. | |
| 2013/0211176 A1* | 8/2013 | Habib | A61B 18/1492 600/3 |
| 2013/0296699 A1 | 11/2013 | Deckman et al. | |

FOREIGN PATENT DOCUMENTS

| | | |
|---|---|---|
| JP | 2002-514111 | 5/2002 |
| JP | 2006-101915 | 4/2006 |
| WO | WO 93/08738 | 5/1993 |
| WO | WO 96/19256 | 6/1996 |
| WO | WO 98/46119 | 10/1998 |
| WO | WO 99/49910 | 10/1999 |
| WO | WO 2007/121078 | 10/2007 |
| WO | WO 2008/046031 | 4/2008 |

OTHER PUBLICATIONS

Office Action, dated Jun. 19, 2018 for Japanese Application No. JP 20006-553606.
Office Action dated Feb. 5, 2019 in Japanese Patent Application No. 2016-533606 filed May 19, 2016.

* cited by examiner

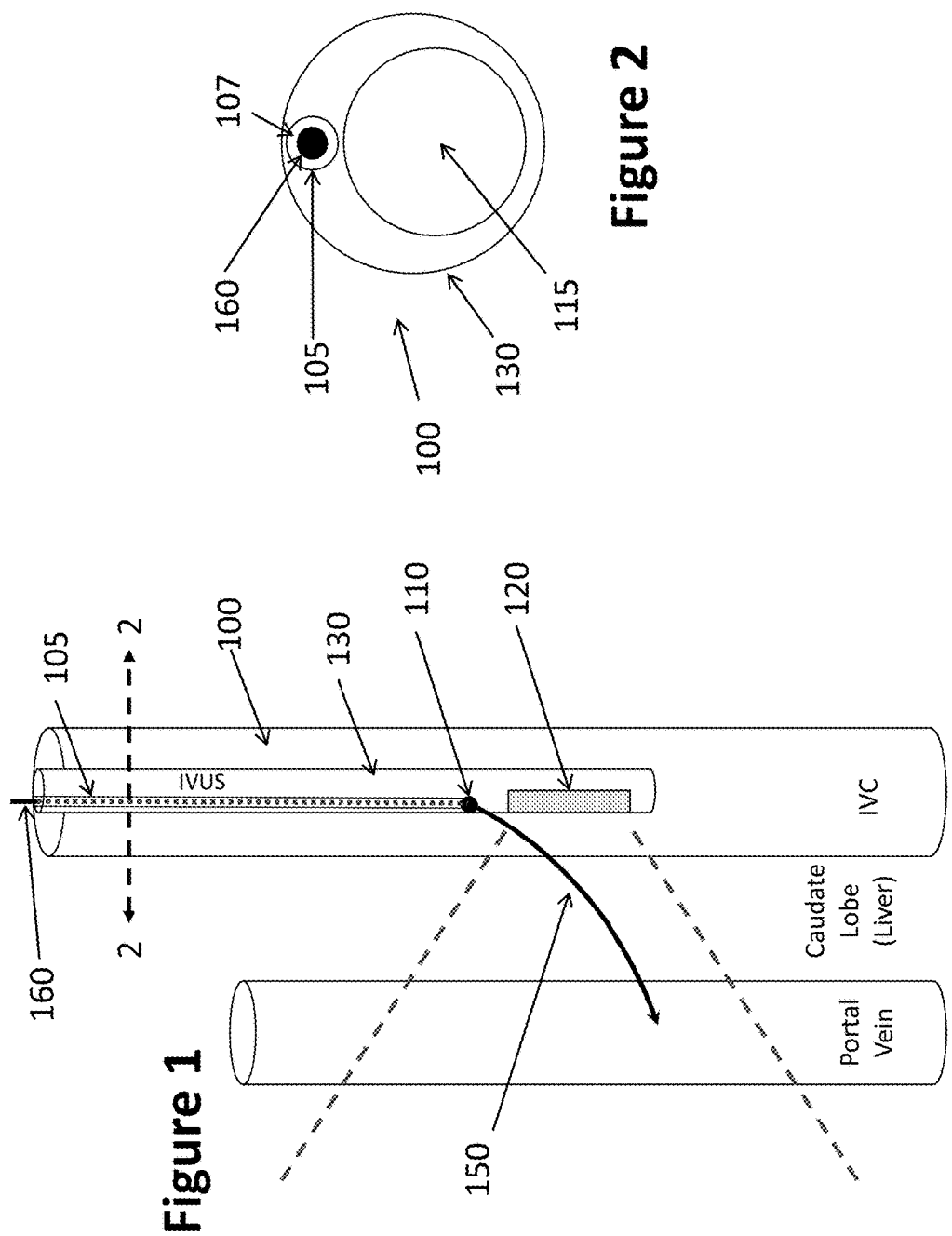

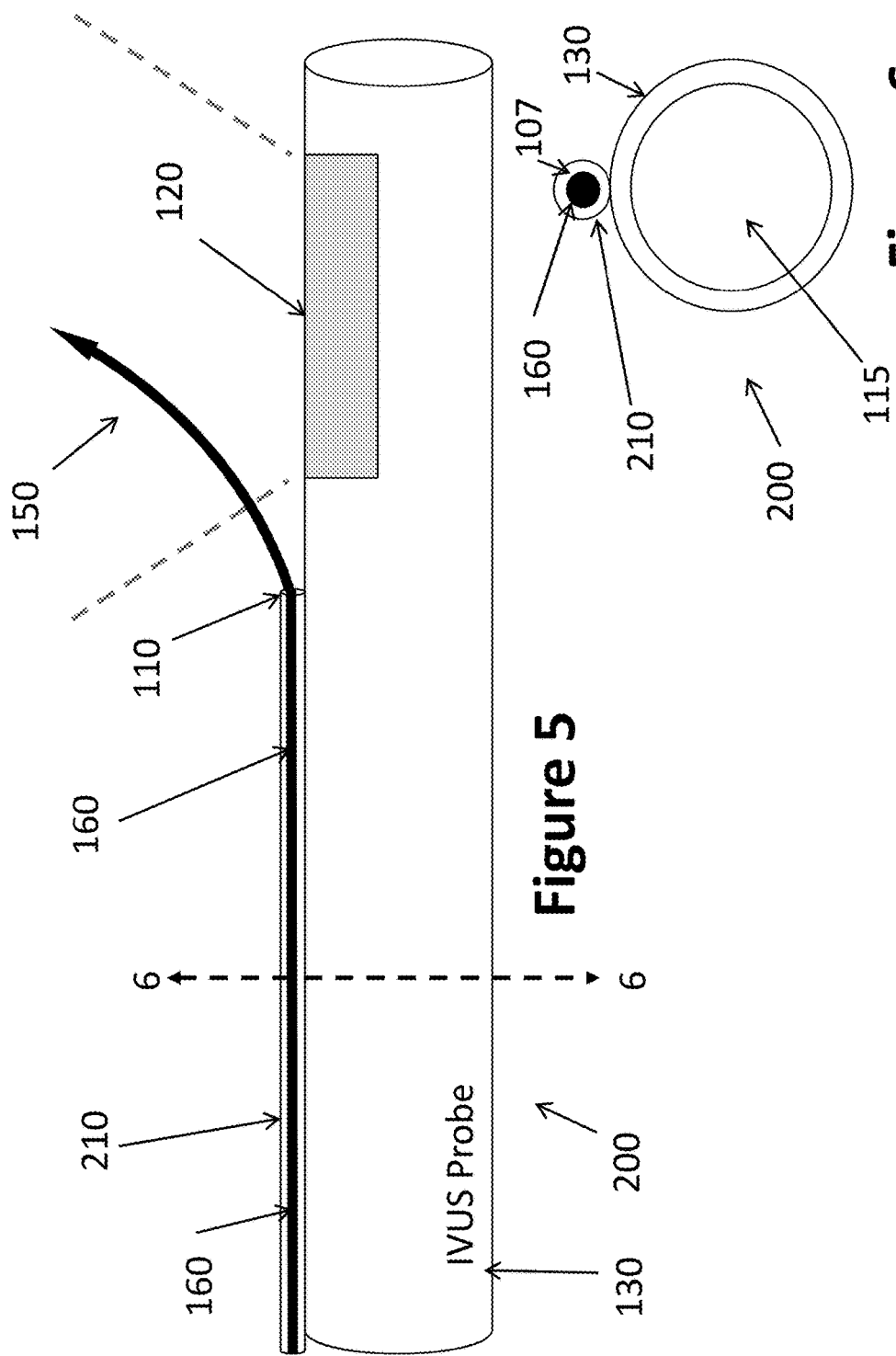

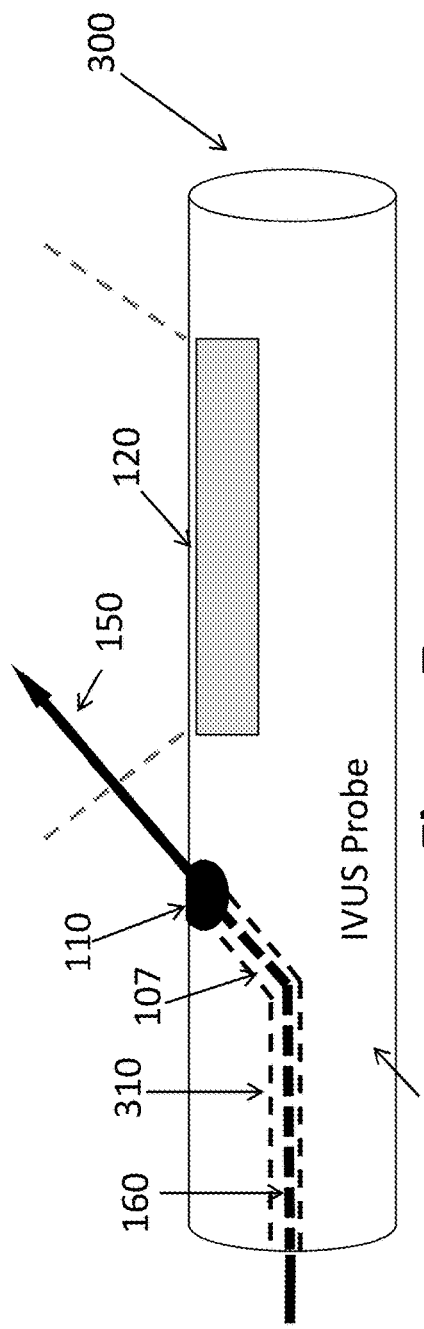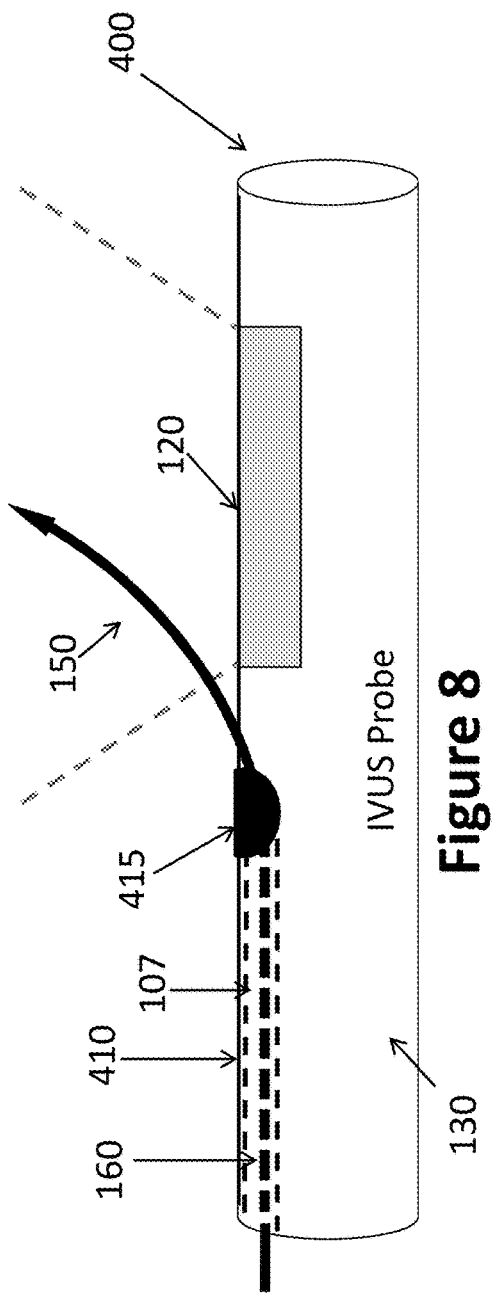

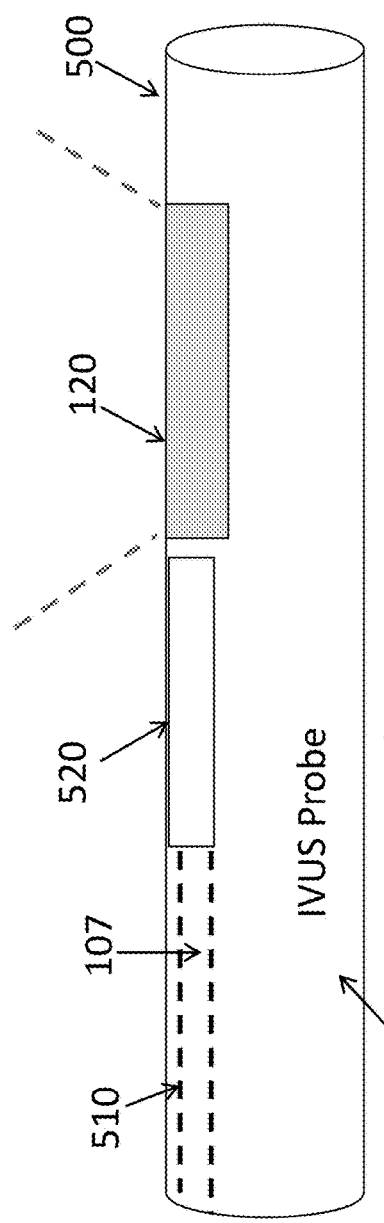
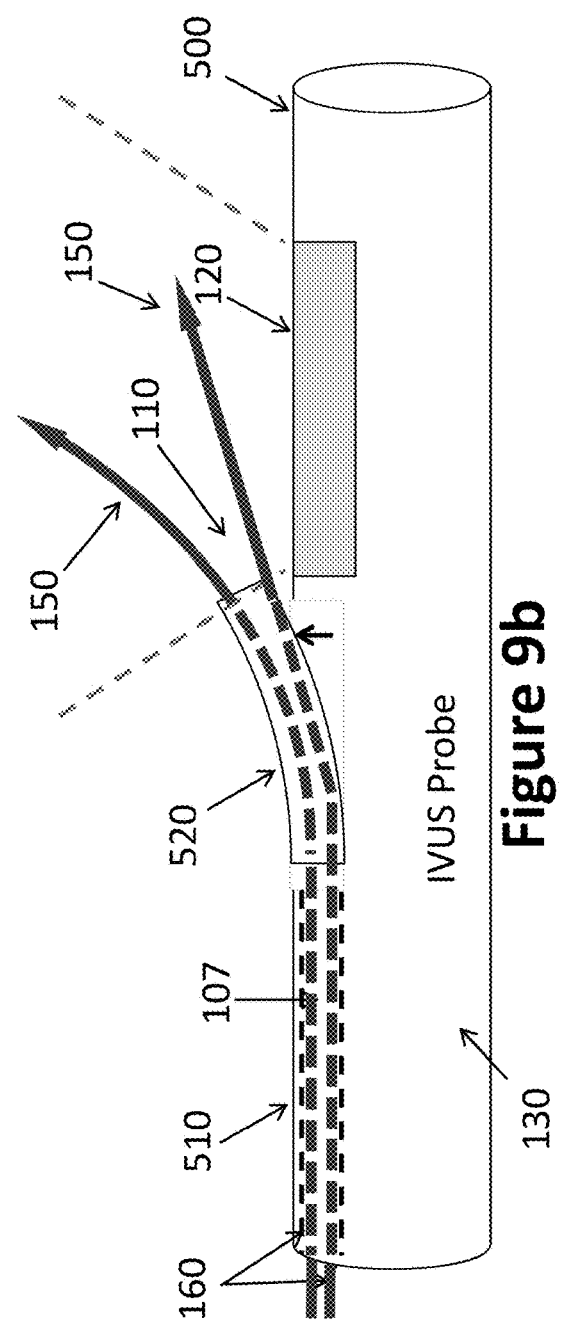
Figure 9a
Figure 9b

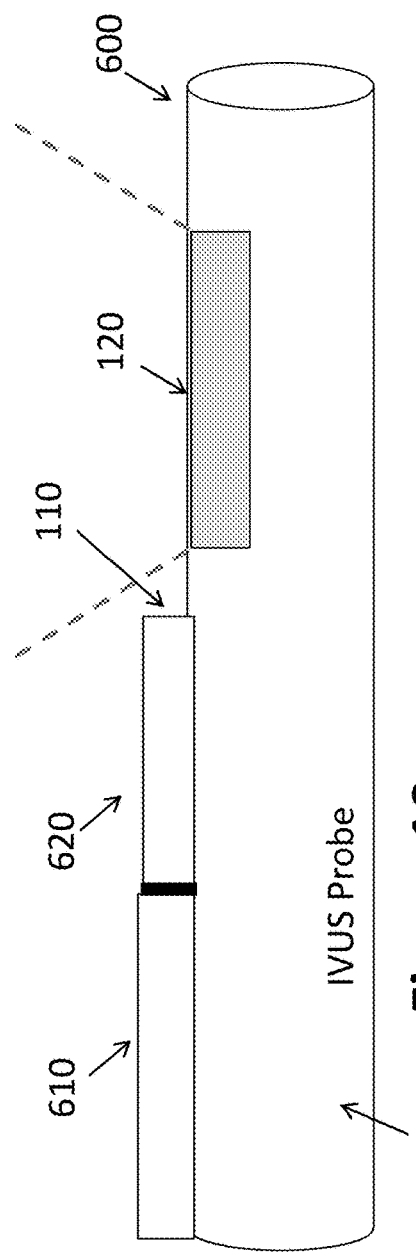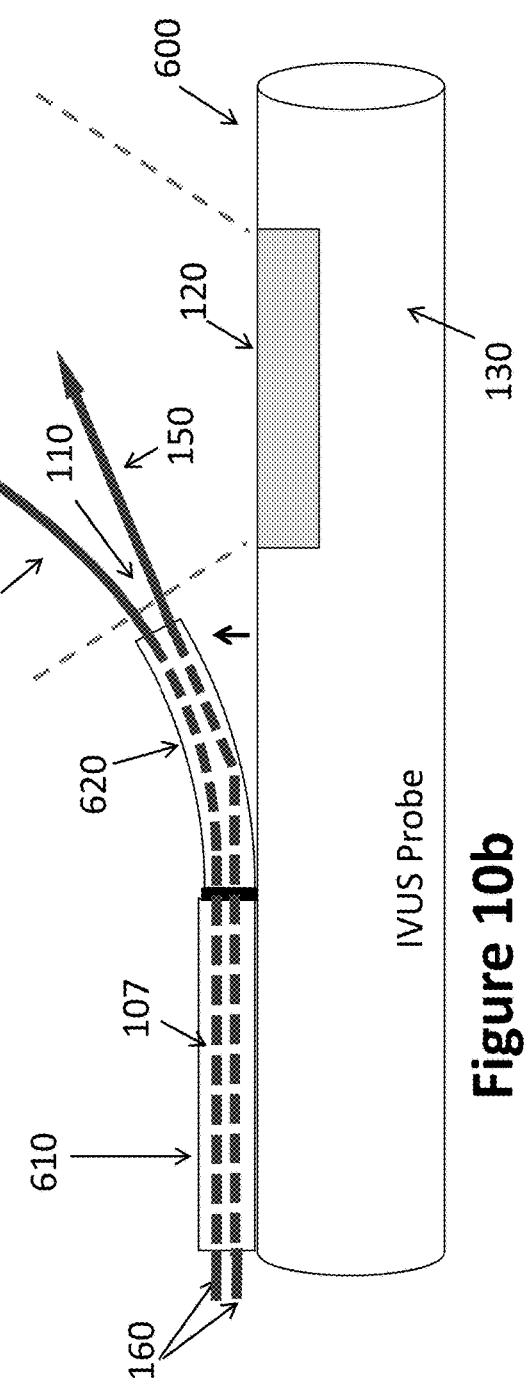

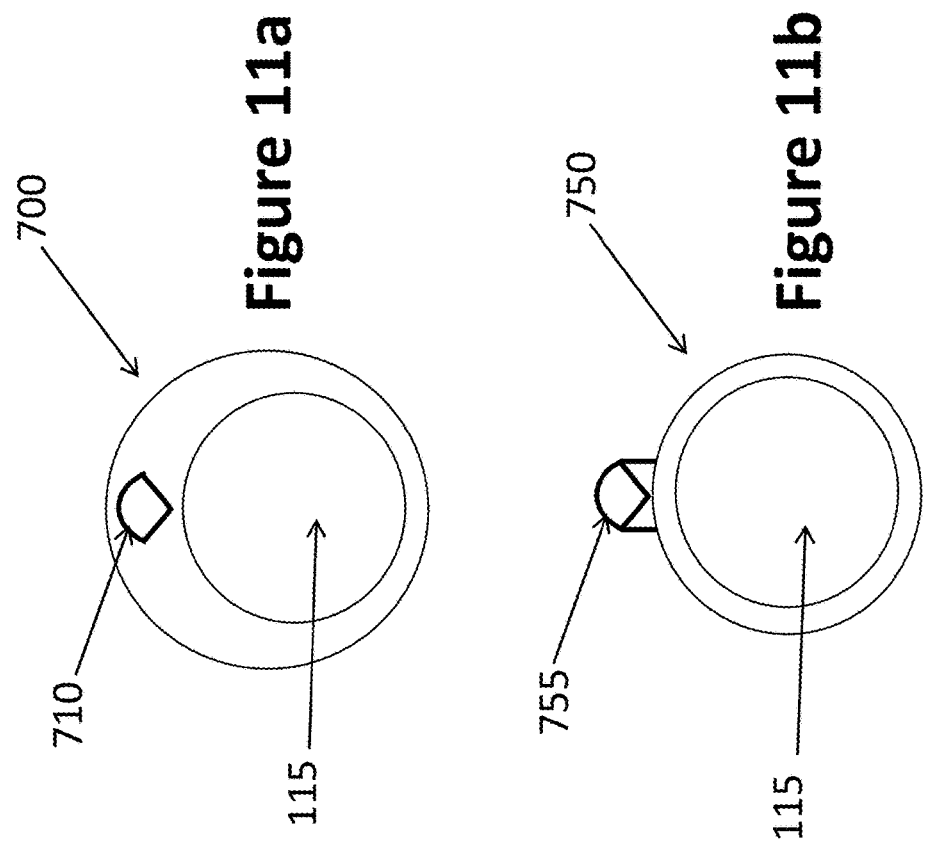

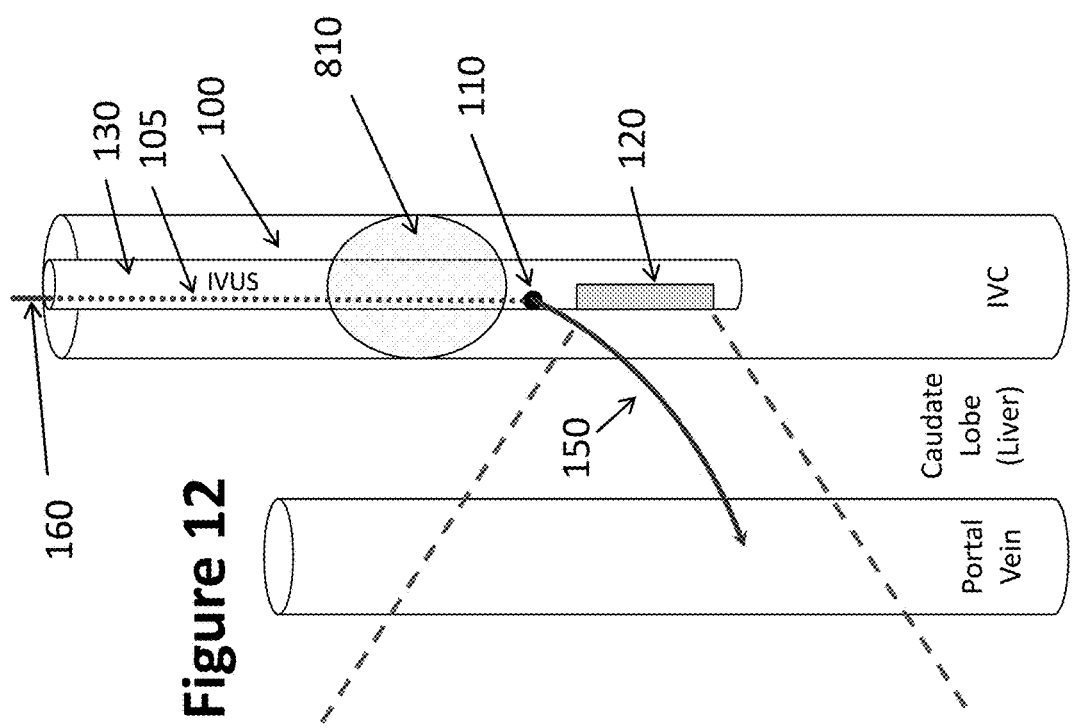

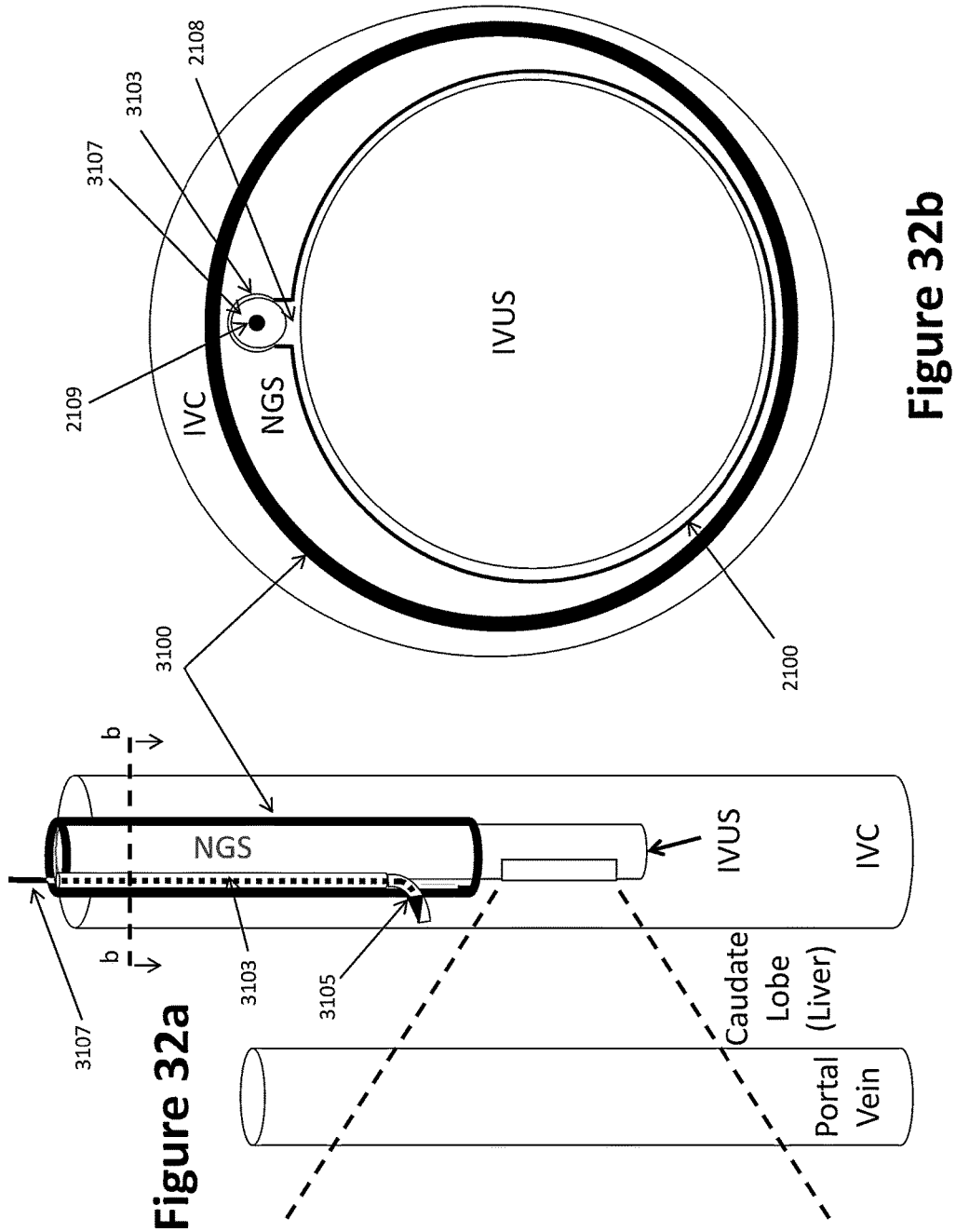

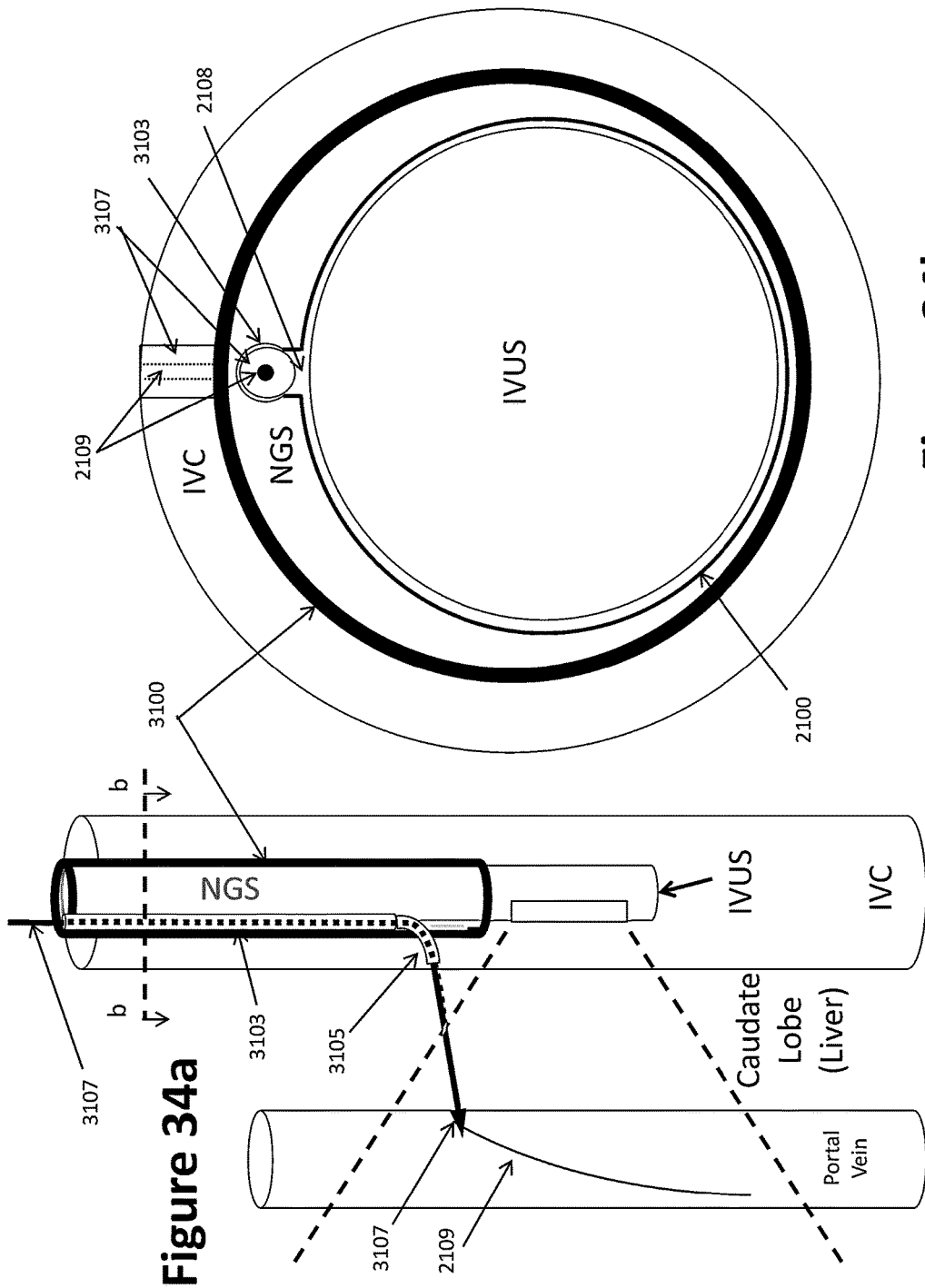

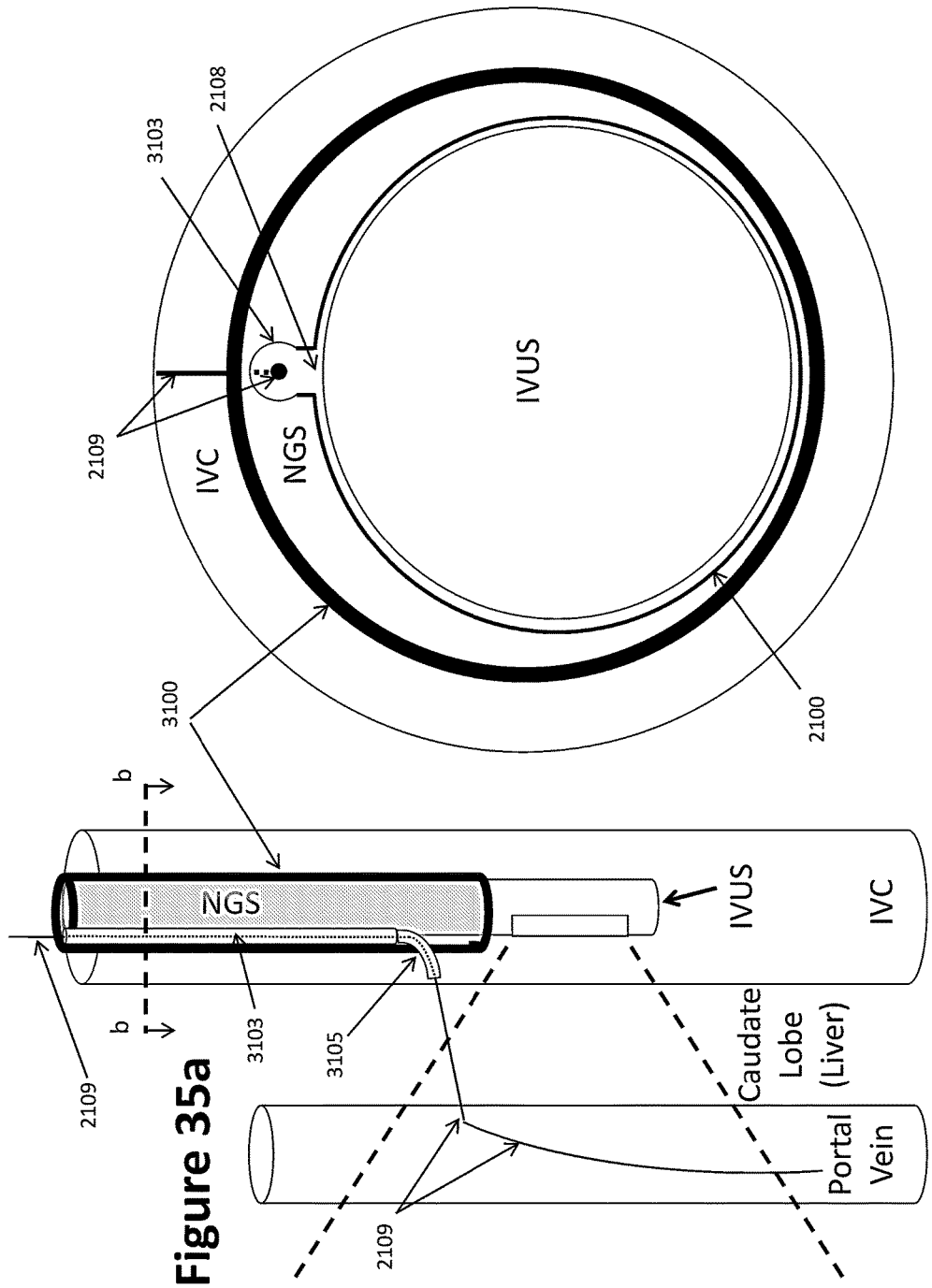

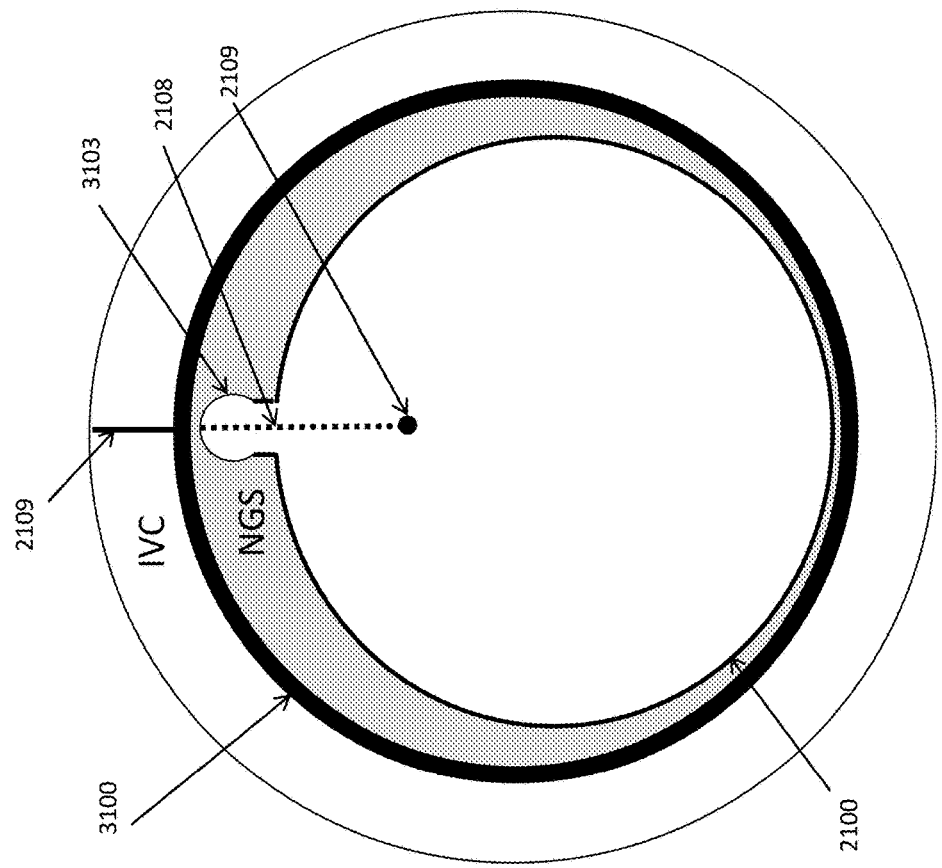
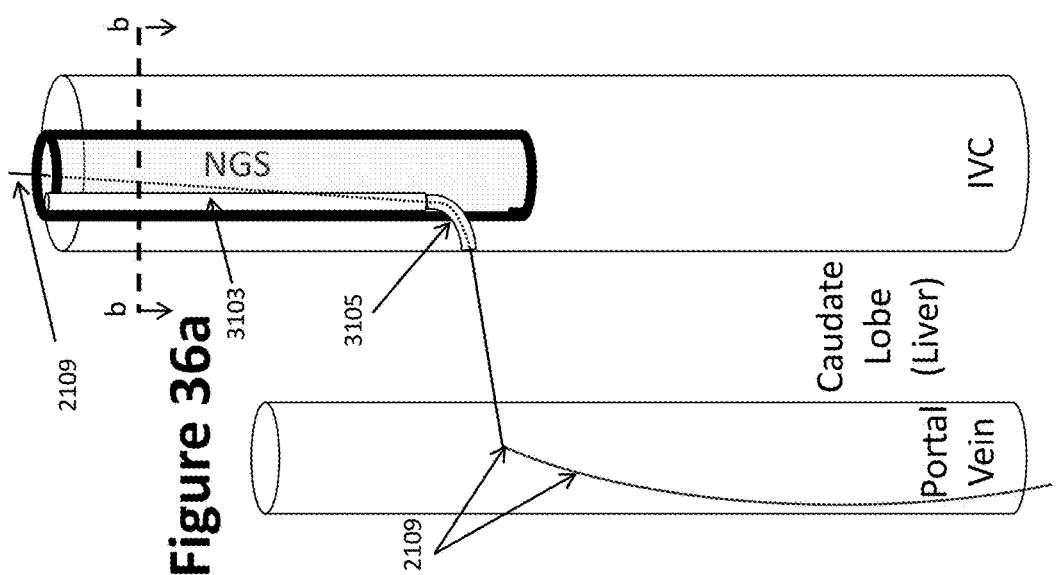
Figure 36b
Figure 36a

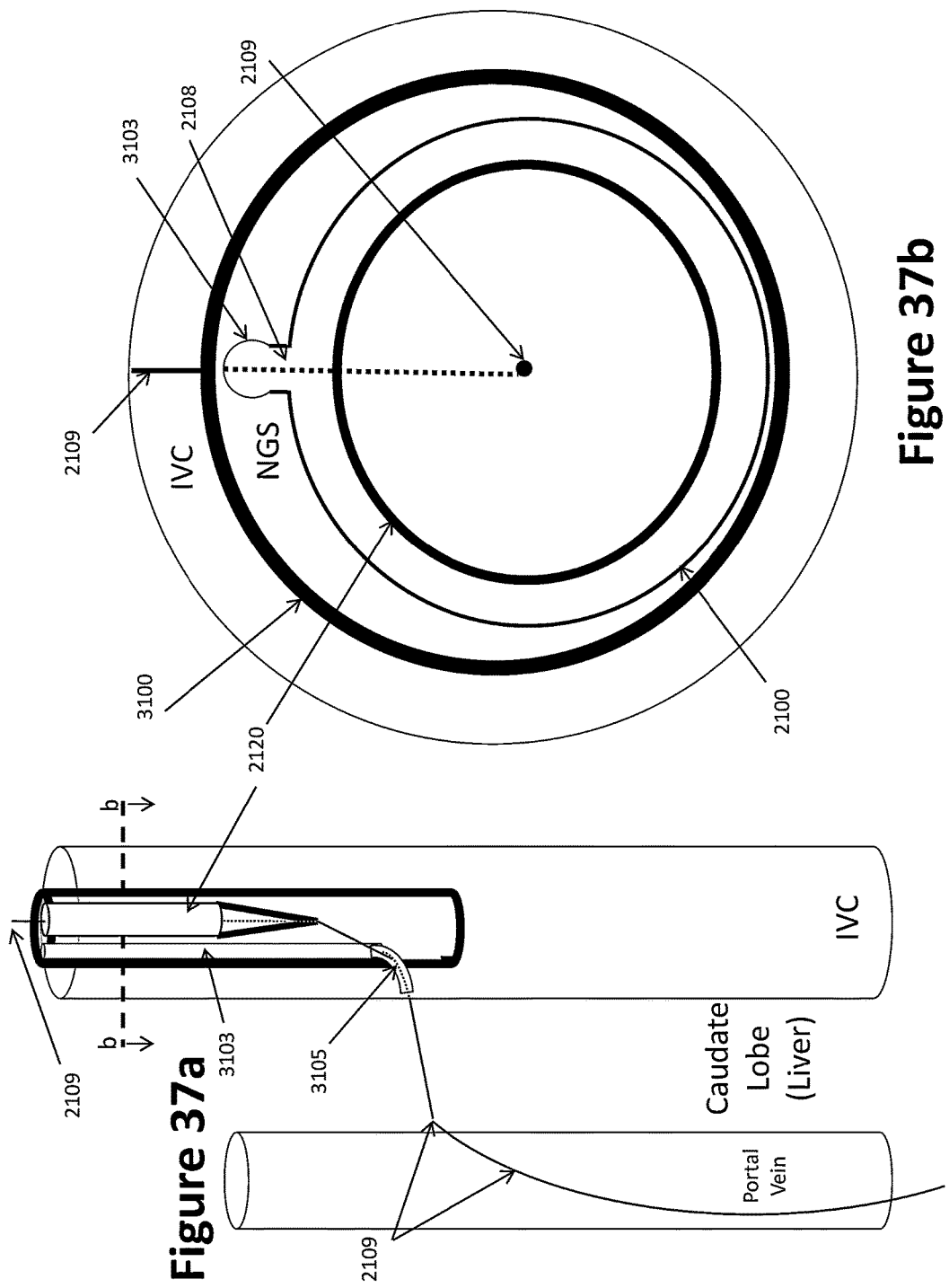

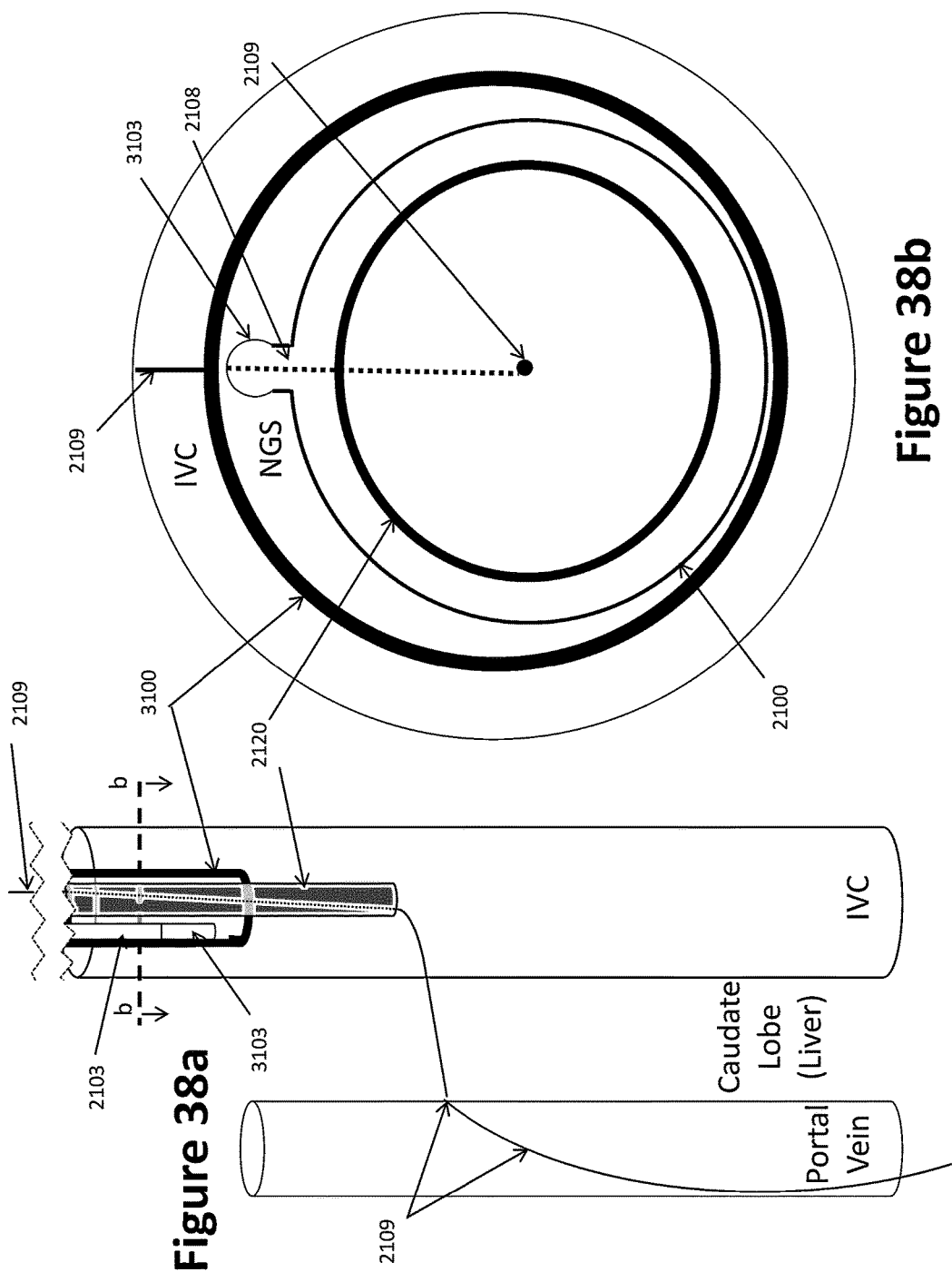

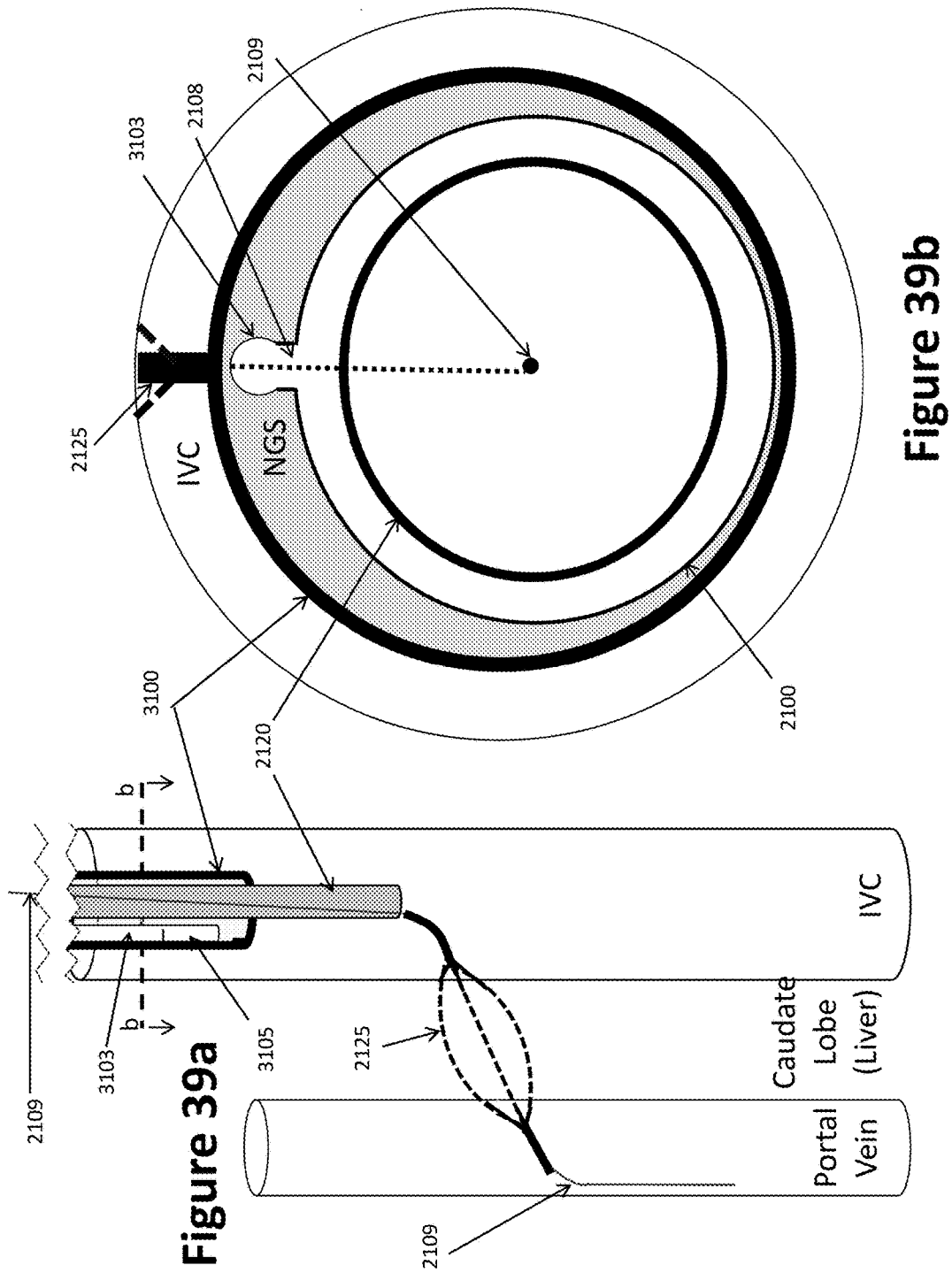

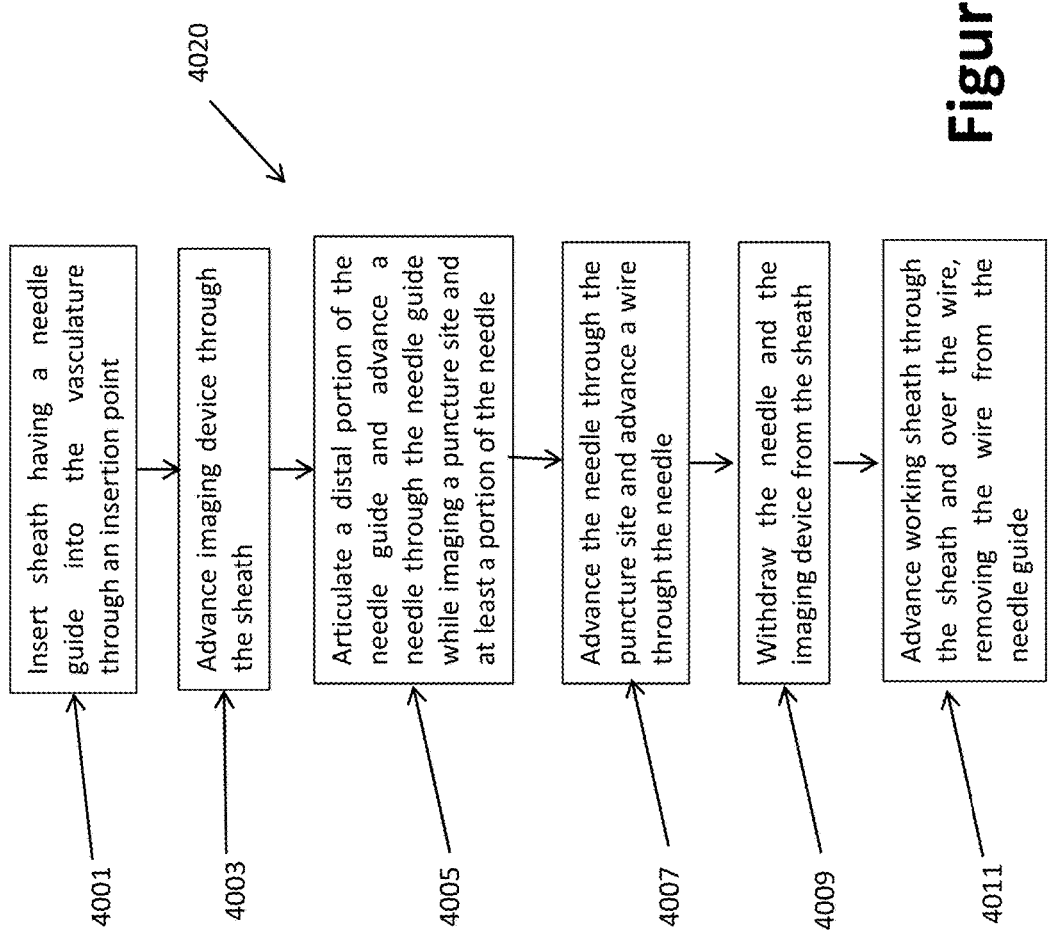

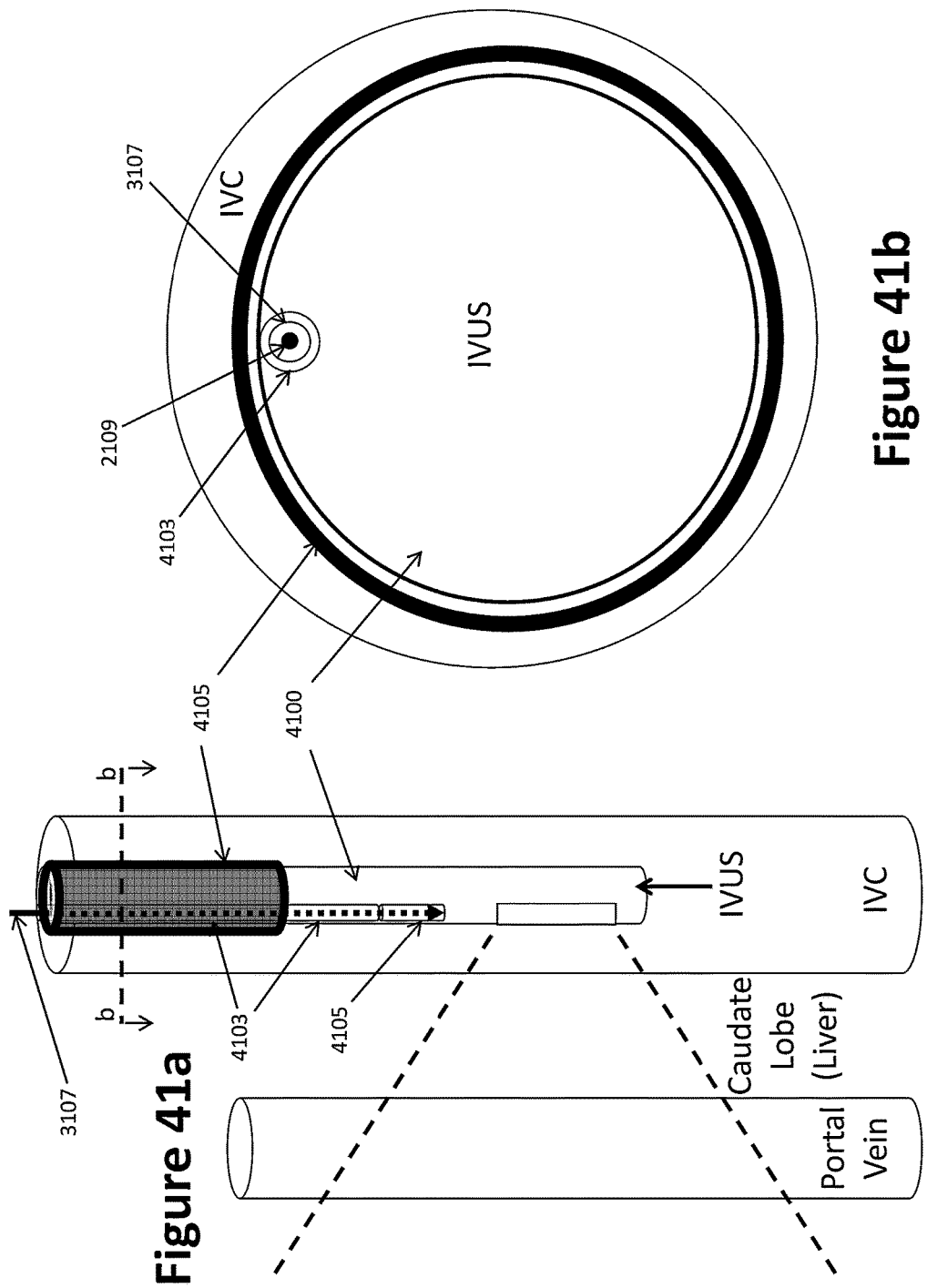

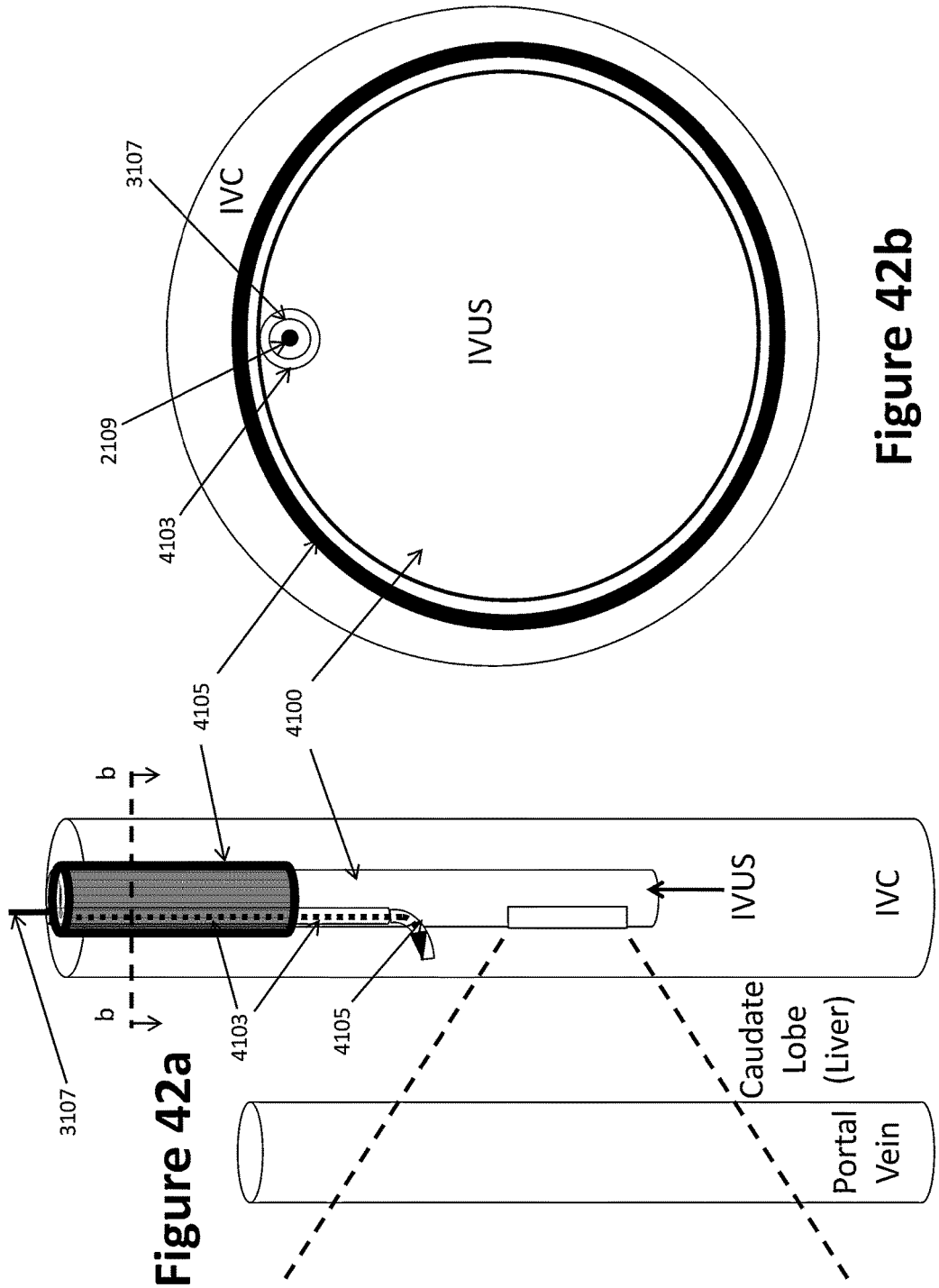

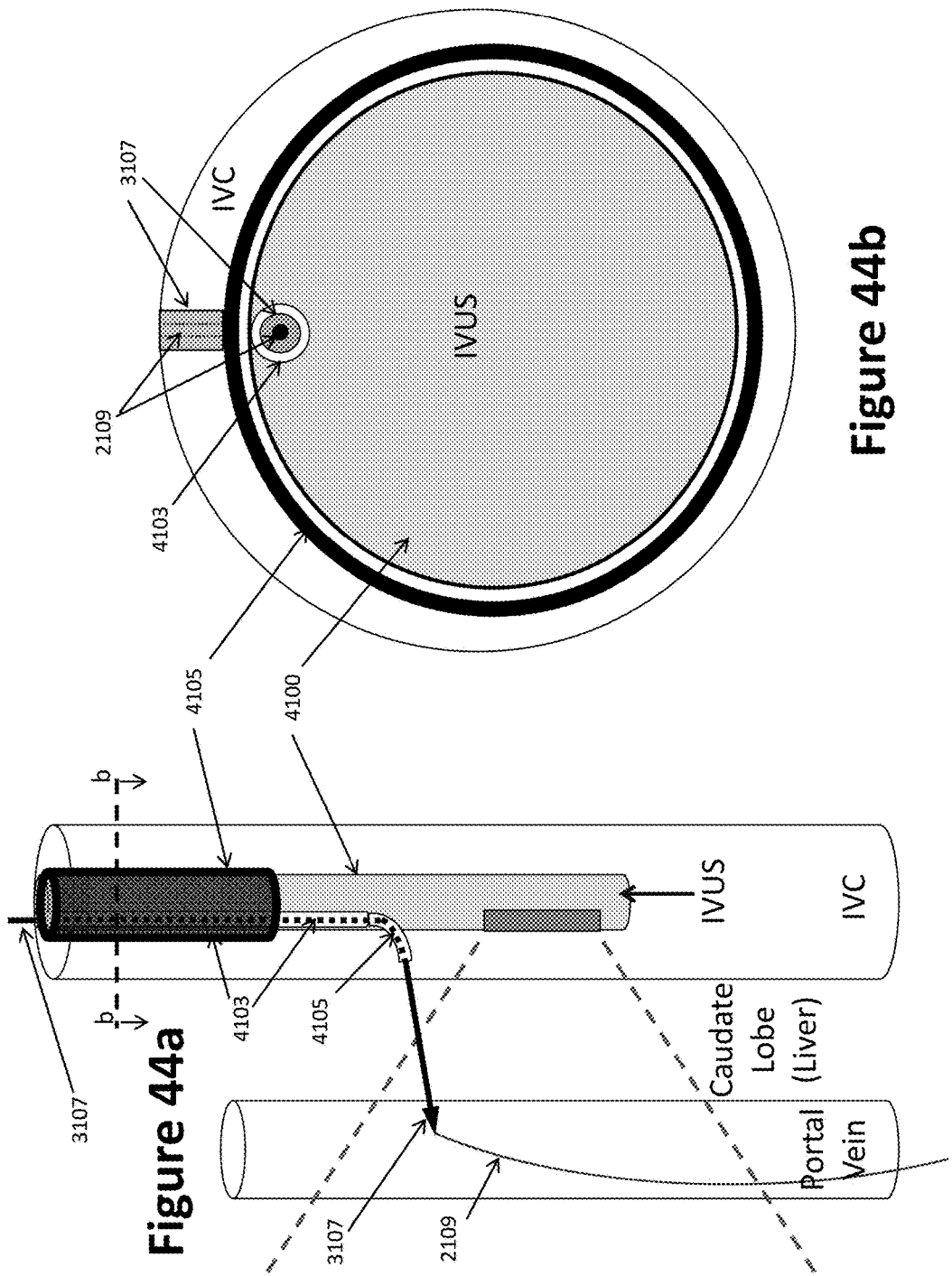

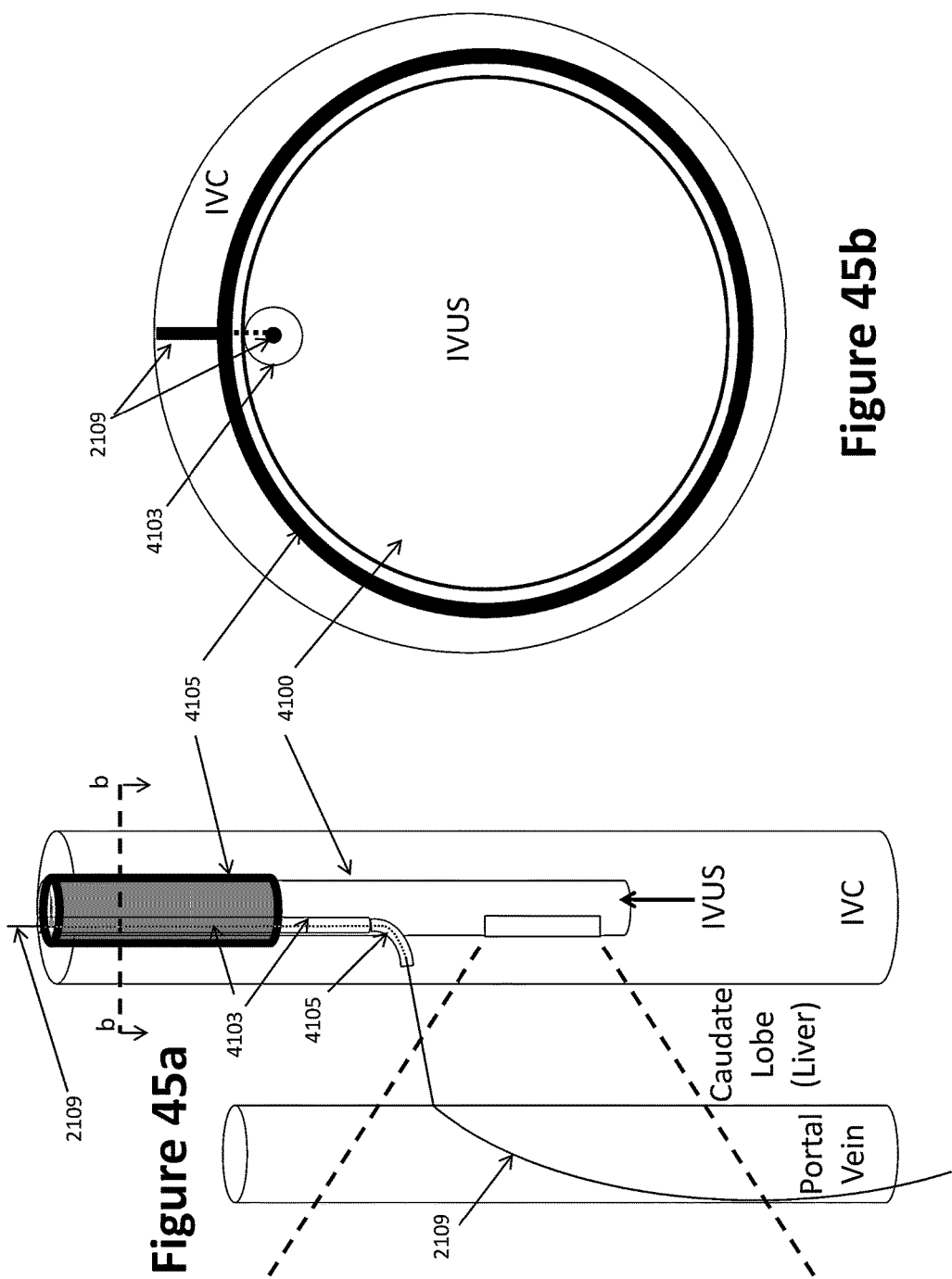

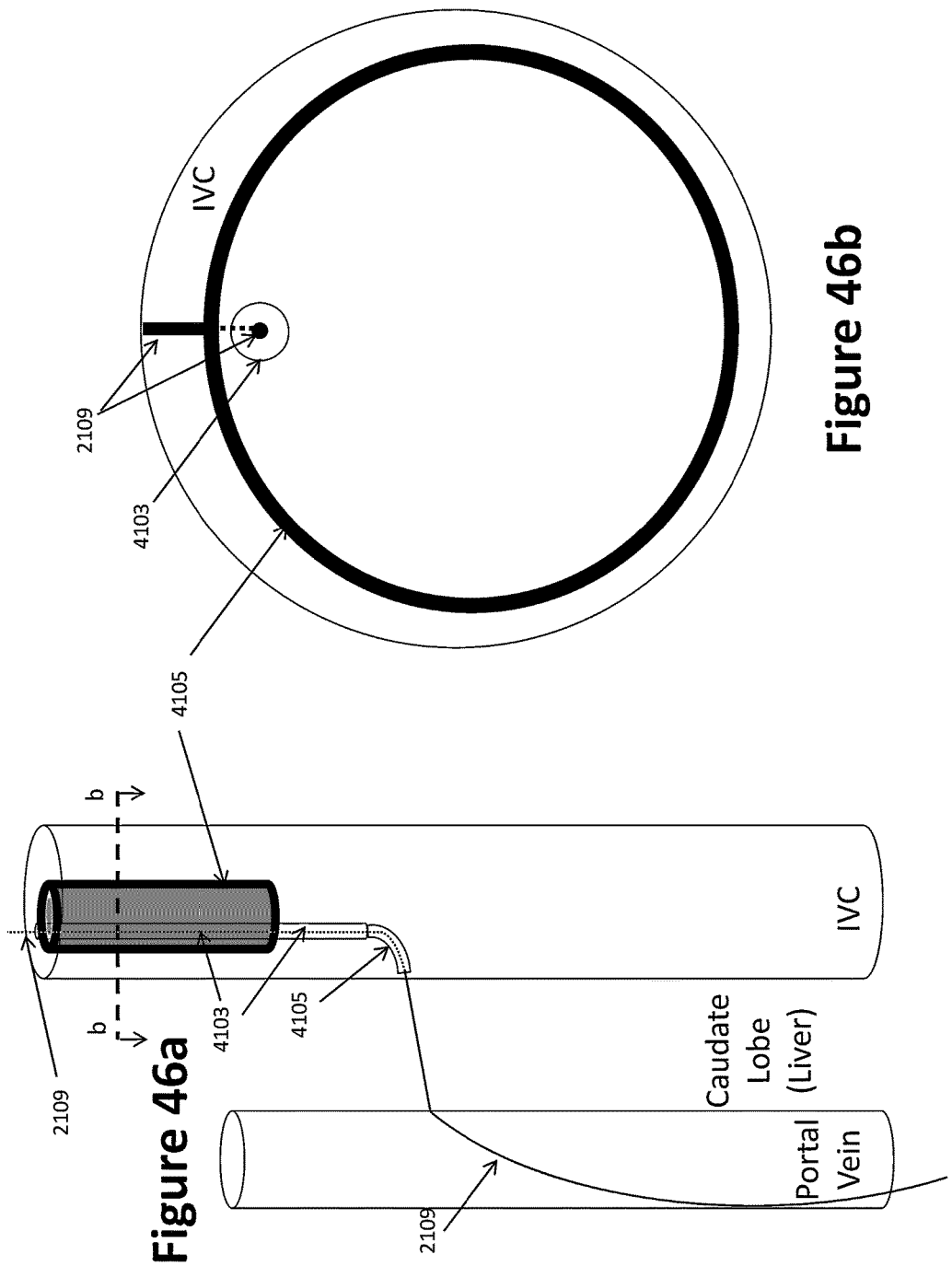

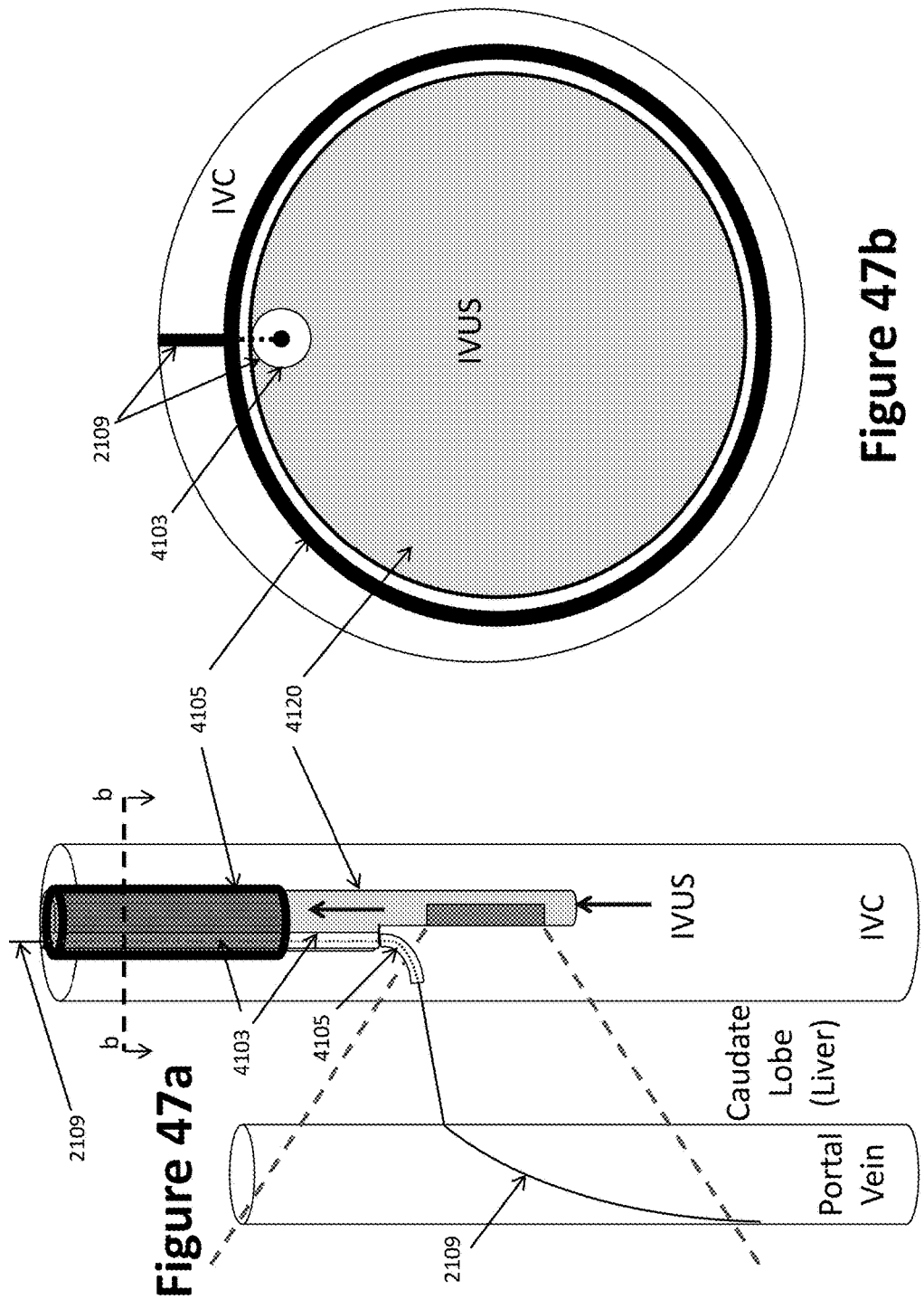

INTRAVASCULAR ULTRASOUND NEEDLE GUIDE

RELATED APPLICATIONS

This application claims priority to U.S. Provisional Patent App. No. 61/906,860, filed 20 Nov. 2013, entitled "INTRAVASCULAR ULTRASOUND NEEDLE GUIDE," which is hereby incorporated by reference in its entirety.

BACKGROUND

Field

The present disclosure relates generally to devices, systems, and methods using needle guides and ultrasonic imagery in minimally-invasive surgical procedures. More specifically, this disclosure relates to an ultrasonic imaging device and needle guide configured to improve visualization of the needle and facilitate accurate punctures.

Description of the Related Art

A medical procedure may utilize intravascular ultrasound ("IVUS"). IVUS can involve a catheter having an ultrasound probe attached to the distal end of the catheter or a cylindrically-shaped probe with an ultrasound array positioned at the distal end to be used for intravascular ultrasound imaging. IVUS can be used to visualize the interior of portions of the arterial or venous system. In this way, veins and/or arteries may be examined for atheroma, plaque, calcific material, and the like. IVUS may also be used to examine structures adjacent to the blood vessel, such as adjacent organs or the location of adjacent blood vessels.

SUMMARY

The devices, systems, and methods of the present disclosure have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Embodiments," one will understand how the features of this disclosure provide several advantages over other IVUS systems, methods, and devices.

One aspect is an intravascular ultrasound device that has a needle guide, either intrinsic to an IVUS probe or as an extrinsic attachment to the probe, to be used in performing minimally invasive image-guided surgical procedures. Some embodiments include a sheath or support structure through which an IVUS catheter can pass. In some embodiments, the sheath or support structure includes a needle guide. In some implementations, a needle having a pre-curved distal portion is inserted through the needle guide. In other implementations, a straight needle is used with a needle guide that has an articulating distal portion. In other implementations, a needle having an articulating distal portion is inserted into the needle guide. In some implementations, the needle includes a lumen running therethrough. A wire may be placed within the lumen.

In some embodiments, the intravascular ultrasound device includes a means for stabilizing the probe within a vessel lumen. The means for stabilizing may be intrinsic to the IVUS probe. In other embodiments, the means for stabilizing is an attachment to the probe, an attachment to a catheter, or incorporated into a guide sheath. The means for stabilizing may comprise one or more inflatable balloons. The means may comprise one or more rigid guidewires.

Another aspect is needle guide configured to keep a needle in the plane of the visualization path of an IVUS probe. Another aspect is a device having a flexible curved needle configured to straighten when advanced through a needle guide. The needle may be configured such that the needle returns to a predetermined curved shape when the needle exits a distal end of the needle guide. The needle guide may be intrinsic to the IVUS probe. In some embodiments, the needle guide is an attachment to the probe. In some embodiments, the IVUS guide is passed through a guide-sheath. The sheath may comprise a hemostatic vascular sheath. The sheath may include a needle guide, a lumen for the IVUS catheter, and/or one or more stabilization balloons.

Another aspect is a system for performing a medical procedure. The system may comprise a catheter having a proximal end and a distal end comprising an ultrasonic probe. A puncture assembly may comprise a needle guide having a lumen extending therethrough. The lumen may have a proximal opening, a distal opening, and a flexible needle disposed therein. The puncture assembly may be configured to direct a distal end of the needle into a visualization area of the ultrasonic probe. The needle guide may have a distal potion configured to bend away from the catheter. The flexible needle may have a distal potion configured to bend away from catheter. The distal opening may be configured to deflect the distal end of the needle away from the catheter. The needle guide and the needle may have cross-sectional shapes so that the needle is inhibited from rotation within the needle guide.

Another aspect is a system for performing a medical procedure comprising a sheath having at least a first lumen and a second lumen extending therethrough. The first lumen may be configured to receive a catheter having a proximal end and a distal end comprising an ultrasonic probe. The second lumen may be configured to receive a flexible needle. The needle may have an internal lumen for passage of a guidewire extending therethrough. In some embodiments, the needle is advanced in unison with an internal guidewire extending therethrough. In other embodiments, the needle is advanced first, followed by an internal guidewire that is advanced through the internal lumen of the needle.

A channel may connect the first lumen with the second lumen. The channel may be sized and shaped so as to allow the wire but not the needle to pass therethrough. The needle guide and the needle may be shaped such that the needle is prevented from rotating within the needle guide. The second lumen may have a distal portion configured to bend away from the catheter.

Another aspect is a surgical method of treatment comprising advancing a sheath into the vasculature of a patient. The sheath may have a first lumen and a second lumen extending therethrough. The first lumen and the second lumen may be connected by a passageway. The method may include advancing a needle through the first lumen. The needle may have a lumen for an internal wire to pass through. The method may further include advancing an ultrasonic imaging device through the second lumen and advancing the needle out of a distal opening of the first lumen and into a visualization area of an ultrasonic device. An internal wire may be advanced through the needle. The method may also include withdrawing the needle and the ultrasonic device, and advancing a working sheath through the second lumen and over the internal wire to pull the internal wire through the passageway and into the second lumen. The method may include articulating at least a portion of the needle to a position that is not parallel with respect to a longitudinal axis of the second lumen. The method may include displaying an image of the needle advancing out of the distal opening of the first lumen. The method may include advancing a collapsible stent over the internal wire and through the working sheath. The method may include separating the needle from the internal wire. In some aspects, the method includes advancing an angioplasty balloon and an expandable stent over the internal wire and through the working sheath. The method may include removing the needle over the internal wire.

BRIEF DESCRIPTION OF THE DRAWINGS

These and other features, aspects, and advantages of the invention disclosed herein are described below with reference to the drawings of certain embodiments, which are intended to illustrate and not to limit the invention. Additionally, from figure to figure, the same reference numerals have been used to designate the same components of an illustrated embodiment. The following is a brief description of each of the drawings.

FIG. 1 is a schematic illustration of an embodiment IVUS probe having a needle guide. As shown, the needle guide extends through an internal portion of the IVUS probe.

FIG. 2 is a cross-sectional view of the device of FIG. 1 taken about the line 2-2.

FIG. 5 is an enlarged side view of the device of FIG. 4.

FIG. 6 is a cross-sectional view of the device of FIG. 5 taken about the line 6-6.

FIG. 7 is an enlarged side view of another embodiment of an IVUS probe having a needle guide. The embodiment is similar to that of FIG. 1, except that the needle guide has a distal portion that extends away from the interior of the IVUS probe.

FIG. 8 is an enlarged side view of another embodiment of an IVUS probe having a needle guide. The embodiment is similar to that of FIG. 1, except that the needle guide has an angled or curved exit port that may deflect a needle away from the IVUS probe.

FIG. 9a is an enlarged side view of another embodiment of an IVUS probe having a needle guide. The embodiment is similar to that of FIG. 1, except that the needle guide includes a distal portion that may move away from the body of the IVUS probe. As shown in FIG. 9a, the distal portion is in a down position and at least partially within the body of the IVUS probe.

FIG. 9b is a side view of the device of FIG. 9a. As shown in FIG. 9b, the distal portion of the needle guide is angled away from the body of the IVUS probe.

FIG. 10a is an enlarged side view of another embodiment of an IVUS probe having a needle guide. The embodiment is similar to that of FIGS. 9a and 9b, except that the needle guide is coupled to an exterior surface of the IVUS probe. As shown in FIG. 10a, the distal portion of the needle guide is in a down position.

FIG. 10b is a side view of the device of FIG. 10a. As shown in FIG. 10b, the distal end of the needle guide has been articulated away from the body of the IVUS probe.

FIGS. 11a and 11b are cross-sectional views of other embodiments of an IVUS probe having a needle guide. These embodiment are similar to that shown in FIGS. 2 and 6, except that the cross-section of the needle guides are shaped to prevent rotation of a needle inserted into the needle guide with respect to the IVUS probe.

FIG. 12 is a schematic illustration of another embodiment of an IVUS probe having a needle guide. The embodiment is similar to that of FIG. 1 but it includes an inflatable balloon.

FIGS. 32a and 32b are the same as FIGS. 31a and 31b except that the distal end of the needle guide is articulated away from the sheath.

FIGS. 34a and 34b are the same as FIGS. 33a and 33b except that guidewire is further advanced through the needle and further into the portal vein.

FIGS. 35a and 35b are the same as FIGS. 34a and 34b except needle is removed.

FIGS. 36a and 36b are the same as FIGS. 35a and 35b except that the IVUS probe is removed. With the needle and the IVUS probe removed, the internal guidewire may pass from the needle guide channel into the central lumen of the sheath.

FIGS. 37a and 37b are the same as FIGS. 36a and 36b except that a working sheath is advanced over the wire and through the sheath. Advancing the working sheath over the wire may further pull the wire into the central lumen of the sheath.

FIGS. 38a and 38b are the same as FIGS. 37a and 37b except that the distal end of the needle guide is moved to an unarticulated position and the sheath is partially withdrawn to further expose the working sheath.

FIGS. 39a and 39b are the same as FIGS. 38a and 38b except that a balloon stent is advanced over the wire and inflated to form a shunt between the inferior vena cava and the portal vein.

FIG. 40 is a flow diagram illustrated a method of preforming a surgical procedure according to one embodiment.

FIG. 41a shows another embodiment of IVUS probe having a needle guide. The embodiment is similar to that of FIG. 31a except that the needle guide having an articulating distal end is coupled to the IVUS probe.

FIG. 41b is a schematic cross-sectional illustration of FIG. 41a taken about the line b-b, through the inferior vena cava but not including the portal vein.

FIGS. 42a and 42b are the same as FIGS. 41a and 41b except that the distal end of the needle guide is articulated away from the sheath.

FIGS. 44a and 44b are the same as FIGS. 43a and 43b except that guidewire is further advanced through the needle and further into the portal vein.

FIGS. 45a and 45b are the same as FIGS. 44a and 44b except needle is removed.

FIGS. 46a and 46b are the same as FIGS. 45a and 45b except that the IVUS probe is removed.

FIGS. 47a and 47b are similar to FIGS. 45a and 45b except that the IVUS probe has a slightly different configuration that may facilitate the separation and removal of the IVUS probe from the needle guide.

DETAILED DESCRIPTION OF CERTAIN EMBODIMENTS

Figure 3A:
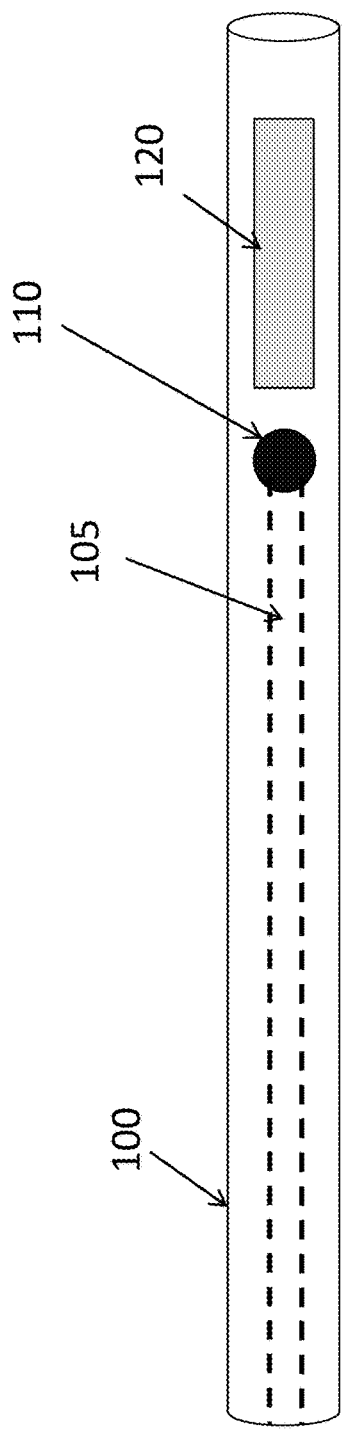
FIG. 3a is a top view of the device of FIG. 1 with the needle removed.

The following description and examples illustrate preferred embodiments of an intravascular ultrasound needle guide system disclosed in the context for use in medical procedures. The following description and the accompanying figures, which describe and show the preferred embodiments, are made to demonstrate several possible configurations that a visually guided needle and/or IVUS needle guide system can take to include the various disclosed aspects and features.

The illustrated embodiments are shown in use with an IVUS probe having an ultrasound array at or near the distal end of the probe. However, the illustration of devices in this context is not intended to limit the disclosed aspects and features to the specified embodiment or to usage only with the illustrated components and procedures. For example, the disclosed embodiments can be used with various imaging techniques known in the art. Those of skill in the art will recognize that the disclosed aspects and features are not limited to any particular embodiment of an IVUS system which can include one or more of the inventive aspects and features herein described.

The systems, methods, and devices described herein are especially adapted for use in guided minimally invasive surgical procedures. Each embodiment disclosed herein can serve the important purpose of keeping a needle in the plane of an IVUS array, thus facilitating visualization of the needle and to ensure accurate placement of the needle. The embodiments provide the benefits of decreasing the risk of off-target punctures, decreasing the operator learning curve and procedure times, and can allow for many procedures to be performed from a single access site. In sum, the disclosed systems, methods, and devices can make minimally-invasive surgical procedures safer for patients and allow for procedures previously performed by other means to be performed using IVUS-guidance.

While the embodiments can be used for direct intrahepatic portocaval shunt placement as described in detail below, the embodiments can also be used in other procedures that benefit from IVUS-guidance. Such procedures include, for example, liver lesion biopsies via a transjugular approach through the hepatic veins, vascular or cardiac mass biopsies, cardiac node ablation or mitral valve procedures that require crossing the interatrial septum, and liver and/or renal tumor ablation procedures.

A direct intrahepatic portocaval shunt ("DIPS") procedure is a means of creating a portosystemic shunt between the portal vein ("PV") and the inferior vena cava ("IVC"). DIPS may be used as a treatment for portal hypertension. Portal hypertension is a condition resulting from elevated blood pressure in the portal venous system. The portal venous system is comprised of the splenic vein, superior and inferior mesenteric veins, and coronary vein that converge to form the portal vein, which enters the liver. Portal hypertension has a variety of causes, the most common being cirrhosis. Symptoms of portal hypertension include upper gastrointestinal variceal bleeding, refractory ascites, and/or recurrent hepatic hydrothorax. A treatment consideration in patients with symptoms of portal hypertension is decompression of the portal venous system by creation of a portosystemic shunt.

IVUS imaging may be used in a DIPS procedure. An IVUS probe may be inserted into the IVC from right common femoral vein access. IVUS is used to image a puncture made using a needle advanced through a metal cannula inserted via the right internal jugular vein. The needle punctures through the wall of the intrahepatic segment of the IVC into the intrahepatic portion of the portal vein (usually near the bifurcation). This puncture passes through the caudate lobe of the liver. A wire may then be advanced through the needle to secure access across the tract. Then, using fluoroscopic guidance, the tract is dilated and a covered stent is placed to allow for sufficient blood flow through the shunt and to maintain shunt patency. This shunt decompresses the elevated pressure in the portal venous system, and thus stops and/or prevents variceal bleeding and stops or decreases development of ascites or hepatic hydrothorax.

It may be difficult to align the needle for puncture in the plane of the IVUS. The methods, systems, and devices disclosed herein can facilitate making this needle puncture under IVUS-guidance by keeping the needle in generally the same plane as the ultrasound. The methods, systems, and devices have one or more of the following benefits and advantages. First, they can allow for significantly improved visualization of the needle which can decrease the risk of off-target punctures. In the setting of DIPS specifically, off-target punctures can lead to arterial injury and/or liver capsule perforation, which can lead to bleeding complications, including hemoperitoneum and death. In addition, the technical difficulty of the procedure is decreased. Thus, the procedure is safer and operator learning curve times are shortened. Furthermore, the techniques and devices can allow for the entire procedure to be performed from a single access site (e.g., entering from the right internal jugular vein). The need for a separate access site in the right common femoral vein for the IVUS probe is obviated. This improvement decreases procedure time and eliminates potential complications from a second access site.

The inventions disclosed herein can also be used for other procedures that benefit from IVUS-guidance. Again, the benefits of the invention in these settings are improved visualization of the needle using IVUS, decreased the risk of off-target punctures, reduced technical difficulty resulting in reduced procedure times, and elimination of the need for additional access sites currently required for these procedures. Pertaining specifically to liver lesion biopsies and vascular or cardiac mass biopsies, the inventions can make procedures feasible using IVUS-guidance that previously were not. Liver lesions ordinarily are biopsied transhepatically under ultrasound guidance with puncture of the liver capsule, which increases the risk of intraperitoneal hemorrhage. Biopsy may not even be possible in patients with uncorrectable coagulopathies. Vascular and cardiac masses are typically biopsied surgically, which also carries risk of bleeding, as well as risks of general anesthesia. Accordingly, the inventions disclosed herein may aid with biopsy procedures as well.

More specifically, in some embodiments, the device comprises a needle guide that is intrinsic to an IVUS probe or is an attachment to the probe. The needle guide can extend along the length of the probe with a proximal opening for insertion of a needle, and a distal opening for exiting of the needle. The guide can keep the inserted needle in line with the IVUS-array when the end of the needle is advanced through the distal opening.

In some embodiments, the device includes a relatively straight guide that could be used in combination with a curved flexible needle such that the needle would be able to straighten to pass through the needle guide, and would then reassume its predetermined curved shape once it is passed through the distal opening of the guide. Various flexible needles having different degrees of curvature may be used. In this way, needle punctures can be made at different angles depending on what is desired for the procedure.

In some embodiments, the device includes a "pop-up" or articulating guide allowing the probe to be safely placed and positioned intravascularly while the guide is "down." Once the site of puncture is determined, the pop-up or articulating guide may be activated and at least a portion of the guide may move away from the probe and/or catheter. In this way, a straight flexible needle may be advanced through the needle guide to make a puncture at an angle determined by the pop-up guide. The angle of the pop-up guide may be adjusted such that punctures can be made at different angles depending on what is desired for the procedure. A curved flexible needle can be used instead of a straight flexible needle to further increase the angle for puncture.

In some embodiments, the device may include a needle guide having a distal portion that is angled away from the catheter and/or probe. Thus, a straight flexible needle can be advanced through the guide and can exit at an angle determined by the angle of the distal portion of the guide. The various guide assemblies disclosed herein may be either intrinsic to the IVUS probe or an attachment to the probe. In some embodiments, the device comprises a needle-guide that is removably attached to an IVUS probe.

In some embodiments, the device comprises a sheath having a needle guide. The needle guide may be attached to the exterior or the interior surface of the sheath. The sheath may be generally cylindrical in shape and may have a generally cylindrical lumen extending therethrough. An IVUS device may be positioned within the lumen. The sheath may also include an internal needle guide extending therethrough. For example, a generally cylindrical sheath having a generally cylindrical lumen extending therethrough may have a generally cylindrical sheath wall. The wall may include a needle guide extending therethrough. The needle guide may comprise a lumen extending through the sheath. In some embodiments the needle guide comprises a channel disposed in the sheath wall. The channel may connect with the central lumen in the sheath via a passageway.

In some embodiments, a means for stabilizing the probe within a vessel lumen may be included. In some implementations, a relatively large amount of force is required to penetrate the tissue outside of the vein in which the needle guide is positioned. Accordingly, it may be desirable to stabilize the needle guide, sheath, and/or IVUS such that the device remains in substantially the same place while the needle is advanced out of the vein and into the tissues and/or organs surrounding the vein. Stabilizing the device may increase the amount of leverage that can be applied to the needle. The stabilization could be accomplished by various structures and implementations. For example, the device may include one or more balloons coupled to the IVUS probe. In some embodiments, the device includes a balloon that is intrinsic to the IVUS probe. A balloon may be located proximal and/or distal to the distal end of the needle guide and proximal and/or distal to the IVUS. A balloon may be located proximal to the distal end of the needle guide. In some embodiments, two balloons are used. For example, one balloon may be located proximal to the distal end of the needle guide and a second balloon may be located distal to the IVUS array. In some embodiments the one or more balloons are deposed on a support structure that is coupled to the IVUS array. Other means for stabilizing the probe and/or needle guide may also be provided in combination with or instead of one or more balloons. For example, the IVUS, sheath, and/or needle guide may be configured to be advanced over a stiff guide wire to aid with stabilizing the device within a vein.

Various aspects will now be described with reference to specific forms or embodiments selected for purposes of illustration. It will be appreciated that the spirit and scope of the securement system disclosed herein is not limited to the selected forms. Moreover, it is to be noted that the figures provided herein are not drawn to any particular proportion or scale, and that many variations can be made to the illustrated embodiments. Brief introductions to some of the features, which are common to the described embodiments of the securement systems, are now described. In some embodiments, the needle guide is extrinsic to the IVUS catheter, and incorporated into a sheath—which the IVUS catheter can pass through. One or more support balloons may be incorporated into the distal end of the guide-sheath.

As described herein, some embodiments may be used in combination with various IVUS probes and/or catheters. In general, such devices employ one or more ultrasound probes attached to the distal end of a catheter. The proximal end of the catheter may be attached to computerized ultrasound equipment which allows an operator to see from inside blood vessels and into areas surrounding the blood vessel. The catheter may receive and conduct return echo information to external computerized ultrasound equipment which can construct and display real time ultrasound images.

FIG. 1 illustrates a device 100 including an IVUS probe 130 with needle guide 105 according to one embodiment. As shown, the needle guide 105 is intrinsic to the IVUS probe 130. In other words, the needle guide 105 includes a lumen 107 sized and shaped such that a needle 160 may pass through the interior of the IVUS probe 130.

FIG. 2 illustrates a cross-section of the embodiment illustrated in FIG. 1 taken about the line 2-2. While the device 100 is shown to have two lumens, one to house the IVUS components 115 and the other to house a needle 160, more lumens may be utilized. For example, in some embodiments, the device includes a lumen configured to dispense or withdraw fluid.

The needle guide 105 can keep the needle 160 in the plane of the ultrasound array 120 to improve visualization of the needle 160 and to facilitate accurate IVUS-guided punctures. The device 100 can also allow for a single internal jugular vein access site. As illustrated, the device 100 is used for making a puncture from the IVC through the caudate lobe of the liver into the portal vein, as would be done for a DIPS procedure described above. The device 100 can allow for a single internal jugular vein access site for performing the procedure. The needle guide 105 may be used to house and advance a needle 160 into the plane of the ultrasound array 120. For example, an articulating needle may be advanced through the needle guide 105. When such a needle passes through the exit port 110 in the distal end of the needle guide 105, the needle may be activated such that is articulates and/or bends into the portion of the vein or artery that is visualized using the IVUS probe 130. While the needle guides are described herein in use with needles configured to puncture blood vessels, other tools, wires, catheter, liquids, and the like may be passed through the needle guides described herein.

In some embodiments a flexible needle 160 having a preformed or predetermined curved distal portion 150 may be used. Such a needle may be configured such that it may travel through tortious paths. The needle 160 may bend into the substantially same shape as the lumen 107 in which the needle 160 passes through. When at least a portion of the needle 160 passes through the exit port 110 in the distal end of the needle guide 105, the needle 160 may return to its preformed curved configuration. In other words the needle may be configured to straighten when advanced down the needle guide 105 and to reassume its predetermined curve once it is advanced out the distal end of the needle guide 105. Needles with different curves can be utilized. Needles with the desired curve for the specific puncture could be selected and used for the specific procedure. For example, flexible needles 160 having a preformed or predetermined curved distal portion 150 may be selected such that when the distal portion 150 of the flexible needle 160 is advanced out of the exit port 110, the distal portion 150 bends out and into the line of sight of the ultrasound array 120. In this way, an operator may more accurately visualize and control the needle.

Figure 3B:
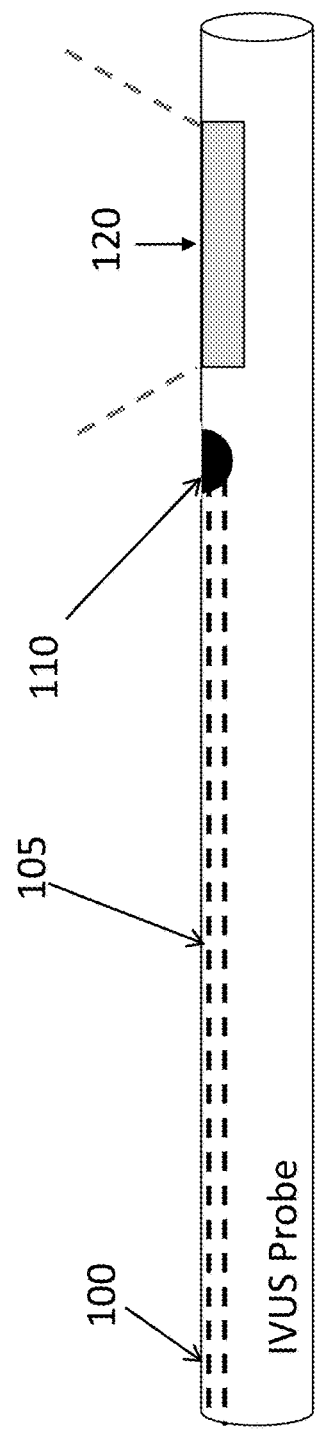
FIG. 3b is a side view of the device of FIG. 1 with the needle removed.

Turning to FIGS. 3a and 3b, the needle guide 105 may extend down the length of the IVUS probe 130. A proximal opening in the guide 105 may allow for insertion of the needle 106. A distal opening allows the needle to exit through an exit port 110. As shown, the exit port 110 is proximal to the IVUS array 120. The exit port 110 may be positioned such that when the needle 160 is advanced out of the exit port 110, the needle 160 is positioned within the visualization area of the ultrasound array 120. As described below, in some embodiments, the needle guide 105 and needle 160 are shaped such that the needle 160 cannot rotate within the needle guide 105.

Figure 4:
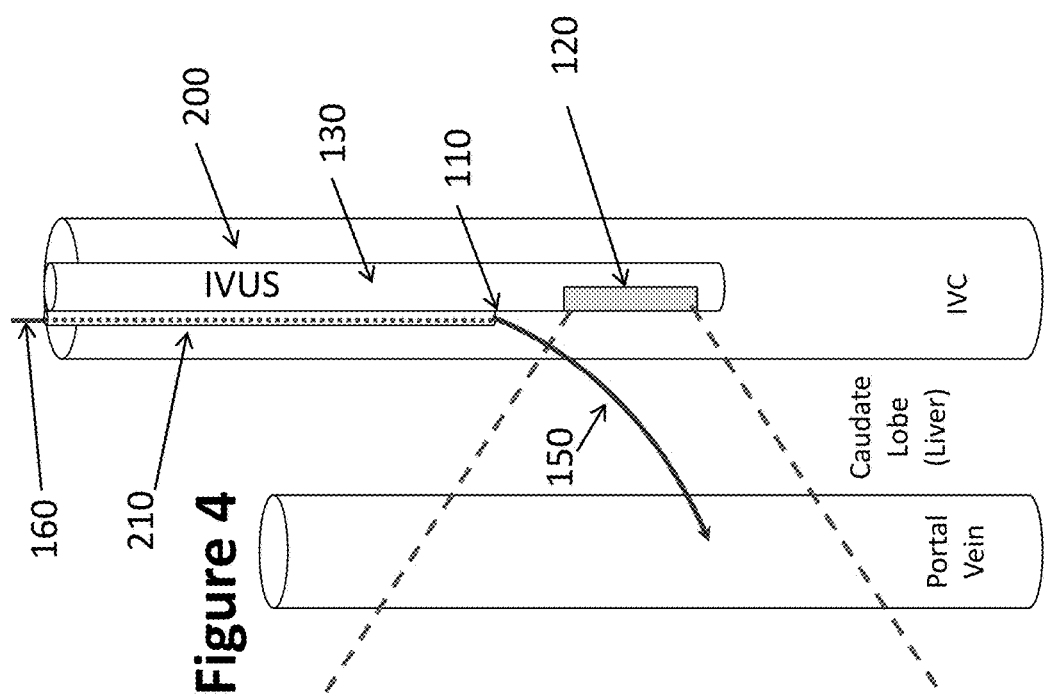
FIG. 4 is a schematic illustration of another embodiment of an IVUS probe having a needle guide. The embodiment is similar to that of FIG. 1, except that the needle guide is coupled to an exterior surface of the IVUS probe.

FIG. 4 illustrates a device 200 having a needle guide 210 coupled to an exterior surface of an IVUS probe 130. In this embodiment, the needle guide 210 is an externally attached to the IVUS probe 130 having at least one lumen 107 extending therethrough. Similar to the embodiments described above, the device 200 may be used in connection with a flexible needle 160 configured to bend into the plane of the ultrasound array 120 when a portion of the needle 160 passes out of the exit port 110. In some embodiments, the flexible needle 160 has a pre-curved distal end.

FIG. 5 is an enlarged side view of the device of FIG. 4. As shown, the needle 160 includes a distal portion 150 that is pre-curved to bend into the viewing area of the ultrasound array 120 as the needle 160 is advanced out of the exit port 110 of the needle guide 210. FIG. 6 is a cross-sectional view of the device of FIG. 5 taken about the line 6-6. IVUS components 115 may extend through the interior of the IVUS catheter 200. The needle 160 passes through the needle guide 210. In certain embodiments, the needle 160 has a diameter that is less than the diameter of the lumen 107 of the needle guide 210. However, the needle 160 may have a larger diameter such the needle fits snugly within the lumen 107 of the needle guide 210. Moreover, while not shown in FIG. 6, the needle 160 may include an internal guidewire passing through the interior of the needle 160. The needle 160 and the guidewire may be moved together or independently.

The embodiments shown in, for example, FIGS. 1-6 may be generally used in accordance with the following method. The method can begin by advancing the IVUS catheter having an intrinsic or extrinsic needle guide into a vein until the target area is reached. The specific target area can then be visualized using the IVUS catheter and attached imaging system. A needle 160 having a pre-curved distal portion and an internal guidewire may be advanced out of the exit port 110 of the needle guide 105, 210 and into the visualization plane of the IVUS catheter 130. In a DIPS procedure, the needle 160 and internal guidewire may be advanced out through the vessel wall, through the caudate lobe of the liver, and into the portal vein. This advancement of the needle 160 and internal guidewire may be viewed in real-time, further ensuring an accurate path. When the needle 160 and internal guidewire are in the correct position, the needle 160 may be withdrawn, leaving the internal guidewire in place. A dilator may be then advanced over the guidewire. A collapsed shunt may be advanced over the dilator. The collapsed shunt may be inflated, creating a passageway for blood to flow from the IVS to the portal vein. The method may be imaged and/or visualized during one or more portions of a procedure because the IVUS catheter stays in the proper viewing position.

In some implementations, the devices disclosed herein may be used in connection with the following method. The method can begin by advancing the IVUS catheter having an intrinsic or extrinsic needle guide into a vein until the target area is reached. The specific target area can then be visualized using the IVUS catheter and attached imaging system. A needle 160 having a pre-curved distal portion may be advanced out of the exit port 110 of the needle guide 105, 210 and into the visualization plane of the IVUS catheter 130. In a DIPS procedure, the needle 160 may be advanced out through the vessel wall, through the caudate lobe of the liver, and into the portal vein. This advancement of the needle 160 may be viewed in real-time, further ensuring an accurate path. When the needle 160 is in the correct position, a guidewire may be advanced through the needle 160 and into the portal vein. The needle 160 may then be withdrawn, leaving the internal guidewire in place. A dilator or angioplasty balloon may be then advanced over the guidewire. A collapsed shunt may be advanced over the dilator. The collapsed shunt may be deployed, creating a passageway for blood to flow from the IVC to the portal vein. The method may be imaged and/or visualized during one or more portions of a procedure because the IVUS catheter stays in the proper viewing position.

Moving on to FIG. 7, in some embodiments, a device 300 can include an internal needle guide 310 comprising at least one lumen 107 having a distal portion that is angled or curved away from the IVUS probe 130. In this way, a relatively straight but flexible needle 160 can exit the needle guide 310 at a predetermined angle in the plane of the ultrasound array 120. As shown in FIG. 7, a flexible needle 160 having a substantially straight distal end 150 can be used. While not shown in the FIG. 7, a flexible pre-curved needle can also be used. The angled or curved portion may be of any length and/or angle.

Similarly, in some embodiments, for example the embodiment shown in FIG. 8, the device 400 may include a needle guide 410 having a lumen 107 with a distal portion that is substantially parallel to the probe 130 but has an exit port 415 configured such that the needle 160 is deflected into the plane of the ultrasound array 120 by a portion of the exit port 415. For example, the exit port 415 may have a curved or rounded surface. When the needle 160 is advanced through the needle guide 410, the needle 160 may contact this surface of the exit port 415 and be deflected away from the probe 130 at the desired angle. In some embodiments, the needle 160 is a curved flexible configured to straighten after exiting the exit port 415 of the needle guide 410. When the needle 160 exits the exit port 415, the needle 160 can return to its preformed shape to puncture the vessel at the desired angle with respect to the IVUS probe 130. While not shown in FIG. 8, in some embodiments, the needle 160 is relatively straight but assumes an angle away from the IVUS probe 130 when it contacts the curved or rounded surface of the exit port 415.

FIGS. 9a and 9b illustrate an embodiment 500 with a needle guide 510 having a distal portion 520 which pops out and away from the IVUS probe 130 when activated. The distal portion 520 may be biased or pre-formed or mechanically actuated such that it may articulate from at least a first position generally parallel to the IVUS probe 130 to at least a second position angled away from the IVUS probe 130. As shown, the needle guide 510 is intrinsic to the IVUS probe 130. FIG. 9a illustrates the distal portion 520 of the needle guide 510 in the "down" position. In this position, the needle guide 510 may be advanced through the vasculature. In some embodiments, a catheter or sheath may also be employed. In these implementations, the IVUS probe 130 and needle guide 510 may be advanced through the catheter or sheath to a desired location.

As shown in FIG. 9b, the needle guide 510 is configured to be moved to the "up" position, providing an angle towards the desired puncture site and/or in a direction away from the IVUS probe 130. In this way, a flexible needle 160 may be advanced through the needle guide 510 and can exit at substantially the same angle as the distal portion 520 of the needle guide 510. The flexible needle 160 may include a distal portion 150 that is pre-curved such that the angle of the puncture may be determined by both the angle of the distal portion 520 of the needle guide 210 and the curvature of the distal portion 150 of the needle 160. In certain embodiments, the angle of the guide is adjusted so that punctures could be made at different angles depending on what is desired for the procedure. As shown in FIGS. 10a and 10b, a needle guide 610 having a distal "pop-up" portion 620 may also be used as an attachment to the exterior of an IVUS probe 130. Further, as shown in FIG. 10b, in some embodiments, more than one needle 160 may pass through the needle guide 510. A straight or pre-curved needle can be used in a similar fashion as described for FIG. 9b above.

In some embodiments, the needle guide may have a distal potion that is configured to articulate away from the IVUS probe. In this way, the precise angle of the needle guide with respect to the IVUS probe may be more accurately controlled. For example, the operator could articulate the needle guide more or less in order to set the precise angle at which the needle will be positioned. Then, the needle may be advanced at the desired angle with respect to the ultrasound probe. In some embodiments, the distal portion of the needle is configured to articulate away from the IVUS probe. In some embodiments, the needle may be mechanically actuated. As described below, in some embodiments, the needle guide and needle are shaped such that the needle is prevented from rotating within the guide.

With reference now to FIGS. 11a and 11b, in some embodiments, the needle guides may be shaped to prevent rotation of the needle relative to the IVUS probe. For example, the needle guide may comprise a lumen having a cross-sectional "pie" shape (or similar shape). The needle may then be shaped so as to pass through the "pie" shaped (or similar shaped) needle guide. That is to say, the needle guide and needle are shaped such that the needle cannot rotate within the guide. This configuration helps ensure that the deflecting needle deflects in the desired direction when exiting the needle guide. In other words, the shaped needle guide is further configured to guide a needle in plane with an IVUS array. Such a shaped needle guide may be internal 710 to the IVUS probe 700 as shown in FIG. 11a or external 755 to the probe 750 as shown in FIG. 11b. In some embodiments, the needle guide 710 has a tubular geometry to accommodate a needle with a circular cross-sectional shape. In certain embodiments, the needle 160 has a width that is greater than a width of the needle guide so as to inhibit rotation relative to the IVUS probe 130.

One or more structures may be used to stabilize the IVUS probe and needle guide at a selected location. For example, the structures may include stents, balloons, wires and/or other mechanisms to stabilize the probe in a desired location. In FIG. 12, a balloon 810 is used to stabilize the IVUS probe having an intrinsic needle guide 100. The balloon 810 may be advanced through the vasculature in a deflated state and then inflated once the particular device is positioned as desired. The balloon(s) 810 may attach to the IVUS probe 130 and/or other support structure. In some embodiments, the IVUS probe 130 includes one or more lumens through which the balloon 810 is advanced. One or more balloons 810 or other stabilization structures may be used. In some embodiments, the balloon 810 attaches directly or indirectly to the outside of the IVUS probe 130 or other support structure or sheath. In some embodiments, the balloon(s) attach to the outside of the IVUS probe 130 or other support structure or sheath so that the balloon(s) advance in unison with the IVUS probe 130 or other support structure or sheath. The balloon(s) may inhibit the device from moving, rotating, and/or deflecting from the desired location. In this way, the needle 160 may be more easily guided to its desired target. As shown in FIG. 12, the balloon 810 is proximal to both the exit port 110 and the IVUS array 120.

Figure 13:
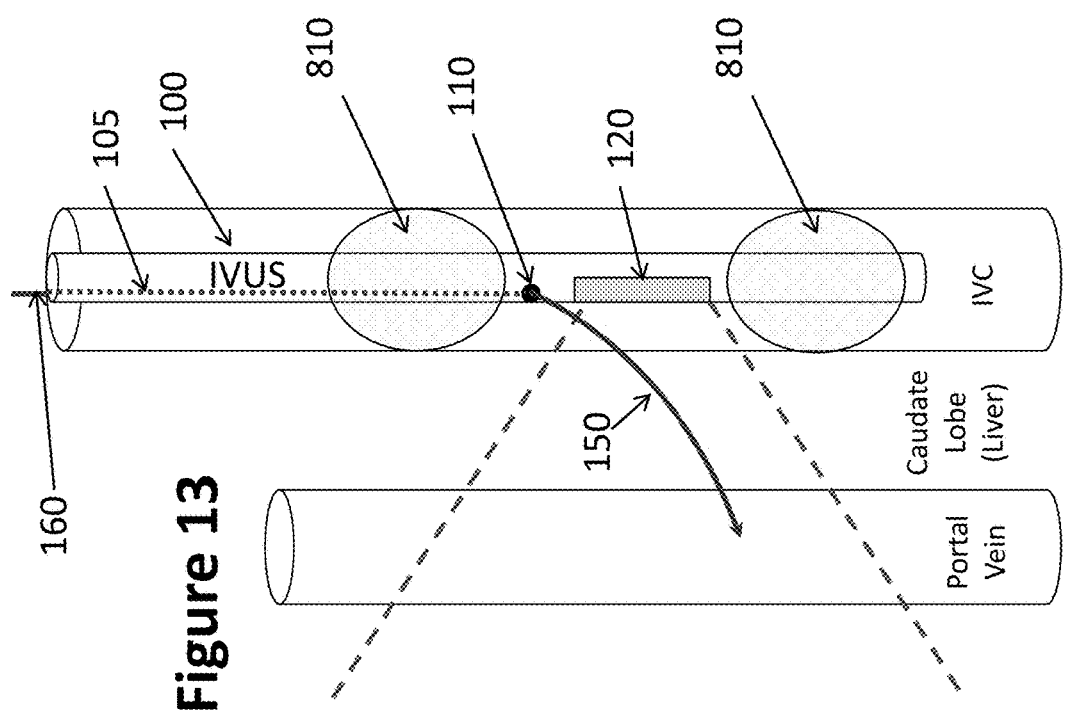
FIG. 13 is a schematic illustration of another embodiment of an IVUS probe having a needle guide. The embodiment is similar to that of FIG. 12 but it includes a second inflatable balloon.
Figure 14:
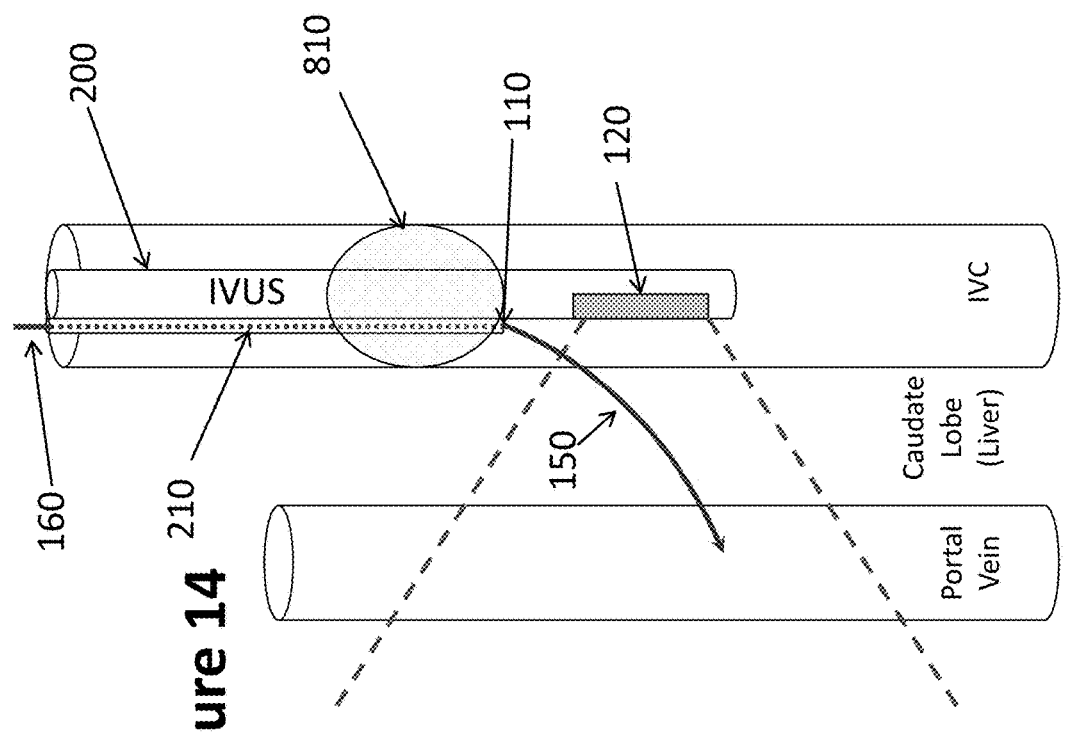
FIG. 14 is a schematic illustration of another embodiment of an IVUS probe having a needle guide. The embodiment is similar to that of FIGS. 4 and 12. As shown, the needle guide is coupled to an exterior surface of the IVUS probe and includes an inflatable balloon.
Figure 15:
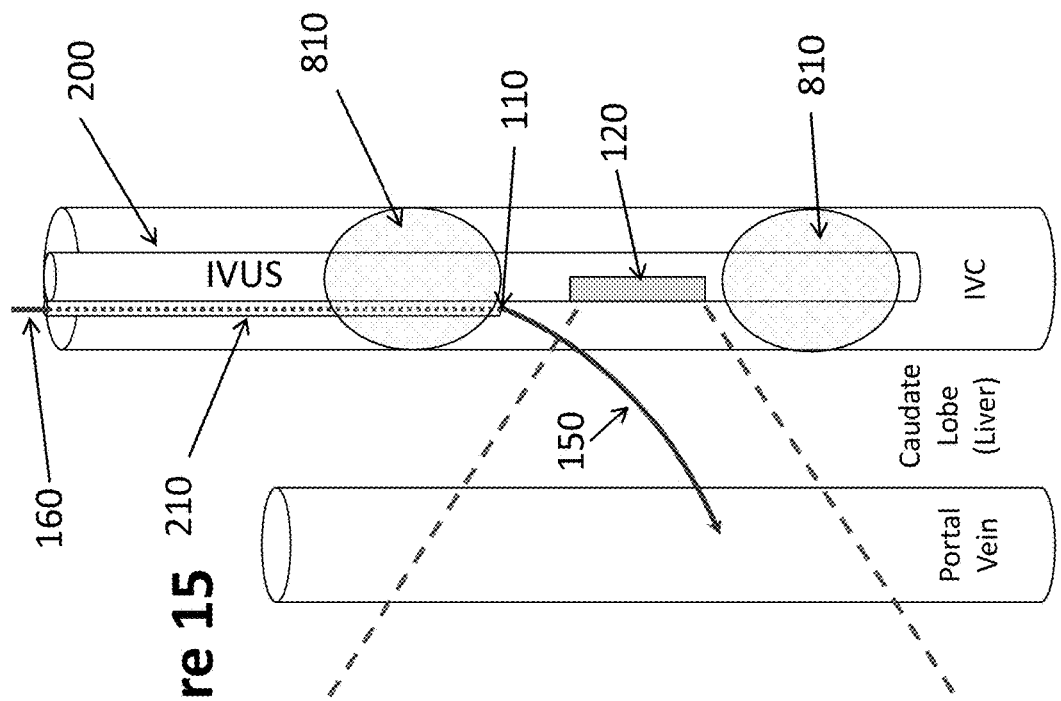
FIG. 15 is a schematic illustration of another embodiment of an IVUS probe having a needle guide. The embodiment is similar to that of FIG. 14 but it includes a second inflatable balloon.

In FIG. 13, two balloons 810 are used to stabilize the IVUS probe having an intrinsic needle guide 100. As shown, one balloon 810 is located proximal to the ultrasound array 120 and proximal to the exit port 110. The other balloon 810 is located distal to the ultrasound array 120. Similar balloon stabilization systems may be implemented with the IVUS probe 200 which has an extrinsic guide 210 as shown in FIGS. 14-15.

Figure 16:
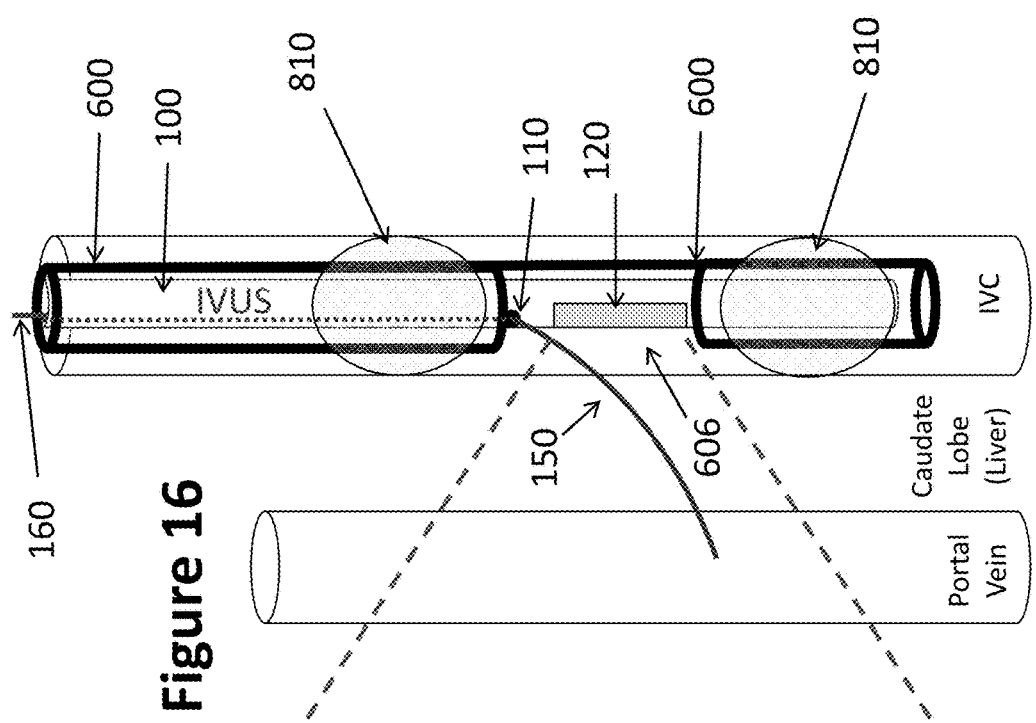
FIG. 16 is a schematic illustration of another embodiment of an IVUS probe having a needle guide. The embodiment is similar to that of FIGS. 1 and 13 but it includes an attachment having a side-opening. Two inflatable balloons are coupled to the attachment.
Figure 17:
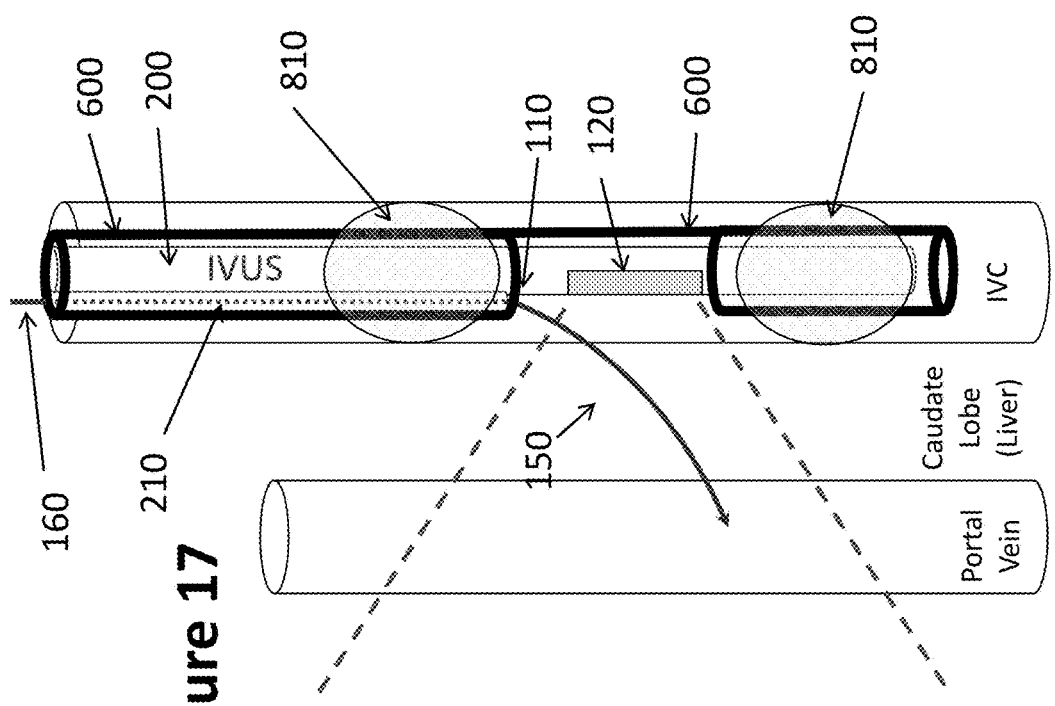
FIG. 17 is a schematic illustration of another embodiment of an IVUS probe having a needle guide. The embodiment is similar to that of FIGS. 4 and 15 but it includes an attachment having a side-opening. Two inflatable balloons are coupled to the attachment.

As shown in FIGS. 16-17, an attachment support structure 600 or guide sheath may be used in connection with the needle guide and IVUS probe. The balloons 810 may be coupled to the support structure 600. In some embodiments, the support structure 600 is advanced over an IVUS probe having a needle guide. In other embodiments, an IVUS probe having a needle guide is advanced into the support structure.

FIG. 16 illustrates the use of a support structure 600 with device 100 from FIG. 1 and described above. FIG. 17 illustrates the use of a support structure 600 with device 200 from FIG. 4. The support structure 600 may include one or more lumens extending therethrough (not shown). The lumens may be used to advance inflated balloons to desired locations and/or used to inflate balloons previously attached to the support structure and/or to deliver fluid. In some embodiments, balloons are wrapped around the external circumference of an IVUS probe such that, when inflated, the balloons occupy the space in between the probe and the vessel walls. In such an embodiment, the balloons may also be configured to substantially stop blood flow. The support structure 600 may include an opening 606 in the distal portion of the support structure 600 configured to expose the ultrasound array 120 and the exit port 110.

Figure 18:
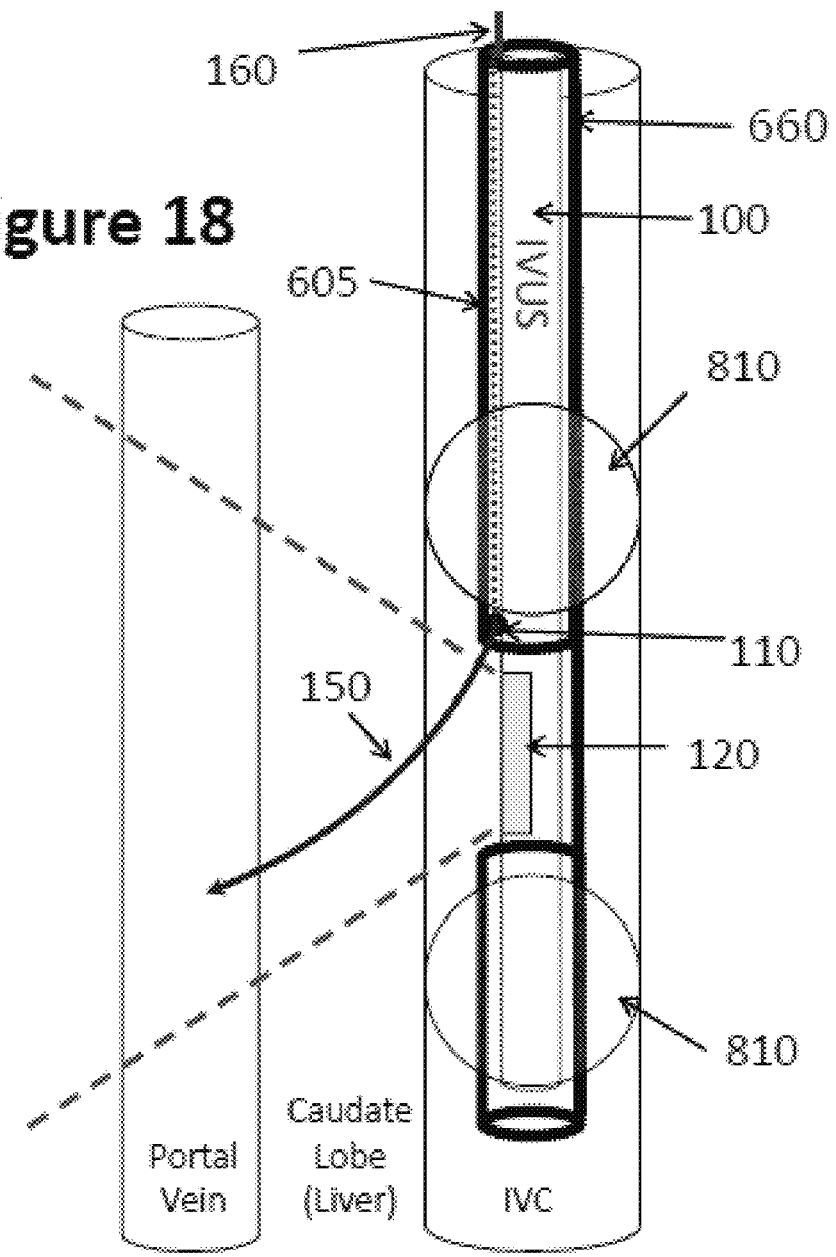
FIG. 18 is a schematic illustration of another embodiment of an IVUS probe having a needle guide. The embodiment is similar to that of FIG. 16 except that the needle guide extends through the attachment.
Figure 19:
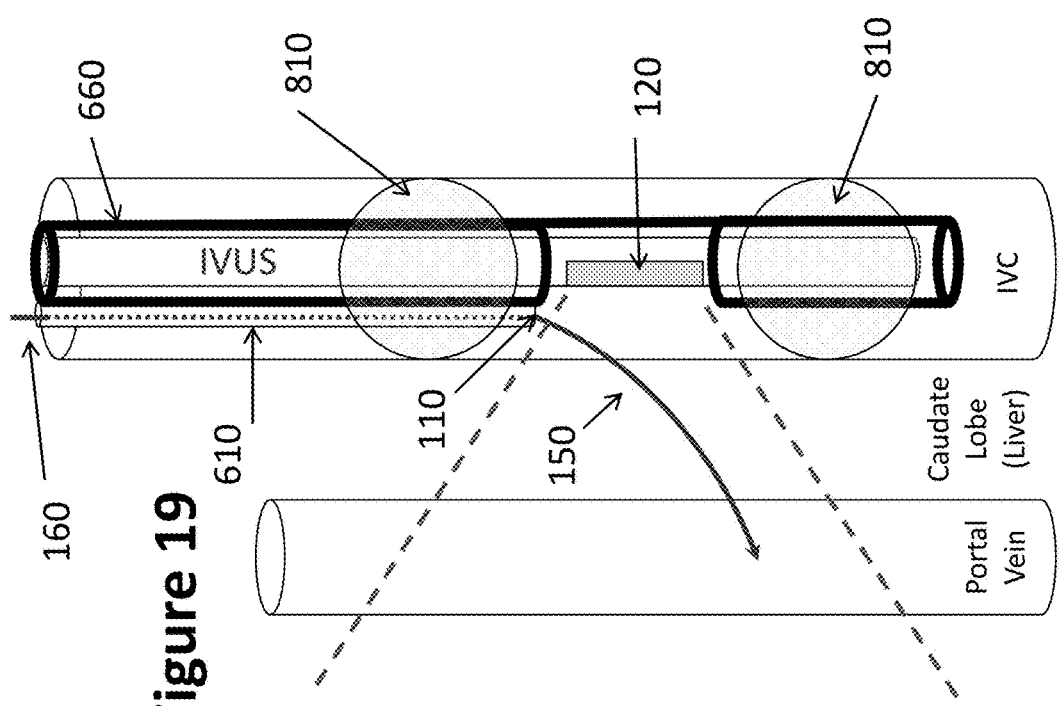
FIG. 19 is a schematic illustration of another embodiment of an IVUS probe having a needle guide. The embodiment is similar to that of FIG. 18 except that the needle guide is coupled to an exterior surface of the attachment.

Turning to FIGS. 18-19, the support structure 600, 660 or guide sheath may include a needle guide 605, 610. The needle guide may be a needle guide 605 that is intrinsic to the support structure as shown in FIG. 18 or a needle guide 610 that is extrinsic attachment as shown in FIG. 19.

Figure 20:
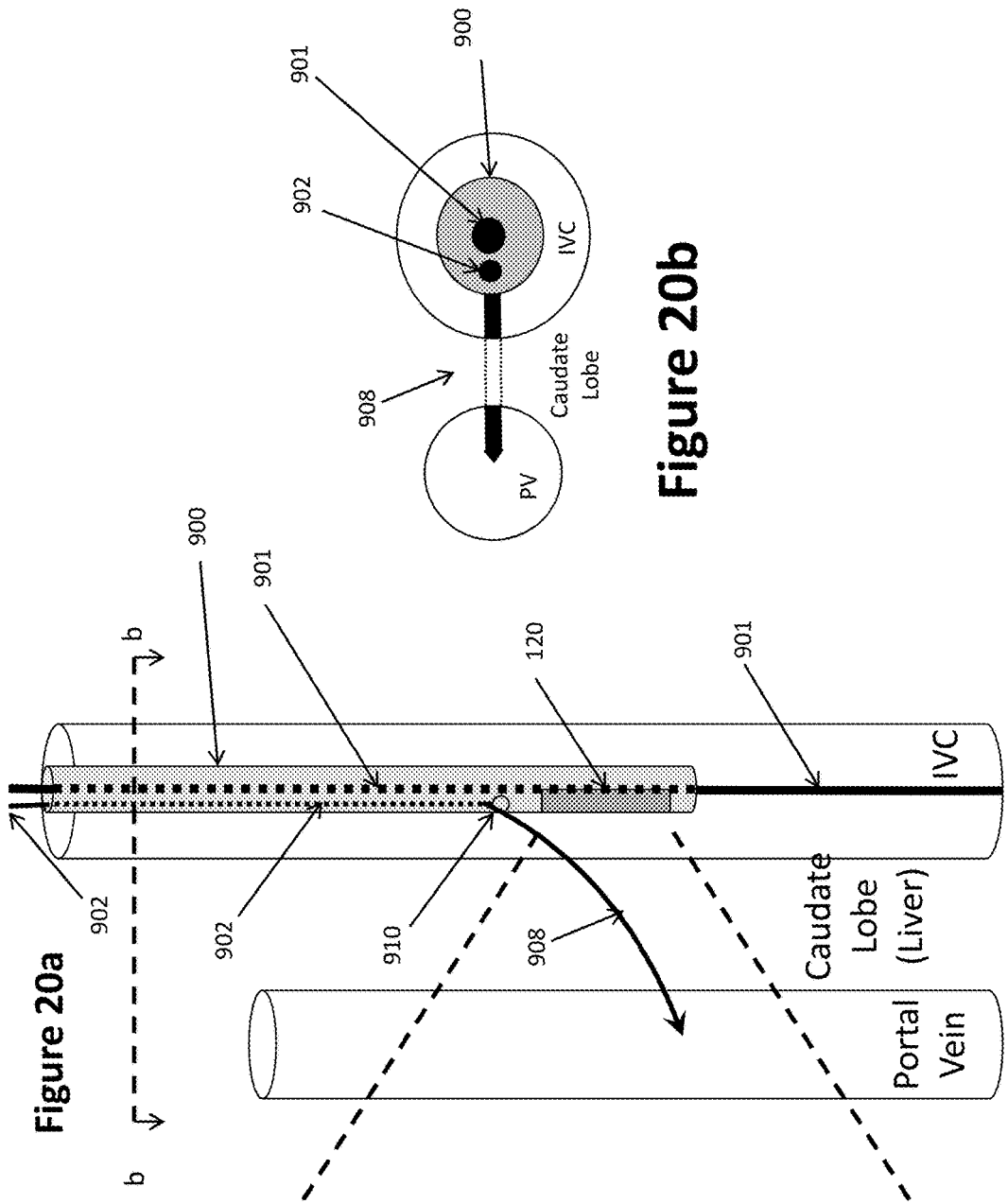
FIG. 20a is a schematic illustration another embodiment of an IVUS probe having a needle guide. The embodiment is similar to that of FIG. 1 except that the IVUS probe includes a guidewire lumen extending therethrough.
FIG. 20b is a schematic cross-sectional illustration of FIG. 20a taken about the line b-b.

Turning now to FIGS. 20a and 20b, another embodiment of an IVUS device 900 with a needle guide is illustrated. FIG. 20b is a cross-section of FIG. 20a taken about the line b-b. As shown, the device 900 includes at least two lumens extending therethrough. The first lumen comprises a central lumen having a relative stiff guidewire 901 extending therethrough. In this way, the device 900 may be advanced over the guidewire 901, through the vasculature, and delivered to the place of interest. The guidewire 901 may be configured to help stabilize the position of the device 900 within the vasculature. As described above, a relatively large amount of force may be required to advance a needle from the device 900 out of the vasculature and into and through the surrounding tissues/organs. Thus, the guidewire 901 may help secure the device 900 within the relative center of the vessel. In addition, the guidewire 901 may help provide additional leverage and act to hold the device in place while the needle pushes through the surrounding tissues and/or organs. Such a guidewire 901 and/or guidewire lumen may be employed with any of the embodiments described herein. In addition, one or more balloons may also be employed to further secure the device 900 in place and to further assist with the accurate insertion of the needle.

Continuing with FIGS. 20a and 20b the device also includes at least a second lumen having a flexible needle 902 extending therethrough. The second lumen includes an exit port 910 positioned proximal to the ultrasound emitter/detector array 120. In the illustrated embodiment, the flexible needle 902 is configured such that it assumes a shape that bends away from the device 900 as the needle 902 is advanced out of the exit port 910. In this way, the device 900 is configured such that the needle 902 is advanced into the area that can be accurately visualized by the ultrasound array 120. A distal portion 908 of the needle 902 may be advanced out of the IVC, through the caudate lobe, and into a portal vein. In other words, as shown in FIGS. 20a and 20b, a portion of the needle 902 is located within the IVC, a portion of needle 902 is located within the caudate lobe, and a portion is located within the portal vein. A guidewire may be advanced through the needle 902. The needle 902 may then be withdrawn leaving the guidewire in place. An angioplasty balloon and/or a stent may be passed over the guidewire to complete the DIPS procedure. In some embodiments, the angioplasty balloon is first advanced over the guidewire followed by the stent.

Figure 21:
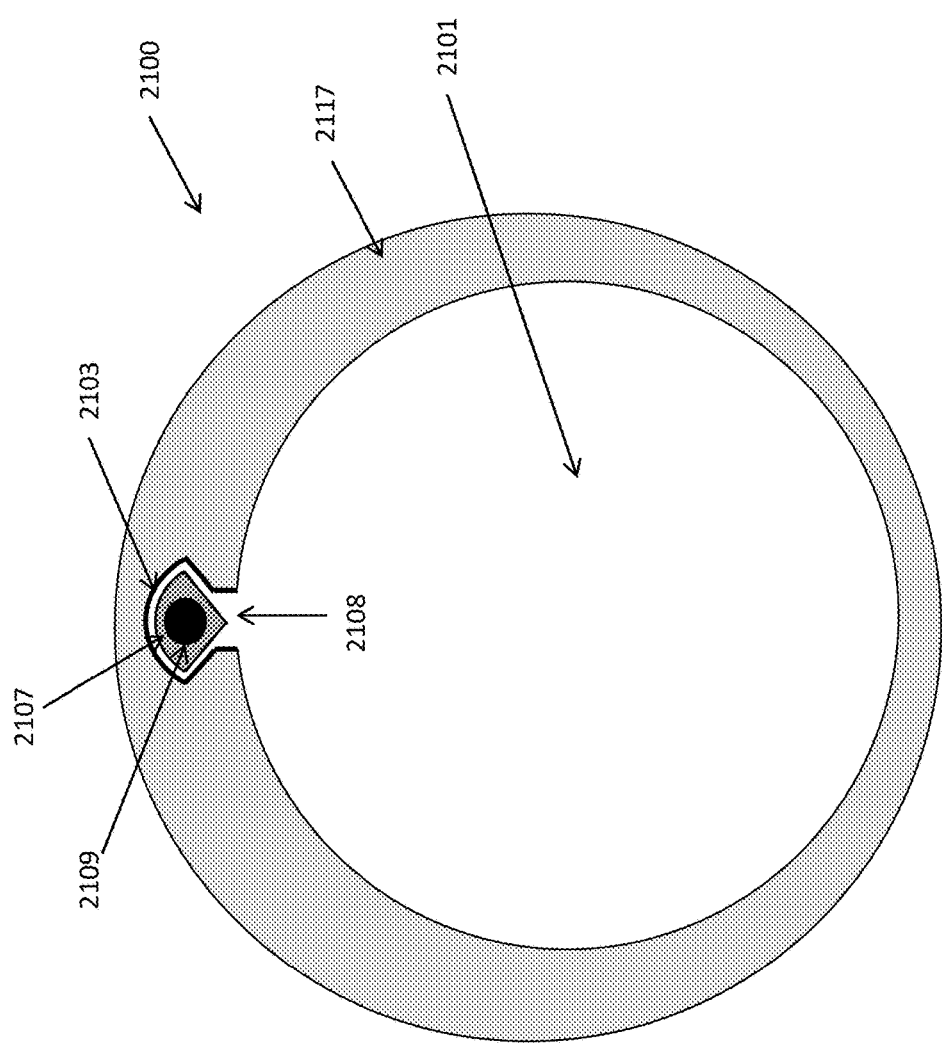
FIG. 21 is a schematic cross-sectional illustration of an embodiment including a sheath having a needle guide and flexible needle extending therethrough. The sheath may be used with an IVUS probe. The flexible needle includes an internal guidewire extending therethrough.

Moving on to FIG. 21, a cross-sectional view of a needle guide sheath 2100 according to another embodiment is shown. The needle guide sheath 2100 ("NGS") may include a central lumen 2101 and a needle guide channel 2103. In summary, the NGS 2100 includes a needle guide that is incorporated into a sheath 2117. The NGS 2100 is configured to accommodate an IVUS probe 130. The NGS 2100 may be about 12-17 French ("F"). The IVUS probe 130 may lock into the NGS 2100 such that the ultrasound array is held in roughly the same plane as the needle guide. A pre-curved flexible needle may be straightened and advanced through needle guide. The needle can reassume its curve once its distal end exits the distal end of the needle guide. The needle may be used to puncturing the portal vein. Any suitable gauge needle may be used. For example, an 18 gauge, a 19 gauge, or a 21 gauge flexible needle may be used. The needle and the needle guide may have a non-round shape to keep needle from rotating in the needle guide so as to ensure that the needle is prohibited from rotating out of the visualization plane of the IVUS probe. In other words, the needle may have a cross section of the needle may have an asymmetrical shape. The needle guide and/needle may have a cross-section shape that is asymmetric with respect to lateral or longitudinal direction. The NGS may also optionally include one or more balloons that can be inflated to stabilize the system within the IVC prior to a puncture procedure. The IVUS probe and or the NGS may or may not be designed to be advanced over a stiff guide wire to further stabilize the system.

As illustrated in FIG. 21, a flexible needle 2107 having an internal guidewire 2109 may be positioned within the needle guide channel 2103. The flexible needle 2107 and needle guide channel 2103 may be shaped and dimensioned such that the flexible needle 2107 cannot rotate within the needle guide channel 2103. For example, as shown in FIG. 21, the flexible needle 2107 has a roughly "pie-shaped" cross-sectional area. The needle guide channel 2103 also includes a roughly "pie-shaped" cross-sectional area that opens to the central lumen 2101 via a roughly rectangular cross-sectional passage 2108. In some embodiments, the needle and the needle guide may be shaped such that a cross section of is asymmetrical shaped. By shaping the guide channel 2103 in this way, the flexible needle 2107 cannot rotate within the guide channel 2103. Furthermore, because the width of the rectangular cross-sectional passage 2108 that connects the needle guide channel 2103 to the central lumen 2101 is less than the width of the flexible needle 2107, the flexible needle 2107 cannot enter the central lumen 2101. The flexible needle 2107 is too large to pass through the rectangular cross-sectional passage 2108. That is to say, the flexible needle 2107 is confined to traveling in a proximal or distal direction within the needle guide channel 2103.

Figure 22:
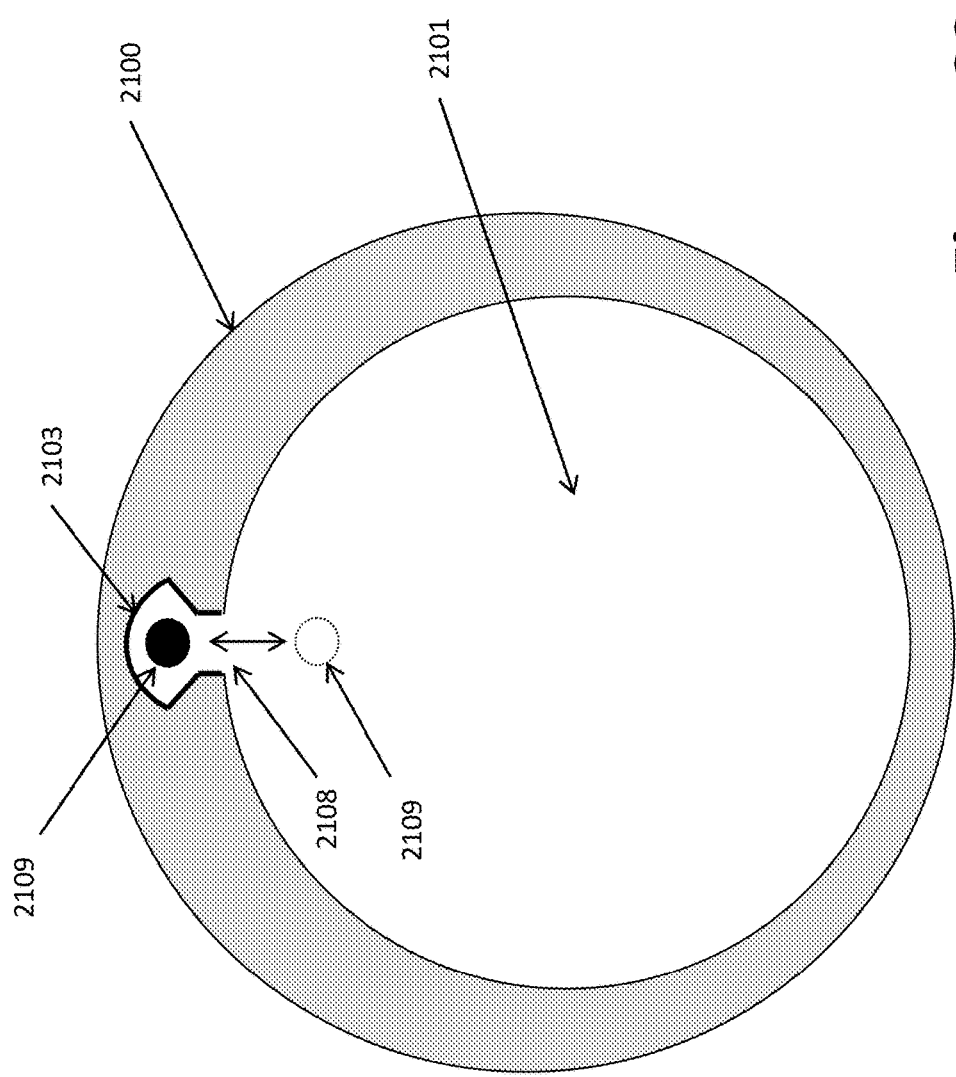
FIG. 22 is the same as FIG. 21 except that the flexible needle has been removed from the needle guide. With the needle removed, the internal guidewire may pass from the needle guide channel into the central lumen of the sheath.
Figure 23:
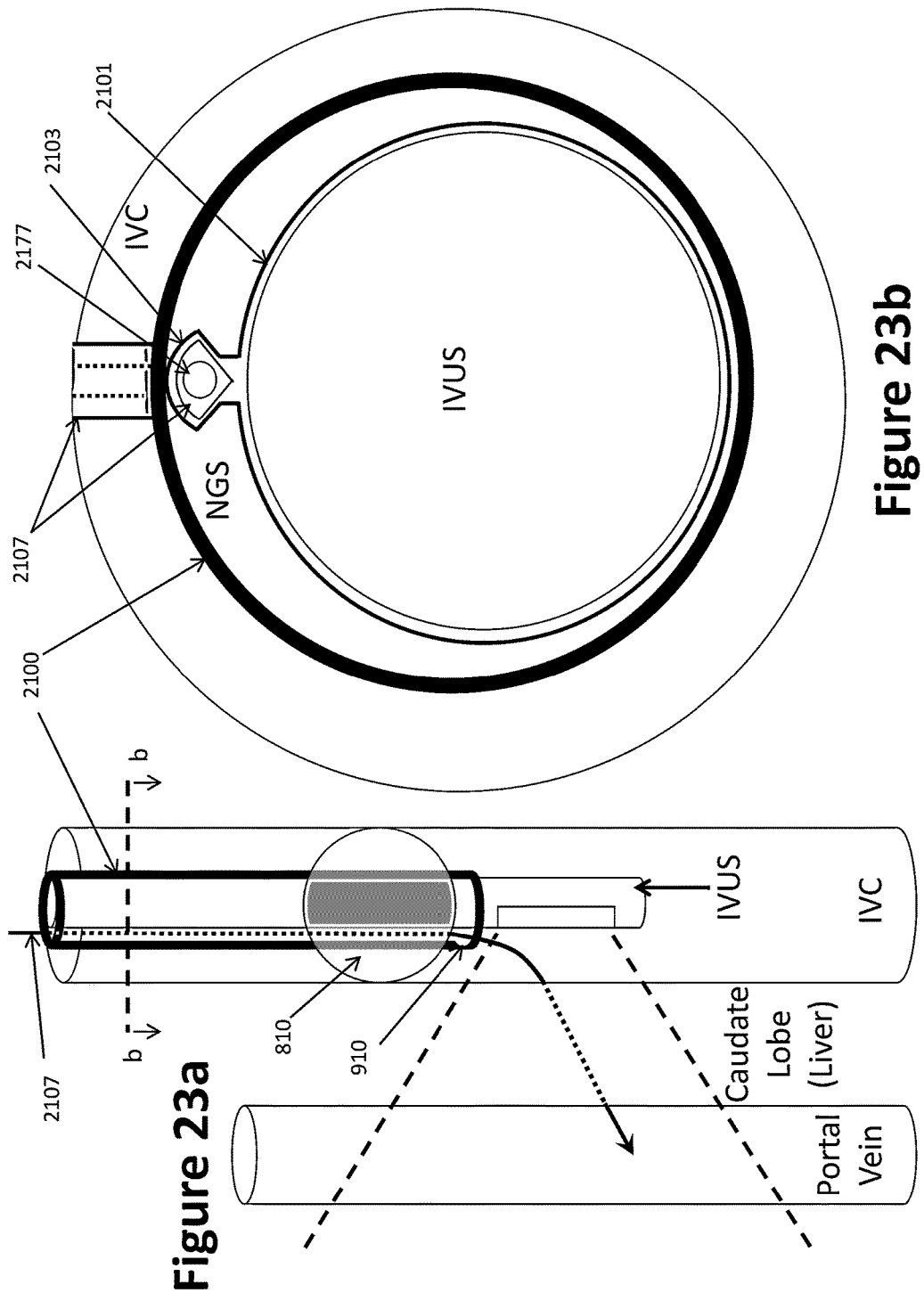
FIG. 23a shows the embodiment of FIG. 21 in the context of a surgical procedure. The embodiment is similar to that of FIG. 1 except that an asymmetrically shaped needle having lumen extending therethrough is positioned within the needle guide.
FIG. 23b is a schematic cross-sectional illustration of FIG. 23a taken about the line b-b, through the inferior vena cava but not including the portal vein.
Figure 24:
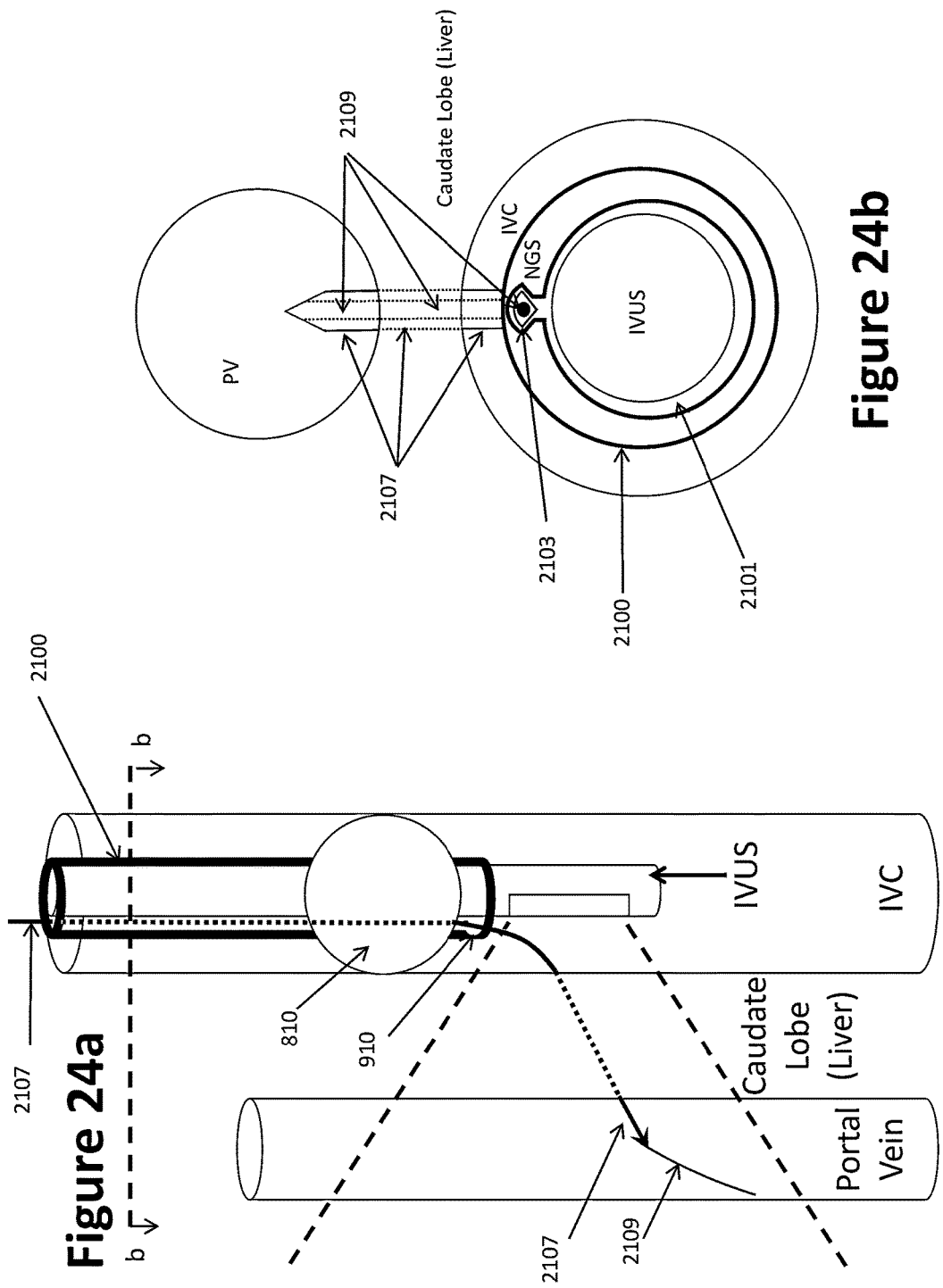
FIG. 24a the same as FIG. 23a except that a guidewire has been advanced through the lumen of the needle into the portal vein.
FIG. 24b is a schematic cross-sectional illustration of FIG. 24a taken about the line b-b, through the inferior vena cava and the portal vein.
Figure 25:
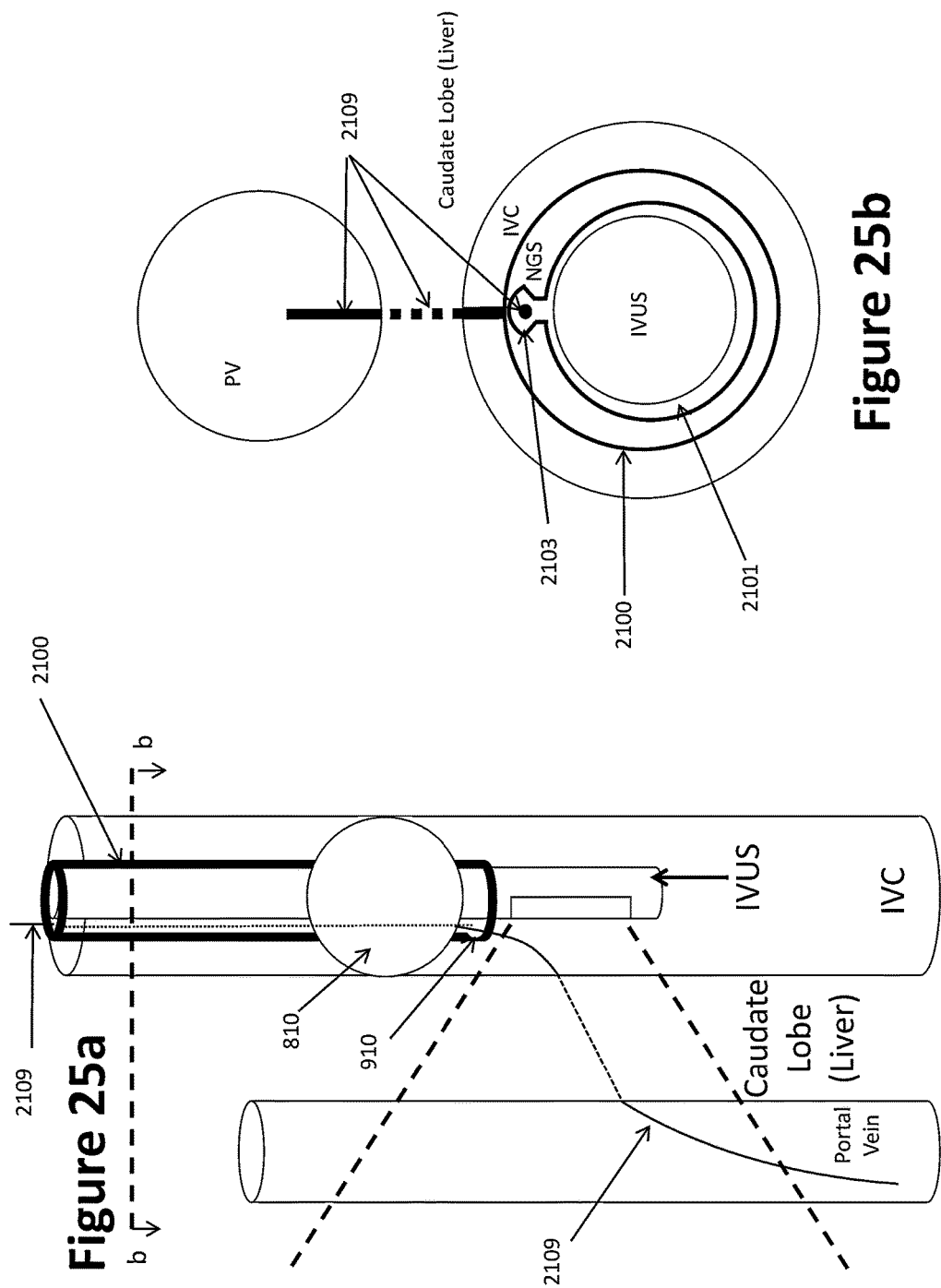
FIGS. 25a and 25b are the same as FIGS. 24a and 24b except that the needle is removed.
Figure 26:
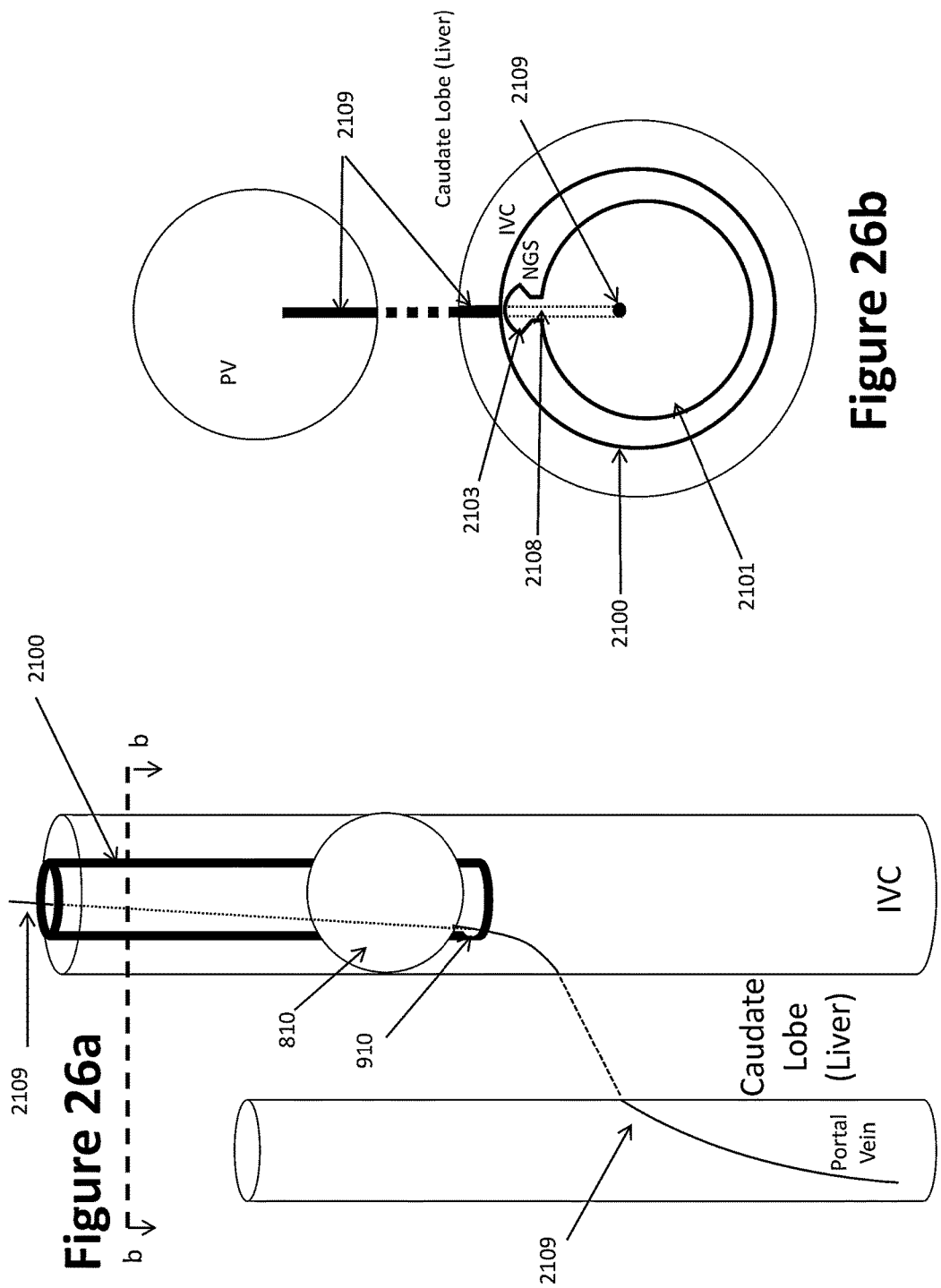
FIGS. 26a and 26b are the same as FIGS. 25a and 25b except that the IVUS probe is removed. With the needle and the IVUS probe removed, the internal guidewire may pass from the needle guide channel into the central lumen of the sheath.
Figure 27:
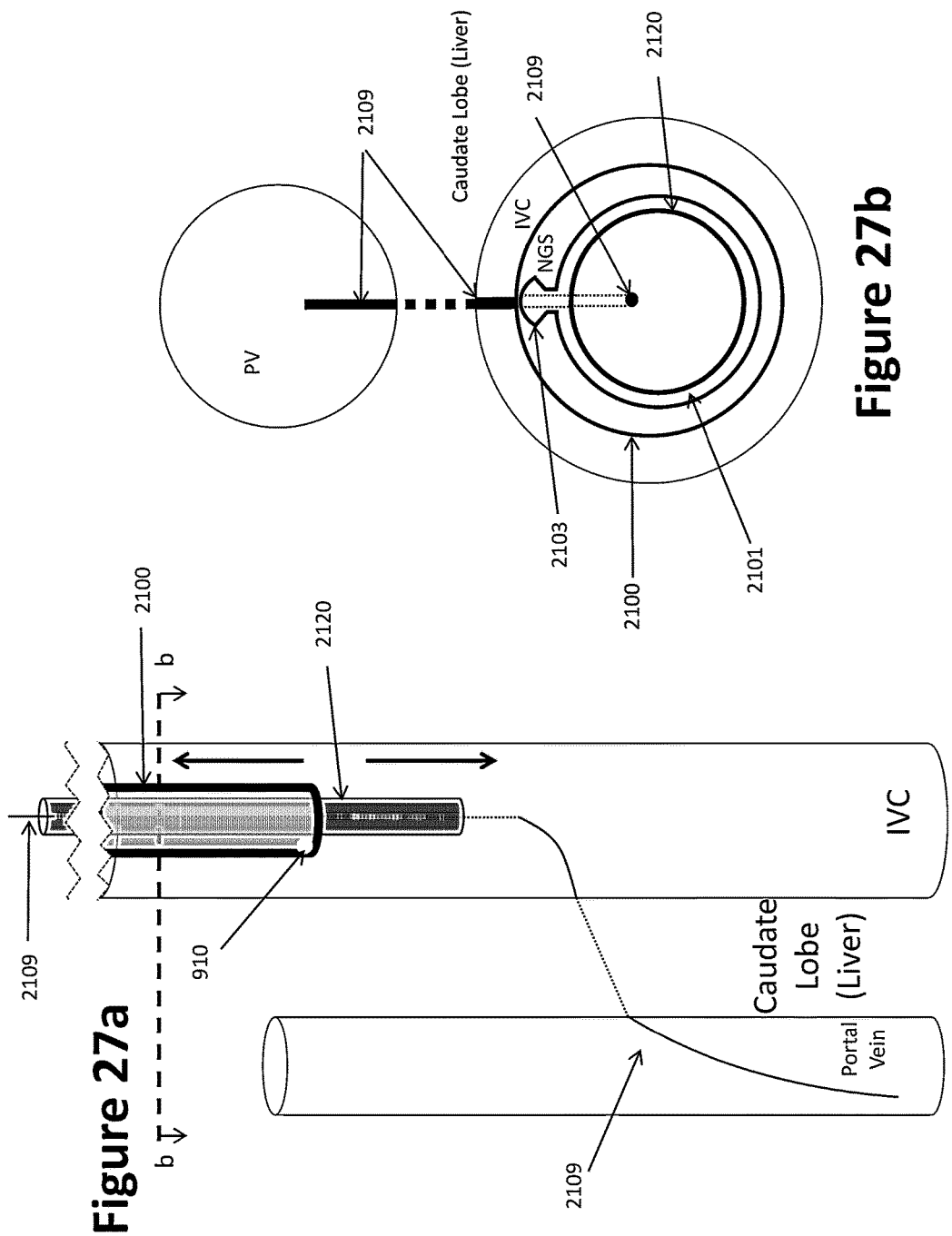
FIGS. 27a and 27b are the same as FIGS. 26a and 26b except that a working sheath is advanced over the wire and through the sheath. As shown, the sheath is also partially withdrawn. Advancing the working sheath over the wire may further pull the wire into the central lumen of the sheath.
Figure 28:
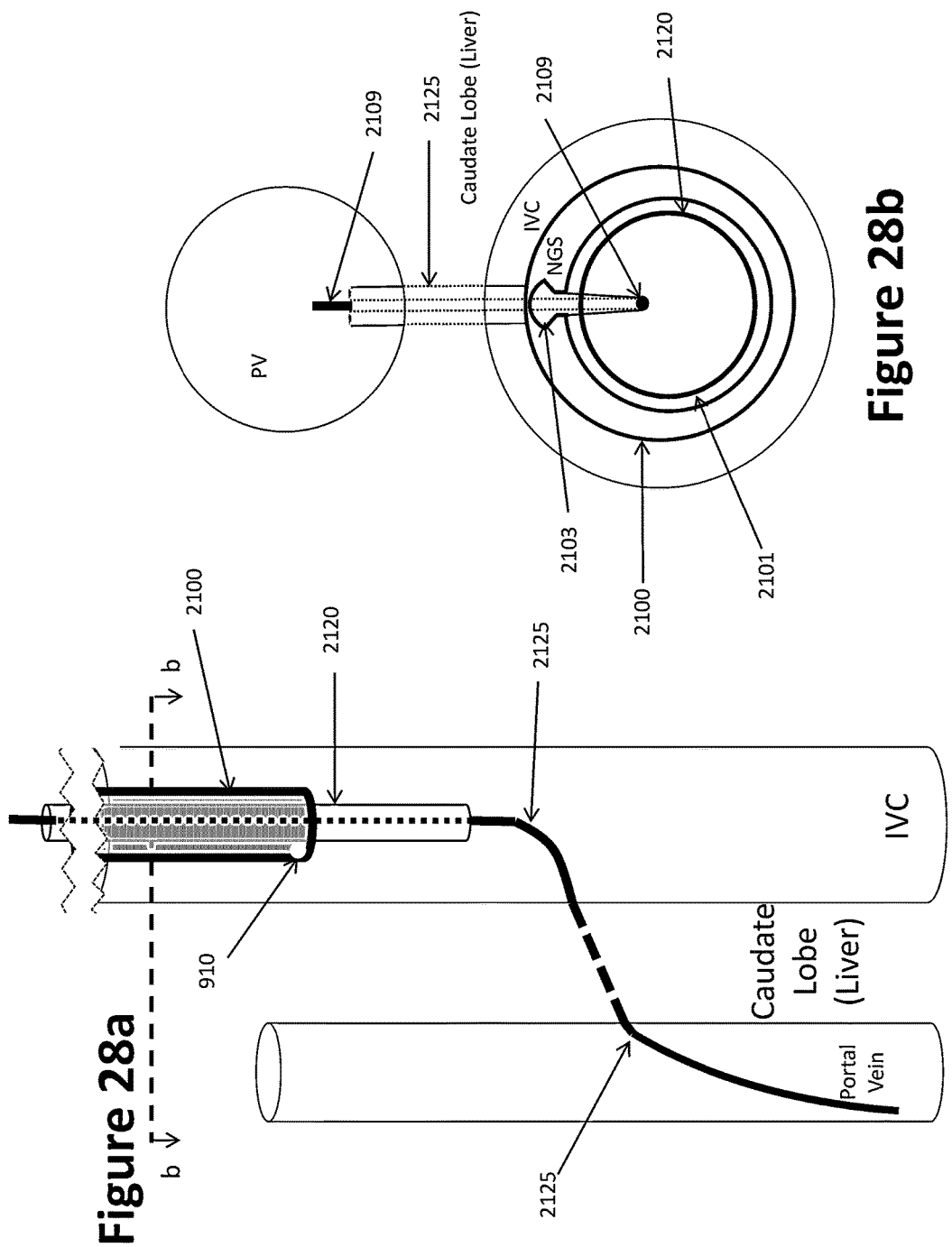
FIGS. 28a and 28b are the same as FIGS. 27a and 27b except that a balloon stent is advanced over the wire in a collapsed configuration.
Figure 29:
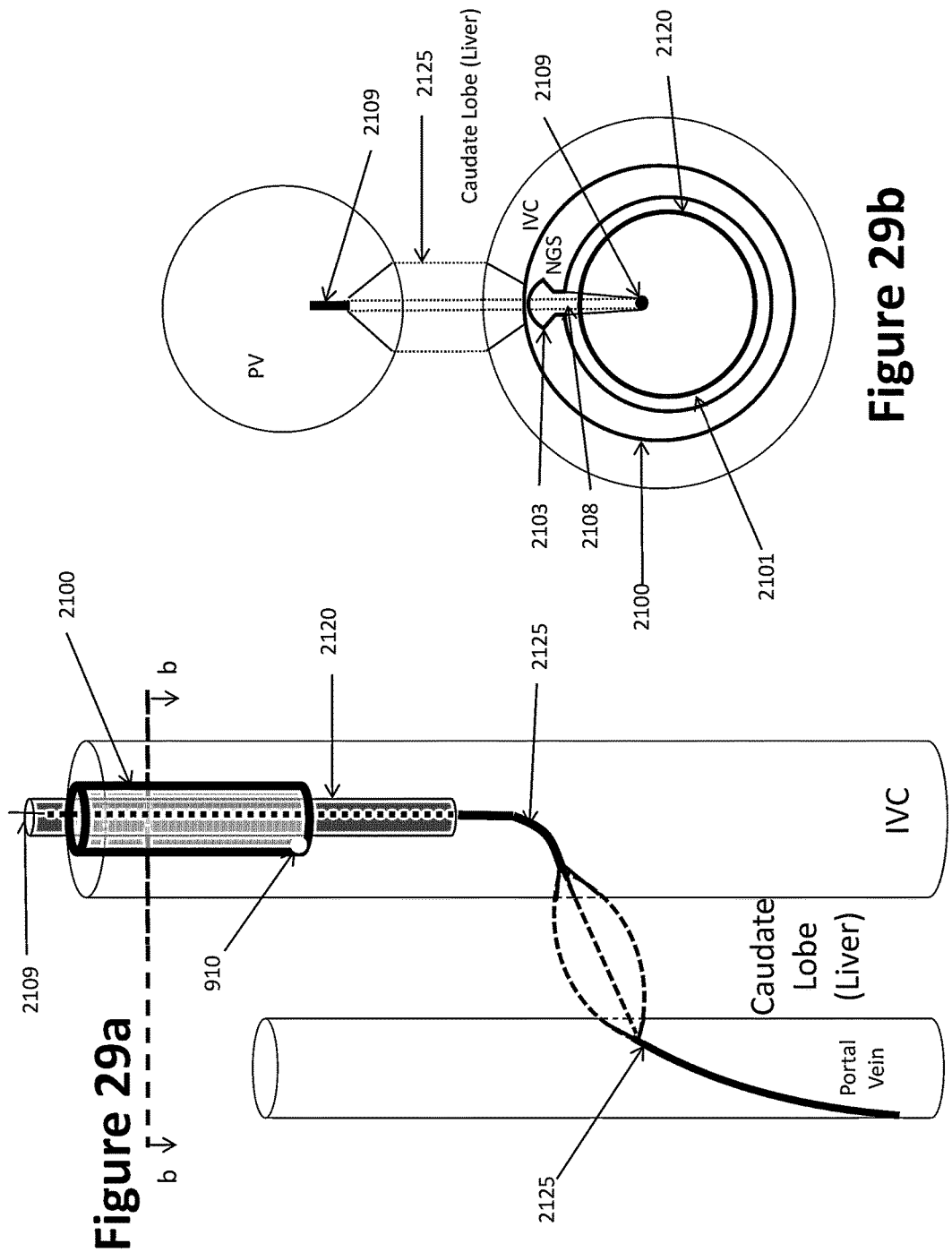
FIGS. 29a and 29b are the same as FIGS. 28a and 28b except that a balloon stent is inflated forming a shunt between the inferior vena cava and the portal vein.

As shown in FIG. 22, the flexible needle 2107 may be withdrawn such that only the internal guidewire 2109 remains. The internal guidewire 2109 and needle guide channel 2103 may be shaped and dimensioned such that the internal guidewire 2109 may pass out of the needle guide channel 2103 and into the central lumen 2101 through the passage 2108. In other words, the internal guidewire 2109 may be dimensioned such that its thickness is less than the minimum width of the passage 2108 that joins the needle guide channel 2103 with the central lumen 2101. In this way, when the flexible needle 2107 is withdrawn over the internal guidewire 2109, the relative size of the internal guidewire 2109 allows the guidewire 2109 to pass from the needle guide channel 2103, through the passage 2108, and into the central lumen 2101. Other catheters, needles, or equipment may then be inserted over the guidewire 2109 and through the central lumen 2101. The guidewire 2109 may be any suitable dimension. For example, in some embodiments the guidewire 2109 has a thickness between 0.018-0.035 inches.

FIGS. 23-29 illustrate an example implementation of the NGS 2100 and related components. As shown, in FIGS. 23*a* and 23*b*, the NGS 2100 may be positioned within the IVC. The NGS 2100 may be guided to desired portion of the IVC by advancing the NGS over a guidewire (not shown). Accordingly, the NGS may include may include an introducer with a guidewire lumen that allows the NGS to be advanced over the guidewire into the appropriate position (not shown). An IVUS catheter may then be inserted through the central lumen 2101 of the NGS 2100. In some embodiments, the IVUS catheter is delivered to the portion of the IVC first and then the NGS 2100 is inserted over the IVUS catheter. The IVUS catheter may include a guidewire lumen (not shown) and be inserted over a guidewire. The NGS 2100 may then be inserted over the IVUS catheter. In some embodiments, the sheath and the IVUS are coupled together and/or are inserted at substantially the same time.

As discussed above, the guidewire may serve as a stabilization means for the IVUS catheter and/or the NGS 2100. As shown in FIG. 23*a*, a balloon 810 may be inflated to secure the IVUS catheter and the NGS 2100 in place and to further stabilize the system. A flexible needle 2107 having lumen 2177 extending therethrough is then inserted through the needle guide channel 2103. When the flexible needle 2107 passes out of the exit port 910, the flexible needle 2107 bends away from the IVUS catheter and the NGS 2100 and into the visualization area of the IVUS catheter. As shown, the flexible needle 2107 passes out of the IVC, through the caudate lobe, and into the portal vein. In other embodiments, a guidewire is advanced through the lumen 2177. Thus in some embodiments, the needle and the guidewire may be advanced through the puncture site at substantially the same time.

FIG. 24*a* similar to FIG. 23*a* except that a guidewire has been advanced through the lumen of the needle into the portal vein. FIG. 24*b* is a cross-sectional view illustrating the positioning of the flexible needle 2107 having an internal guidewire 2109. As shown, the flexible needle 2107 and internal guidewire 2109 are positioned within the needle guide channel 2103. The needle 2107 and internal guidewire 2109 then deflect at an angle away from the NGS 2100 and the IVUS catheter.

Moving on to FIGS. 25*a* and 25*b*, after the flexible needle 2107 is properly positioned as determined by ultrasound imaging and the guidewire 2109 has been advanced through the flexible needle 2107 into the portal vein, the flexible needle 2107 may be withdrawn, leaving the internal guidewire 2109 in position. For example, the proximal end of the needle may be pulled out of the needle guide over the internal guidewire 2109. As shown in FIGS. 25*a* and 25*b*, the internal guidewire 2109 passes out of the IVC, through the caudate lobe, and into the PV.

Turning to FIGS. 26*a* and 26*b*, the IVUS catheter may be removed from the NGS. With the IVUS catheter removed, the guidewire 2109 may pass out of the needle guide channel 2103, through the passage 2108, and into the central lumen 2101.

With reference to FIGS. 27*a* and 27*b*, a working sheath 2120 may be advanced over the guidewire 2109 and through the central lumen 2101 of the NGS 2100. By advancing the working sheath 2120 over the guidewire 2109, the guidewire may be pulled out of the needle guide channel 2103 and into the central lumen 2101 of the NGS 2100. As shown in FIG. 27*a*, the working sheath 2120 may be advanced such that it exits the NGS 2100. In some embodiments, the working sheath 2120 may be may of a pliable material such that is may stretch in the radial direction. The working sheath 2120 may be about 10-15 F. The NGS 2100 may be kept in place to provide extra support for the remainder of the procedure. The support balloon may be re-inflated if extra support is needed (e.g. for advancing an angioplasty balloon across the tract for dilation). The remaining steps may be carried out as desired by one skilled in the art.

FIGS. 28*a* and 28*b* illustrate a simplified illustration of a collapsed balloon 2125 that may be advanced over the guidewire 2109. Various dilators and/or stiffening cannulas and the like may be used to aid the placement of the balloon in position. FIGS. 29*a* and 29*b* illustrate a simplified illustration of the inflated balloon, establishing a fluid pathway between the IVC and the PV. A shunt or covered stent may be advanced over the balloon.

Figure 30:
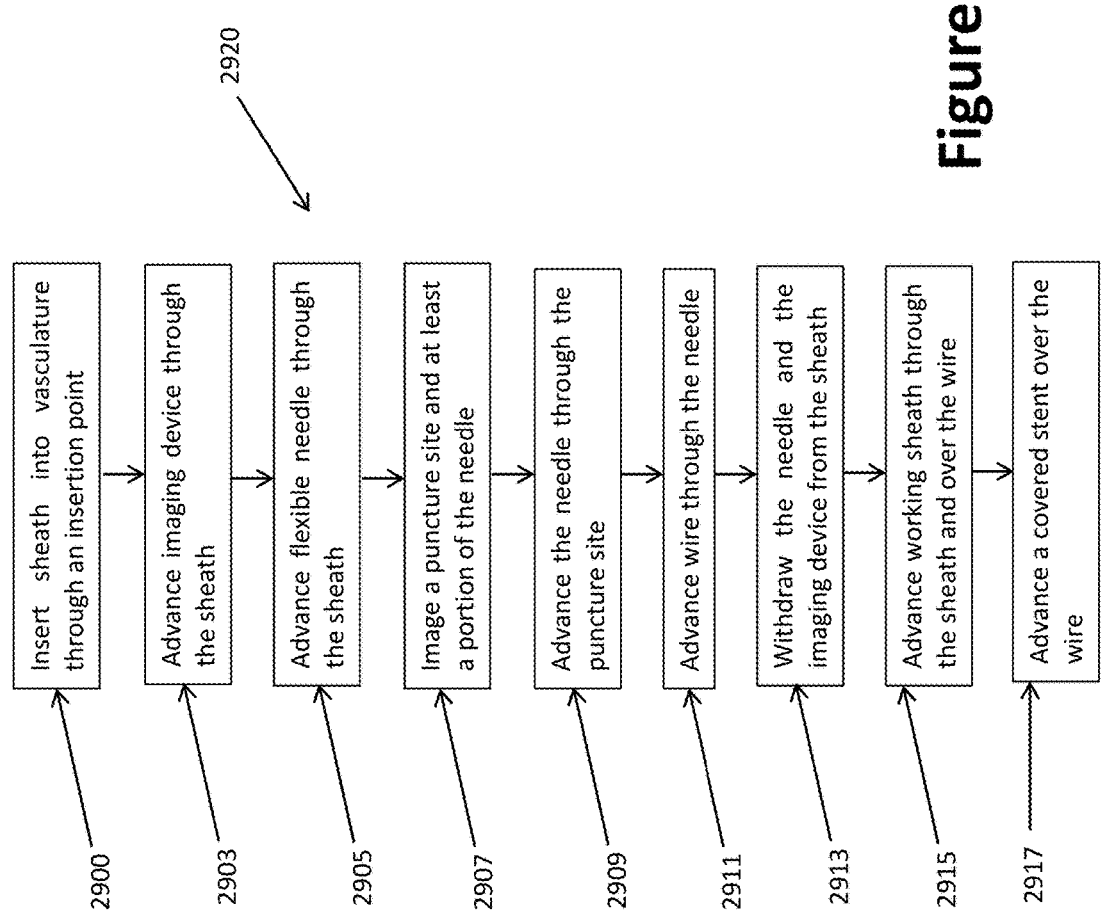
FIG. 30 is a flow diagram illustrated a method of preforming a surgical procedure according to one embodiment.
Figures 31A, 31B:
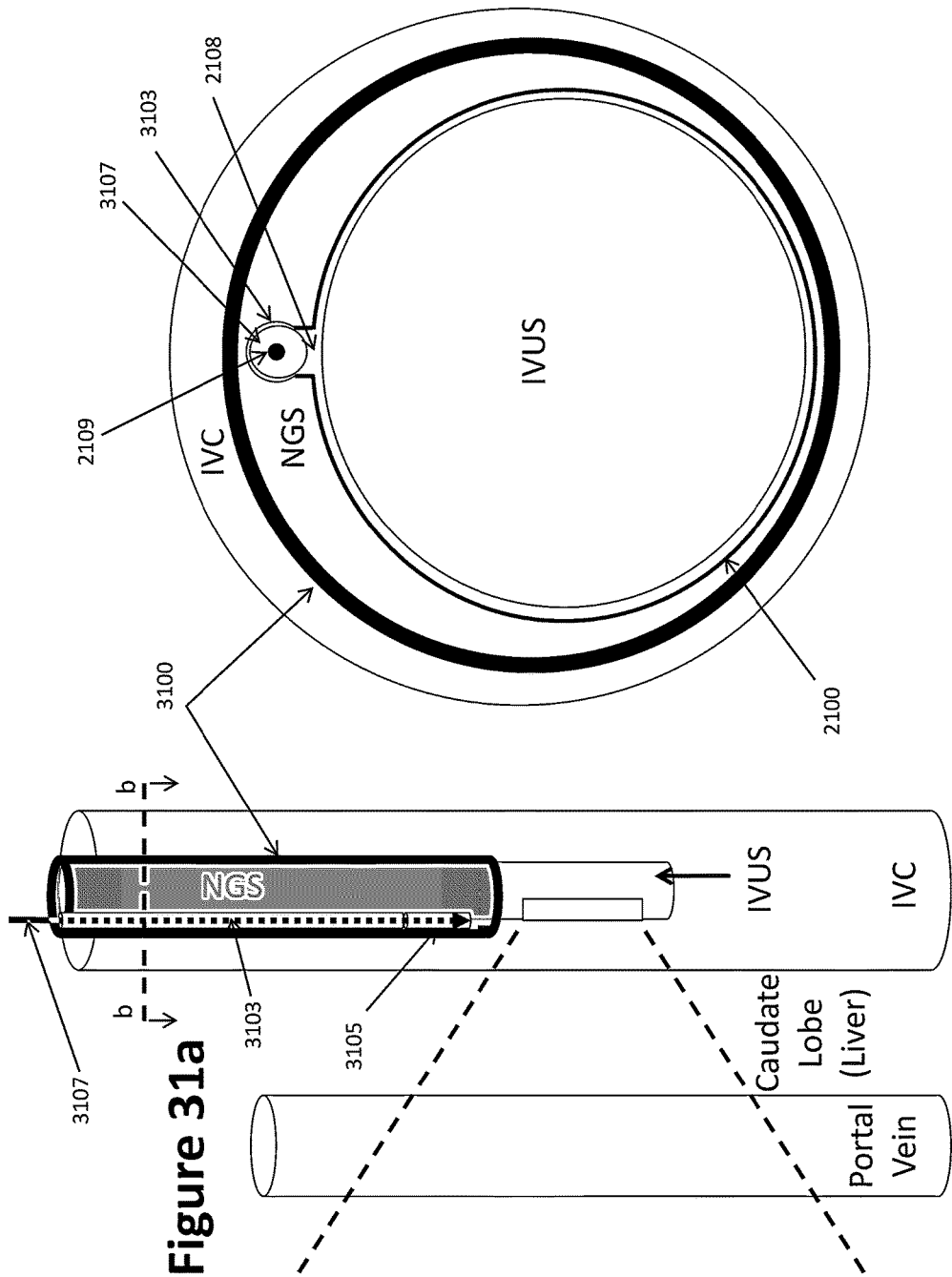
FIG. 31a shows another embodiment of IVUS probe having a needle guide. The embodiment is similar to that of FIGS. 5, 9a, 9b, and 23a except that the sheath includes a needle guide having an articulating distal end. As shown, a needle having a circular shaped cross-section and an internal guidewire is positioned within the needle guide.
FIG. 31b is a schematic cross-sectional illustration of FIG. 31a taken about the line b-b, through the inferior vena cava but not including the portal vein.

Moving now to FIG. 30, a flow diagram illustrating and example method 2920 for performing a DIPS procedure is shown. While the steps in this flow diagram and other flow diagrams in the disclosure are illustrated in a particular order, the various steps are only arranged in this order as an example and are not meant to be limited to the specific order or hierarchy presented. In addition, all of the steps may not be necessary. Moreover, the methods disclosed herein use may include additional steps that are not explicitly illustrated by flow diagrams. As shown in FIG. 30, the method can begin at block 2900 by inserting a sheath into a patient's vasculature through an insertion point. The sheath may include a needle guide. The method can continue at block 2903 by advancing an imaging device though the sheath. The imaging device may comprise a digital camera and/or an ultrasonic imaging probe. The method can continue at block 2905 by advancing a flexible needle through the sheath. The flexible needle may include an internal lumen. A guidewire may be advanced through the lumen. The method can continue at block 2907 by imaging the desired puncture site and at least a portion of the needle. The method can continue at block 2909 by advancing the needle through the puncture site. The puncture site may be a vessel wall. In some embodiments, the needle punctures through the wall of the intrahepatic segment of the IVC into the intrahepatic portion of the portal vein. The puncture may pass through the caudate lobe of the liver.

The method can continue at block 2911 by advancing a wire through the needle. The wire may provide a tract from the IVC to the intrahepatic portion of the portal vein. The method can continue at block 2913 by withdrawing the needle and the imaging device from the sheath. The method can continue at block 2915 by advancing a working sheath through the guide sheath and over the wire. The tract may be dilated by advancing a dilator over the wire. In some embodiments, an angioplasty balloon is advanced over the wire to dilate the tract. The method can end at block 2917 by advancing a covered stent over the wire and through the working sheath for deployment. Fluoroscopic guidance may be used. The covered stent may be inflated to form a shunt for blood to flow from the PV to the IVC. The shunt may lower pressure in the portal venous system, and thus may also stop and/or prevent variceal bleeding and/or stop or decrease the development of ascites or hepatic hydrothorax.

FIGS. 31-39 illustrate an example implementation of another embodiment of a NGS 3100 and related components. In summary, this embodiment of the NGS 3100 includes a needle guide channel 3103 with an articulating distal portion 3105. As shown, the articulating needle guide channel 3103 is part of the NGS 3100. However, a needle guide channel having an articulating distal portion may be part of the IVUS probe itself. That is to say, a sheath is not required in all embodiments. Rather, in some embodiments, a unitary IVUS probe having an intrinsic or extrinsic needle guide may be employed. Furthermore, while the needle guide channel 3103 with an articulating distal portion 3105 is shown as being on the interior of the sheath, the needle guide channel 3103 with an articulating distal portion 3105 may be positioned on the exterior of the sheath or partially on the interior of the sheath and partially on the exterior of the sheath.

Similar to the embodiment discussed above, the NGS 3100 includes at least a central lumen 2100 configured to receive an IVUS catheter. Any suitable IVUS catheter may be employed. The NGS 3100 also includes a needle guide channel 3103 that opens into the lumen 2100 via passageway 2108. As shown in, for example, FIG. 31*b*, the flexible needle 3107 may be advanced through the needle guide channel 3103. The flexible needle 3107 may include a guidewire 2109 extending therethrough. In some embodiments, the guidewire is advanced through the needle only after the puncture is made with the needle. Unlike the embodiment described above, the needle guide channel 3103 includes a roughly circular shaped cross-section that can house a needle having a circular cross-sectional shape as well. That is to say, the needle 3107 may rotate within the needle guide channel 3103. Of course, a differently shaped needle guide and/or needle may be used. For example, the needle guide shape and needle shape shown in FIG. 21 may be used with the embodiment shown in FIGS. 31-39.

The needle guide channel 3103 of NGS 3100 includes a distal portion 3105 that is configured to articulate away from the center of the needle guide sheath. The amount of articulation may be controlled by the operator. In other embodiments, the distal portion 3105 includes just two positions: straight and articulated. The passage 2108 connecting the needle guide channel 3103 and the central lumen 2100 may be sized such that the needle 3107 may not pass from the needle guide channel 3103 into the central lumen 2100. For example, the width of the passage may be less than the cross-sectional width of the needle. In this way, the needle is confined within the needle guide channel 3103 in the transverse direction.

FIG. 32*a* illustrates the distal portion of the needle guide channel 3103 in an articulated state. The distal portion 3105 of the needle guide channel 3103 may be articulated to any angle between 0-90° with respect to the surface of the NGS. In some embodiments, the angle is about 45° with respect to a surface of the NGS. In this way, as the needle is advanced out of the needle guide, it moves into the line of sight of the IVUS catheter. Thus, accurate visualization of the needle guide may be accomplished.

Figures 33A, 33B:
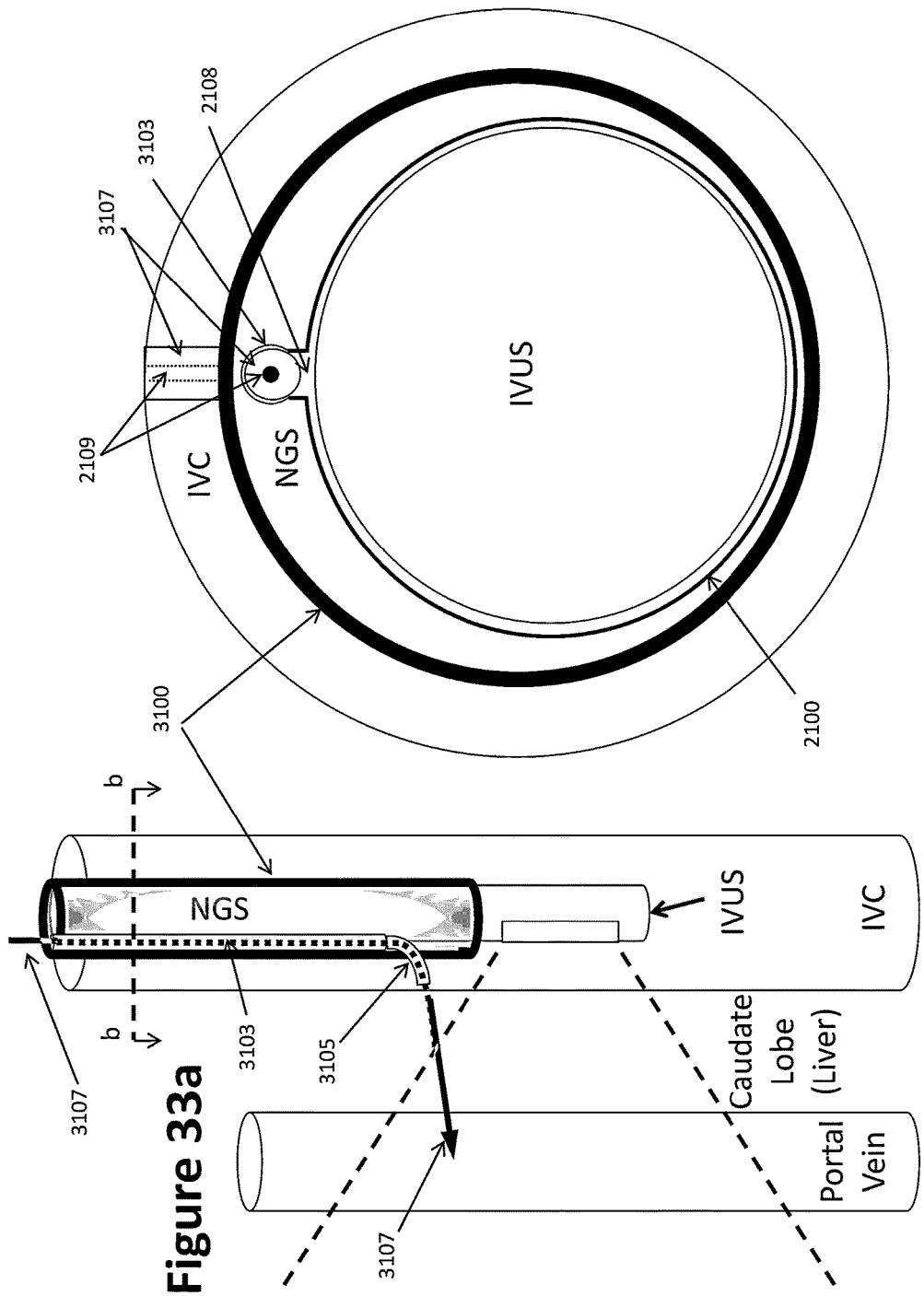
FIGS. 33a and 33b are the same as FIGS. 32a and 32b except that needle having an internal guidewire is advanced out of the needle guide and into the portal vein.

Moving on to FIGS. 33*a* and 33*b*, as shown, after the distal portion of the needle guide channel 3103 is articulated, the needle 3107 may be advanced out of the needle guide channel 3103 and into a puncture site of interest. In some embodiments, the needle 3107 is used to gather and remove tissue for a biopsy sample. As shown in the illustrated figures, and in the context of a DIPS procedure, the needle 3107 is advanced out of the IVC, through the caudate lobe of the liver, and into the portal vein.

FIGS. 34*a* and 34*b* illustrate that after the position of the needle is verified using ultrasonic visualization, the guidewire 2109 may be advanced through the needle 3107 and further into the portal vein. The position of the guidewire 2109 may be further verified using ultrasonic visualization.

Turning to FIGS. 35*a* and 35*b*, after the guidewire is verified to be in the desired position, the needle 3107 may be withdrawn 2109 over the wire 2109 and out of the NGS 3100. Accordingly, the guidewire forms a tract from the IVC to the PV which can be used to create a shunt between the two veins. As shown in FIGS. 36*a* and 36*b*, after the guidewire is in the correct position, the IVUS probe may be withdrawn from the NGS 3100. As shown, because the cross-sectional width of the guidewire is less than the width of the passage 2108, the guidewire may be moved from the needle guide channel 2103 and into the lumen 2100.

Moving on to FIGS. 37*a* and 37*b*, a working sheath 2120 may be advanced over the guidewire 2109 and through the NGS 3100. Advancing the working sheath 2120 over the guidewire 2109 and through the NGS 3100 further strips the guidewire 2109 out of the needle guide channel 2103, through the passage 2108, and into the central lumen 2100.

With reference to FIGS. 38*a* and 38*b*, the distal portion 3105 of the needle guide channel 3103 may be moved into the relaxed or unarticulated position. The working sheath 3120 may also be advanced out of the NGS 3100 and/or the NGS may be slightly withdrawn such that at least a portion of the working sheath 2120 extends outside of the NGS 3100. A shown in FIGS. 39*a* and 39*b*, a collapsible, covered stent 2125, angioplasty balloon, or similar device may be advanced over the guidewire 2109. The collapsible, covered stent 2125 may be inflated providing a shunt between the PV and the IVC.

Moving now to FIG. 40, a flow diagram illustrating and example method 4020 for performing a DIPS procedure is shown. The method may begin at block 4001 by inserting a sheath having a needle guide into a patient's vasculature through an insertion point. The insertion point may be the patient's jugular vein. The guide sheath may be advanced to the desired location within the patient's vasculature. In some embodiments, the guide sheath is advanced over a guidewire. The method may continue at block 4003 by advancing an imaging device through the guide sheath. In some embodiments, the imaging device comprises an ultrasonic probe configured to be connected to an ultrasonic imaging device. The method may continue at block 4005 by articulating at least a distal portion of the needle guide and advancing a needle having an internal wire through the needle guide while imaging a puncture site and at least a portion of the needle. While imaging the needle and the puncture site, the method may continue at block 4007 by advancing the needle and internal wire through the puncture site. After the needle is in the desired position, the method can continue at block 4009 by removing the needle over the wire and by removing the imaging device through the sheath. The method may end at block 4011 by advancing a working sheath though the guide sheath and over the guidewire. Advancing the working sheath may remove the guidewire from the needle guide channel.

Moving on to FIGS. 41-46, an IVUS device 4100 having a detachable needle guide assembly is shown. As shown in FIG. 41*b*, according to one embodiment, the device 4100 comprises an IVUS catheter having a needle guide 4103 passing therethrough. The needle guide 4102 may comprise a lumen extending through at least a portion of the device. In other embodiments, the needle guide may be coupled to the external surface of an IVUS device 4100. The needle guide 4103 includes an articulating distal portion 4105 similar to the embodiments described above. As shown in FIGS. 41*a* and 41*b*, the IVUS device 4100 may be advance through a sheath 4105. The sheath 4105 may have been advanced over a guidewire. In some embodiments, the IVUS device 4100 is configured to be advance over a guidewire to a position of interest. The guidewire may be used to secure the IVUS device 4100 and/or sheath 4105 within the center of a vessel. Moreover, as described above, the guidewire may help stabilize the device and hold the device in place while a needle is advanced out of the vessel. Continuing with FIGS. 41*a* and 41*b*, a flexible needle 3107 having an internal guidewire 2109 may be advanced through the needle guide 4103.

As shown in FIGS. 42*a* and 42*b*, when the device 4100 is placed in the desired position, the distal portion 4105 of the needle guide 4103 may be articulated away from the center of the IVUS device such that the distal portion 4105 is positioned at an angle away from the exterior surface of the device 4100. In this way, when the angle at which the needle exits the device may be more accurately controlled. Moreover the articulating distal portion is configured to ensure that the needle is advanced within the field of view of the IVUS. Although not shown, one or more balloons may be deployed from the IVUS device and/or the sheath to further stabilize the IVUS device and/or the sheath within the vessel.

Figures 43A, 43B:
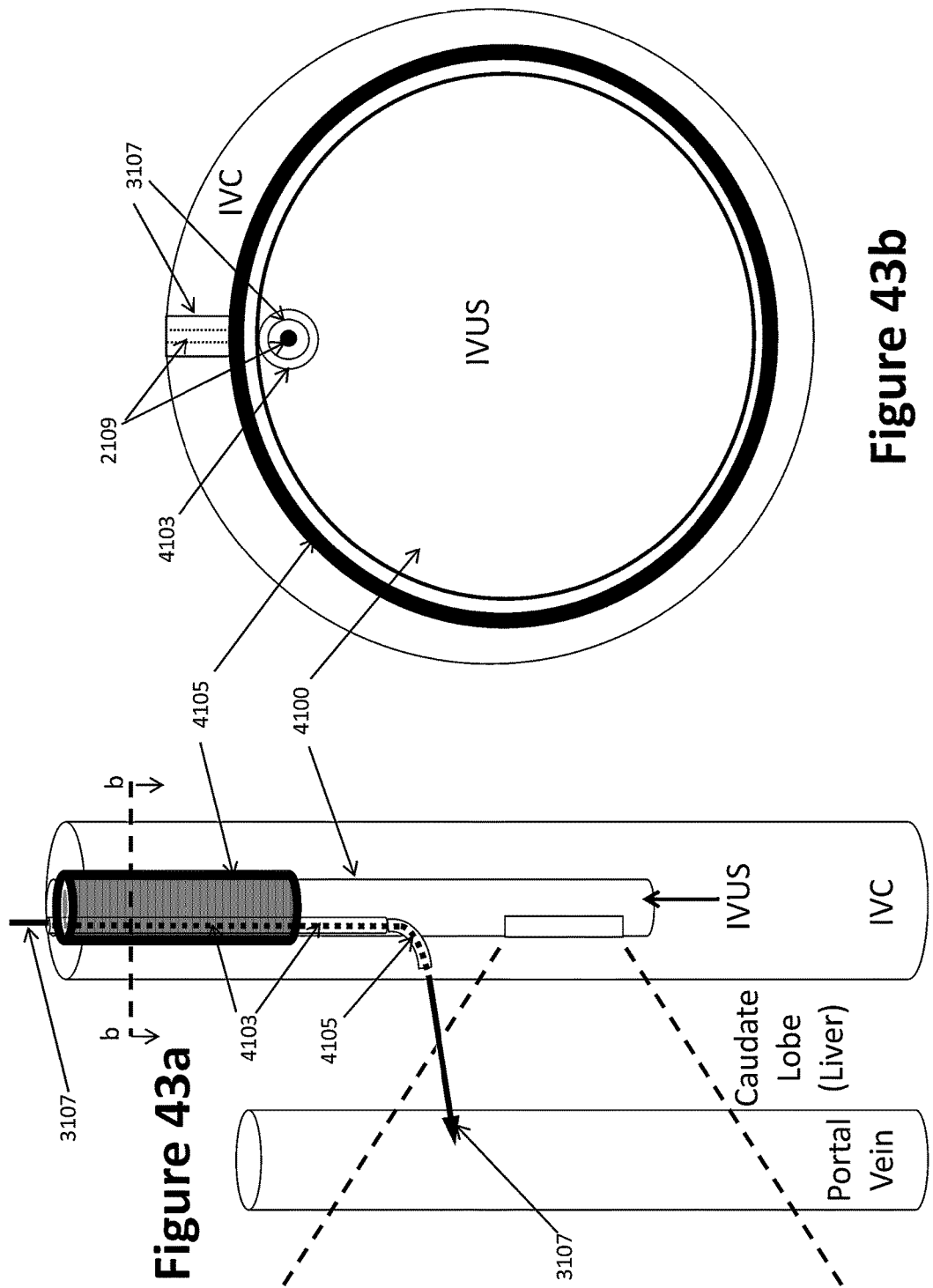
FIGS. 43a and 43b are the same as FIGS. 42a and 42b except that needle having an internal guidewire is advanced out of the needle guide and into the portal vein.

Turning to FIGS. 43*a* and 43*b*, the needle 3107 having an internal guidewire 2109 may be advanced out of the vessel and into the place of interest. In some embodiments, the needle is advanced without the internal guidewire in place. In the case of this illustrated DIPS procedure, the needle 3107 and internal guidewire 2109 are advanced out of the IVC, through the caudate lobe, and into the portal vein. This entire procedure may be visualized using the IVUS device 4100. After the needle 3107 position is verified, the guidewire 2109 may be further advanced through the needle 3107 and into the PV as shown in FIGS. 44*a* and 44*b*. The needle 3107 may then be removed from the needle guide 4103 leaving the guidewire 2109 in place as shown in FIGS. 45*a* and 45*b*. In some embodiments, the DIPS procedure may continue by working within the needle guide 4103. For example, a dilator and/or collapsed balloon shunt may be passed over the wire and within the needle guide 4103 to complete the shunt procedure.

Removing the IVUS device may facilitate ease of working through the needle guide 4103 for the remainder of the procedure. For example, the walls of the needle guide may be made of a pliable material such that when the IVUS is removed, the needle guide can expand when larger diameter objects are passed through the needle guide 4103. Alternatively, the needle guide 4103 may be withdrawn, leaving the guidewire 2109 within the sheath 4105 alone and further procedures may be conducted over the guidewire 2109. Accordingly, as shown in FIGS. 46*a* and 46*b*, the needle guide 4103 may be configured to separate from the IVUS device 4100. For example, the IVUS device 4100 may be configured to slide with respect to the needle guide 4103 such that the IVUS is essentially withdrawn over or away from the needle guide 4103. A similar device 4120 according to another embodiment is shown in FIG. 47*a* and FIG. 47*b*. This embodiment may aid in separating and withdrawing the IVUS probe from the needle guide 4103. As show in FIG. 47*a*, the IVUS probe has at least a distal portion that has a diameter that is less than the diameter of the remainder of the IVUS probe. In other embodiments, a device similar to the embodiment shown in FIGS. 5-6 may be used. For example, the needle guide 210 in FIGS. 5-6 may be configured to separate from the IVUS device 130. Such devices may be used to perform any of the methods described herein.

Figure 48:
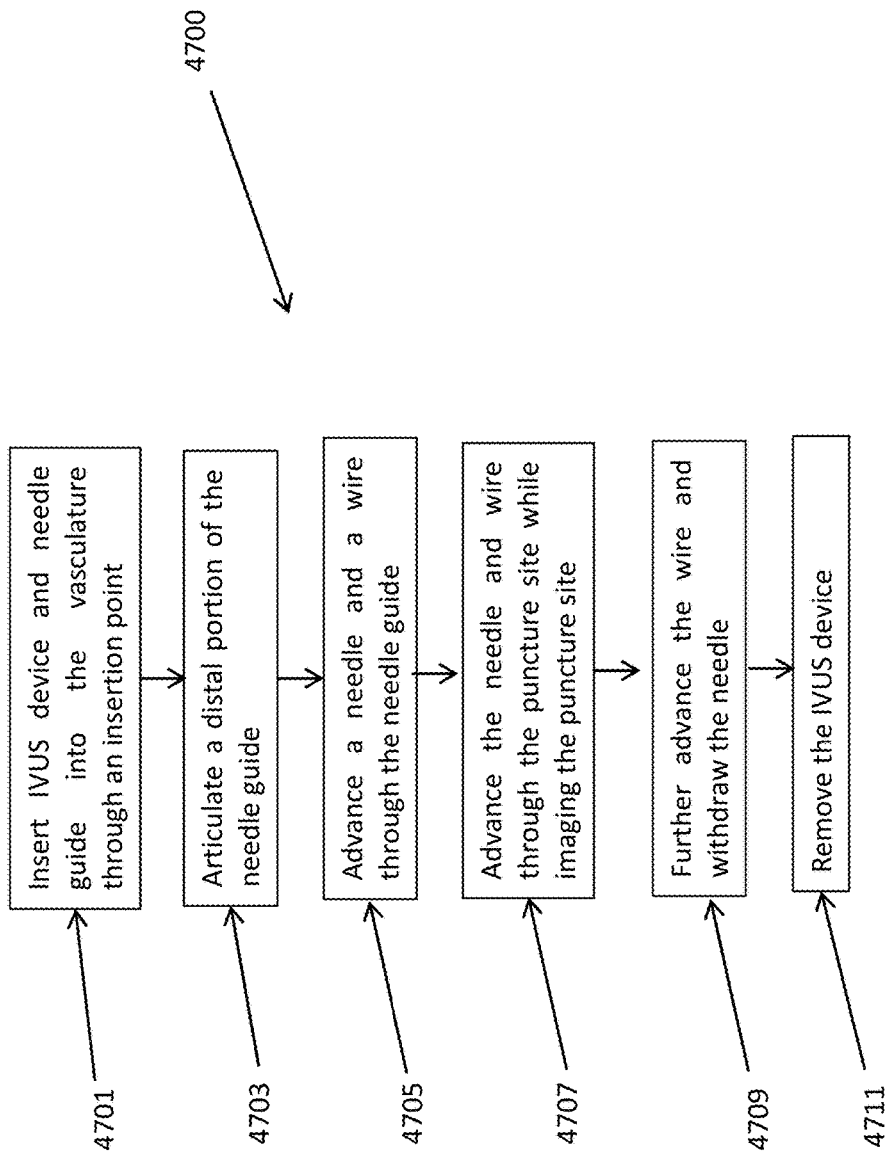
FIG. 48 is a flow diagram illustrated a method of preforming a surgical procedure according to one embodiment.

FIG. 48, illustrates a flow diagram illustrating and example method 4700 of performing a medical procedure. The method may begin at block 4701 by inserting an IVUS device and a needle guide into a patient's vasculature through an insertion point. When the IVUS and needle guide are in the desired position, the method can continue at block 4703 by articulating a distal portion of the needle guide away from the IVUS. The method can continue at block 4705 by advancing a needle and a wire through the needle guide. The method can continue at block 4707 by advancing the needle and the wire through a puncture site while imaging the puncture site. The wire may be advanced after the needle is advanced through the puncture site. The method can continue at block 4709 by further advancing the wire and by withdrawing the needle. The needle can be withdrawn over the wire. The method may end at block 4711 by removing the IVUS device. The needle guide may remain. In some embodiments, the method may include the step of detaching and/or removing the IVUS from the needle guide.

It is to be understood that the needle for any and all previous described embodiments or portions thereof may be advanced in an automated manner. For example, the needles may be advanced using with an adjustable length throw device configured to provide the force to advance the needle at precise increments of length. Such devices may be useful to assist puncturing form tissues and/or organs (e.g., a cirrhotic liver).

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Moreover, the skilled artisan will recognize the interchangeability of various features from different embodiments. In other words, the features of the devices disclosed in the various embodiments can be switched between embodiments. For example, certain features of the embodiments shown in FIGS. 7-10 may be used be used in connection with or instead of certain features shown in FIGS. 9-29, 31-39, and/or 41-47. Other combinations of the various aspects of the disclosed embodiments are possible as well. In addition to the variations described herein, other known equivalents for each feature can be mixed and matched by one of ordinary skill in this art to construct systems and techniques to ensure that a needle is directed into the plane of an IVUS array in accordance with principles of the present invention.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A unitary probe for performing an intravascular medical procedure, the unitary probe comprising:
    a body having a proximal end, a distal end, an ultrasonic array, and a needle guide, the ultrasonic array being fixed in the body and having a visualization area radiating outwardly from a side of the body, the needle guide being fixed in the body and prevented from both rotating or translating relative to the probe, the needle guide having a lumen extending therethrough, the lumen having a proximal opening and a distal opening, the lumen of the needle guide being sized and shaped so that a flexible needle having a pre-curved shape passing through the lumen is straightened by the lumen and then reassumes its pre-curved shape when exiting the distal opening while maintaining an in-plane relationship with the visualization area of the ultrasonic array,
    wherein the needle guide further comprises a distal portion, the distal portion being configured to selectively articulate from a first position that is generally parallel to the probe and to a second position that is angled away from the probe.

2. The unitary probe of claim 1, wherein at least a portion of the lumen of the needle guide has a non-round shape so that the needle is inhibited from rotation within the needle guide.

3. The unitary probe of claim 1, wherein the ultrasonic array is positioned at the distal end of the body.

* * * * *